US012741930B2

(12) United States Patent
Song et al.

(10) Patent No.: US 12,741,930 B2
(45) Date of Patent: Sep. 22, 2026

(54) LONG-ACTING SPLEEN-TARGETING CATIONIC LIPID COMPOUND COMPRISING BENZENE RING STRUCTURE, COMPOSITION COMPRISING SAME, AND USE THEREOF

(71) Applicant: Beijing Youcare Kechuang Pharmaceutical Technology Co., Ltd., Beijing (CN)

(72) Inventors: Gengshen Song, Beijing (CN); Honglei Zhang, Beijing (CN); Yuqing Ma, Beijing (CN); Lijie Jin, Beijing (CN); Jing Li, Beijing (CN)

(73) Assignee: Beijing Youcare Kechuang Pharmaceutical Technology Co., Ltd., Beijing (CN)

( * ) Notice: Subject to any disclaimer, the term of this patent is extended or adjusted under 35 U.S.C. 154(b) by 0 days.

(21) Appl. No.: 19/181,470

(22) Filed: Apr. 17, 2025

(65) Prior Publication Data

US 2025/0326708 A1 Oct. 23, 2025

(30) Foreign Application Priority Data

Apr. 17, 2024 (CN) ........................ 202410463794.9

(51) Int. Cl.
*C07C 229/14* (2006.01)
*A61K 39/385* (2006.01)
*A61K 48/00* (2006.01)

(52) U.S. Cl.
CPC .......... *C07C 229/14* (2013.01); *A61K 39/385* (2013.01); *A61K 48/0033* (2013.01)

(58) Field of Classification Search
CPC .. C07C 229/14; A61K 39/385; A61K 48/0033
See application file for complete search history.

(56) References Cited

U.S. PATENT DOCUMENTS

| | | | | |
|---|---|---|---|---|
| 11,472,766 | B2 * | 10/2022 | Ying .................... | C07D 307/22 |
| 2005/0222064 | A1 | 10/2005 | Vargeese et al. | |
| 2006/0083780 | A1 | 4/2006 | Heyes et al. | |
| 2013/0059801 | A1 | 3/2013 | Milne et al. | |
| 2020/0331841 | A1 | 10/2020 | Matsumoto et al. | |
| 2021/0052520 | A1 | 2/2021 | Polotsky et al. | |
| 2022/0009878 | A1 | 1/2022 | Parmar et al. | |
| 2023/0119606 | A1 | 4/2023 | Sherden et al. | |

FOREIGN PATENT DOCUMENTS

| | | | |
|---|---|---|---|
| CN | 101163796 | A | 4/2008 |
| CN | 102245590 | B | 3/2014 |
| CN | 102625696 | B | 6/2015 |
| CN | 107304170 | A | 10/2017 |
| CN | 107847588 | A | 3/2018 |
| CN | 110799492 | A | 2/2020 |
| CN | 113039174 | A | 6/2021 |
| CN | 112979483 | B | 8/2021 |
| CN | 108368028 | B | 9/2021 |
| CN | 114206827 | A | 3/2022 |
| CN | 114044741 | B | 4/2022 |
| CN | 115745820 | A | 3/2023 |
| CN | 116082275 | B | 7/2023 |
| CN | 116178193 | B | 7/2023 |
| EA | 024960 | B1 | 11/2016 |
| EA | 041756 | B1 | 11/2022 |
| EA | 045069 | B1 | 10/2023 |
| EP | 4588910 | A1 | 7/2025 |
| RU | 2782218 | C2 | 1/2022 |
| WO | 2010144740 | A1 | 12/2010 |
| WO | 2013033602 | A2 | 3/2013 |
| WO | 2017049245 | A2 | 3/2017 |
| WO | 2018078053 | A1 | 5/2018 |
| WO | 2018200943 | A1 | 11/2018 |

OTHER PUBLICATIONS

Testa et al. (Biomacromolecules, 2022, vol. 23, pp. 2976-2988) (Year: 2022).*

Zhang et al. (Chem. Rev. 2021, vol. 121, pp. 12181-12277) (Year: 2021).*

Oct. 26, 2024 First Office Action issued in Chinese Patent Application No. 202410463794.9.

Oct. 14, 2024 First Search Report issued in Chinese Patent Application No. 202410463794.9.

Dec. 19, 2024 Second Office Action issued in Chinese Patent Application No. 202410463794.9.

Feb. 26, 2025 Supplementary Search Report issued in Chinese Patent Application No. 202410463794.9.

T. Coelho, D. Adams, A. Silva et al., Safety and efficacy of RNAi therapy for transthyretin amyloidosis, N Engl J Med, 369 (2013), pp. 819-829.

S. M. Berge et al., Pharmaceutical Salts, J. Pharm. Sci., Jan. 1977, 66 (1), 1-19.

(Continued)

*Primary Examiner* — Traviss C McIntosh, III

(57) ABSTRACT

The present disclosure relates to the field of medicine, specifically to a long-acting spleen-targeting cationic lipid compound comprising a benzene ring structure, a composition comprising the same, and a use thereof. More specifically, the present disclosure provides a compound of formula (I), or an N-oxide thereof, a solvate thereof, a pharmaceutically acceptable salt thereof, or a stereoisomer thereof. The present disclosure further provides a composition comprising the aforementioned compound and a use thereof in delivering therapeutic or prophylactic agents.

I

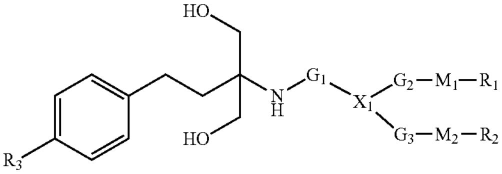

18 Claims, 3 Drawing Sheets

(56) References Cited

OTHER PUBLICATIONS

Mar. 4, 2025 Notice of Allowance issued in Chinese Patent Application No. 202410463794.9.
Apr. 30, 2025 First Office Action issued in New Zealand application No. 820531.
Jun. 24, 2025 Second Office Action issued in New Zealand application No. 820531.
Jul. 10, 2025 First Office Action issued in Eurasian application No. 202590945.
Feb. 26, 2026 First Office Action issued in Taiwanese application No. 114114187.

* cited by examiner

LONG-ACTING SPLEEN-TARGETING CATIONIC LIPID COMPOUND COMPRISING BENZENE RING STRUCTURE, COMPOSITION COMPRISING SAME, AND USE THEREOF

CROSS-REFERENCE TO RELATED APPLICATION

The present application claims priority from Chinese Patent Application No. 202410463794.9 filed on Apr. 17, 2024, the contents of which are incorporated herein by reference in their entirety.

TECHNICAL FIELD

The present disclosure relates to the field of medicine. The present disclosure specifically relates to a long-acting spleen-targeting cationic lipid compound comprising a benzene ring structure, a composition comprising the same, and a use thereof.

BACKGROUND

The effective targeted delivery of bioactive substances, such as small molecule drugs, polypeptides, proteins, and nucleic acids—particularly nucleic acids—has been a persistent medical challenge. Nucleic acid therapeutic agents face significant challenges due to their low cellular permeability and high susceptibility to degradation against certain nucleic acid molecules, including RNA.

It has been confirmed that compositions containing cationic lipids, liposomes, and liposome complexes (lipoplexes) serve as transport vehicles for effectively transporting bioactive substances, such as small molecule drugs, polypeptides, proteins, and nucleic acids, into cells and/or intracellular compartments. These compositions generally comprise one or more "cationic" and/or amino (ionizable) lipids, including neutral lipids, structural lipids, and polymer-conjugated lipids. Cationic and/or ionizable lipids include, for example, amine-containing lipids that can be readily protonated. Though various lipid-containing nanoparticle compositions have been made public, their safety, efficacy, and specificity still need improvement. It is noteworthy that the increasing complexity of lipid nanoparticles (LNPs) complicates their production and may increase their toxicity, which is a major concern that may limit their clinical application. For example, LNP siRNA particles (such as patisiran) require pre-treatment with steroids and antihistamines to prevent unnecessary immune reactions (T. Coelho, D. Adams, A. Silva, et al., "Safety and efficacy of RNAi therapy for transthyretin amyloidosis", N Engl J Med, 369 (2013) 819-829). Therefore, there is a need to develop an improved cationic lipid compound and a composition comprising the same to facilitate the delivery of therapeutic and/or prophylactic agents (such as nucleic acids) to cells, thereby meeting the demands of production and clinical application.

CONTENT OF THE PRESENT INVENTION

A first aspect of the present disclosure provides a new cationic lipid compound, as a compound of formula (I)

I

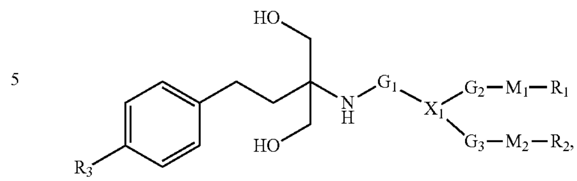

or an N-oxide thereof, a solvate thereof, a pharmaceutically acceptable salt thereof, or a stereoisomer thereof, wherein $G_1$ is $C_{1-4}$ alkylene;

$G_2$ is $C_{1-8}$ alkylene;

$G_3$ is $C_{2-8}$ alkylene or H;

$R_1$ is $C_{6-25}$ linear alkyl, $C_{6-25}$ branched alkyl, or $C_{6-25}$ substituted alkyl;

$R_2$ is $C_{6-25}$ linear alkyl, $C_{6-25}$ branched alkyl, $C_{6-25}$ substituted alkyl, or H;

$R_3$ is $C_{1-25}$ linear alkyl, $C_{1-25}$ branched alkyl, $C_{1-25}$ substituted alkyl, or H;

$M_1$ is —C(O)O—, —OC(O)—, —C(O) N(R')—, —N(R') C(O)—, —C(O)—, —C(S)—, —C(S)S—, —SC(S)—, —CH(OH)—, —P(O) (OR')O—, —$S(O)_2$—, —S—S—, aryl, heteroaryl, or H;

$M_2$ is —C(O)O—, —OC(O)—, —C(O) N(R')—, —N(R') C(O)—, —C(O)—, —C(S)—, —C(S)S—, —SC(S)—, —CH(OH)—, —P(O) (OR')O—, —$S(O)_2$—, —S—S—, aryl, heteroaryl, or H;

R' is $C_{1-18}$ alkyl, $C_{2-18}$ alkenyl, or H;

$X_1$ is —CH— or N.

A further compound of formula (I), or an N-oxide thereof, a solvate thereof, a pharmaceutically acceptable salt thereof, or a stereoisomer thereof, wherein $G_1$ is unsubstituted $C_1$ alkylene.

A further compound of formula (I), or an N-oxide thereof, a solvate thereof, a pharmaceutically acceptable salt thereof, or a stereoisomer thereof, wherein $G_1$ is unsubstituted $C_2$ alkylene.

A further compound of formula (I), or an N-oxide thereof, a solvate thereof, a pharmaceutically acceptable salt thereof, or a stereoisomer thereof, wherein $G_2$ is unsubstituted $C_1$ alkylene.

A further compound of formula (I), or an N-oxide thereof, a solvate thereof, a pharmaceutically acceptable salt thereof, or a stereoisomer thereof, wherein $G_2$ is unsubstituted $C_3$ alkylene.

A further compound of formula (I), or an N-oxide thereof, a solvate thereof, a pharmaceutically acceptable salt thereof, or a stereoisomer thereof, wherein $G_2$ is unsubstituted $C_4$ alkylene.

A further compound of formula (I), or an N-oxide thereof, a solvate thereof, a pharmaceutically acceptable salt thereof, or a stereoisomer thereof, wherein $G_3$ is H.

A further compound of formula (I), or an N-oxide thereof, a solvate thereof, a pharmaceutically acceptable salt thereof, or a stereoisomer thereof, wherein $G_3$ is unsubstituted $C_5$ alkylene.

A further compound of formula (I), or an N-oxide thereof, a solvate thereof, a pharmaceutically acceptable salt thereof, or a stereoisomer thereof, wherein $G_3$ is unsubstituted $C_6$ alkylene.

A further compound of formula (I), or an N-oxide thereof, a solvate thereof, a pharmaceutically acceptable salt thereof, or a stereoisomer thereof, wherein $R_1$ is $C_{6-14}$ linear alkyl.

A further compound of formula (I), or an N-oxide thereof, a solvate thereof, a pharmaceutically acceptable salt thereof, or a stereoisomer thereof, wherein $R_1$ is $C_{12-25}$ branched alkyl.

A further compound of formula (I), or an N-oxide thereof, a solvate thereof, a pharmaceutically acceptable salt thereof, or a stereoisomer thereof, wherein $R_1$ is

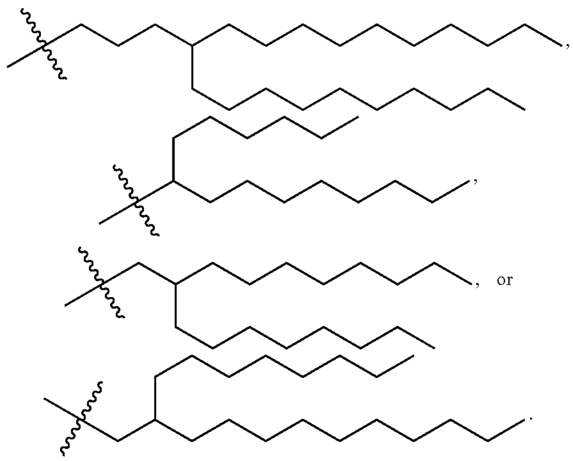

A further compound of formula (I), or an N-oxide thereof, a solvate thereof, a pharmaceutically acceptable salt thereof, or a stereoisomer thereof, wherein $R_2$ is $C_{6-14}$ linear alkyl.

A further compound of formula (I), or an N-oxide thereof, a solvate thereof, a pharmaceutically acceptable salt thereof, or a stereoisomer thereof, wherein $R_2$ is $C_{12-25}$ branched alkyl.

A further compound of formula (I), or an N-oxide thereof, a solvate thereof, a pharmaceutically acceptable salt thereof, or a stereoisomer thereof, wherein $R_2$ is

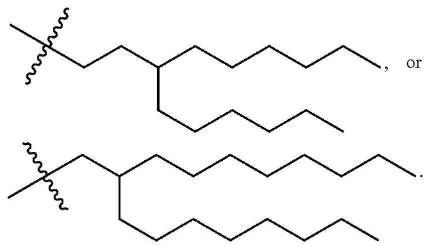

A further compound of formula (I), or an N-oxide thereof, a solvate thereof, a pharmaceutically acceptable salt thereof, or a stereoisomer thereof, wherein $R_2$ is H.

A further compound of formula (I), or an N-oxide thereof, a solvate thereof, a pharmaceutically acceptable salt thereof, or a stereoisomer thereof, wherein $R_3$ is $C_{4-15}$ linear alkyl.

A further compound of formula (I), or an N-oxide thereof, a solvate thereof, a pharmaceutically acceptable salt thereof, or a stereoisomer thereof, wherein $R_3$ is $C_8$ linear alkyl.

In the compound of formula (I), or the N-oxide thereof, the solvate thereof, the pharmaceutically acceptable salt thereof, or the stereoisomer thereof of the present disclosure, $M_1$ and $M_2$ may be the same or different.

A further compound of formula (I), or an N-oxide thereof, a solvate thereof, a pharmaceutically acceptable salt thereof, or a stereoisomer thereof, wherein $M_1$ is —C(O)O—.

A further compound of formula (I), or an N-oxide thereof, a solvate thereof, a pharmaceutically acceptable salt thereof, or a stereoisomer thereof, wherein $M_1$ is —C(O)NH—.

A further compound of formula (I), or an N-oxide thereof, a solvate thereof, a pharmaceutically acceptable salt thereof, or a stereoisomer thereof, wherein $M_1$ is —NHC(O)—.

A further compound of formula (I), or an N-oxide thereof, a solvate thereof, a pharmaceutically acceptable salt thereof, or a stereoisomer thereof, wherein $M_2$ is H. A further compound of formula (I), or an N-oxide thereof, a solvate thereof, a pharmaceutically acceptable salt thereof, or a stereoisomer thereof, wherein $M_2$ is —C(O)O—.

A further compound of formula (I), or an N-oxide thereof, a solvate thereof, a pharmaceutically acceptable salt thereof, or a stereoisomer thereof, wherein $X_1$ is —CH—.

A further compound of formula (I), or an N-oxide thereof, a solvate thereof, a pharmaceutically acceptable salt thereof, or a stereoisomer thereof, wherein $X_1$ is N.

In the compound of formula (I), or the N-oxide thereof, the solvate thereof, the pharmaceutically acceptable salt thereof, or the stereoisomer thereof of the present disclosure, the compound of formula (I) can be compound of formula (I-1);

(I-1)

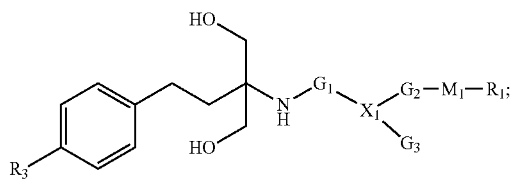

Wherein $G_3$ is H;

$G_1$, $G_2$, $R_1$, $R_3$, $M_1$, $X_1$ are as defined in the present disclosure.

A further compound of formula (I), or an N-oxide thereof, a solvate thereof, a pharmaceutically acceptable salt thereof, or a stereoisomer thereof, wherein the compound of formula (I) is at least one of compounds YK-901, YK-902, YK-903, YK-904, YK-905, YK-906, YK-907, YK-908, YK-909, YK-910, YK-911, and YK-912, having structures as follows:

YK-901

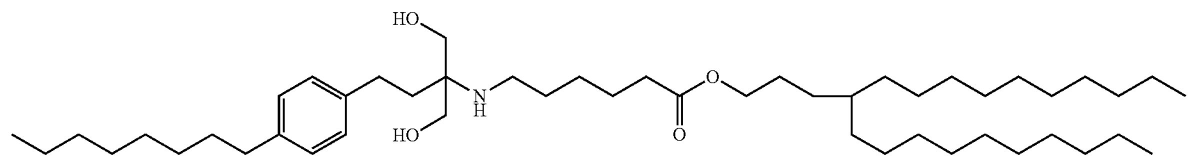

,

-continued
YK-902
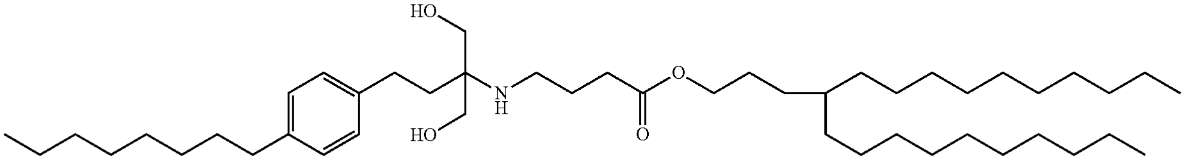
,
YK-903
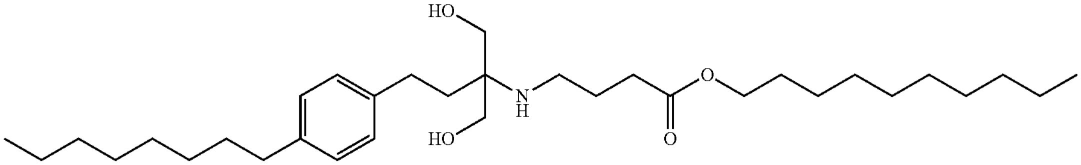
,
YK-904
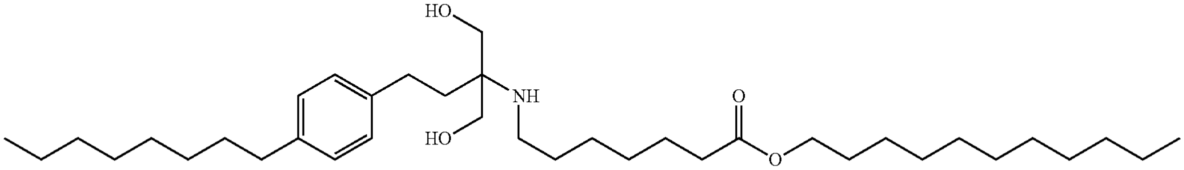
,
YK-905
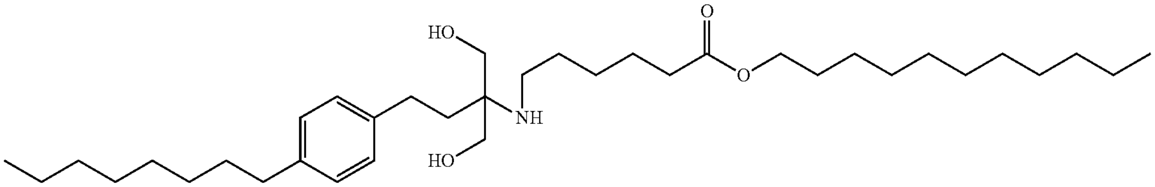
,
YK-906
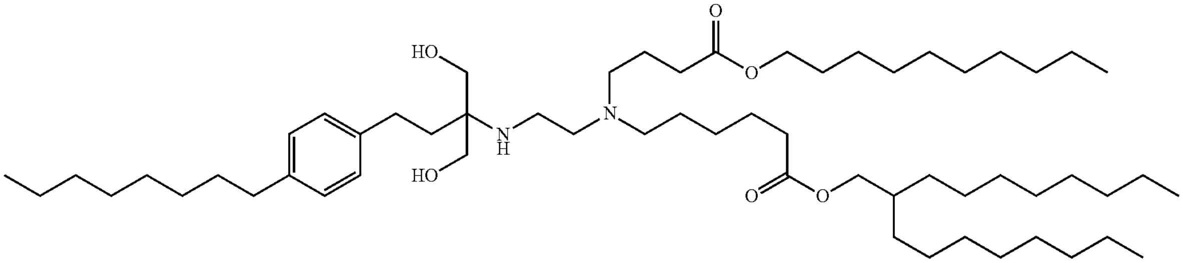
,
YK-907
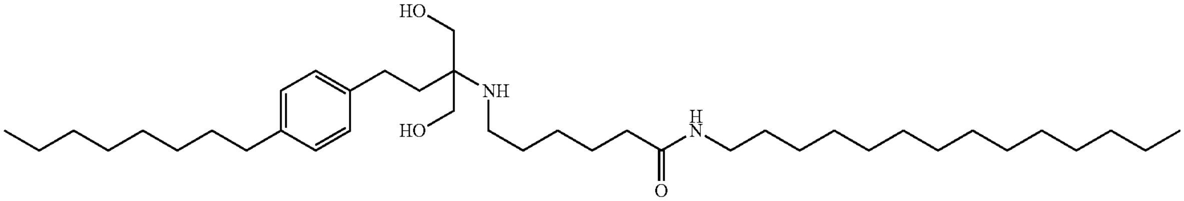
,
YK-908
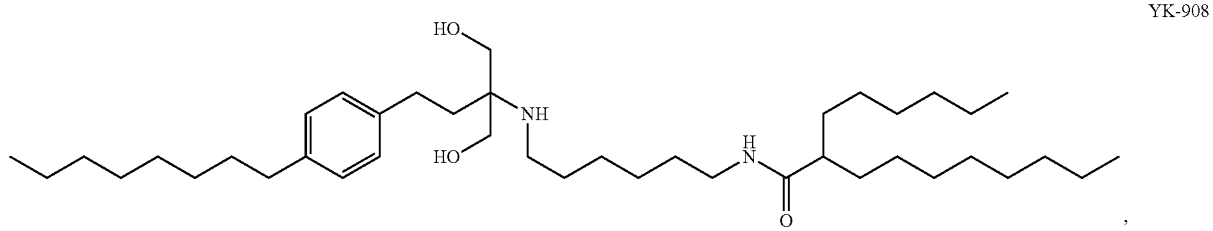
, -continued

YK-909

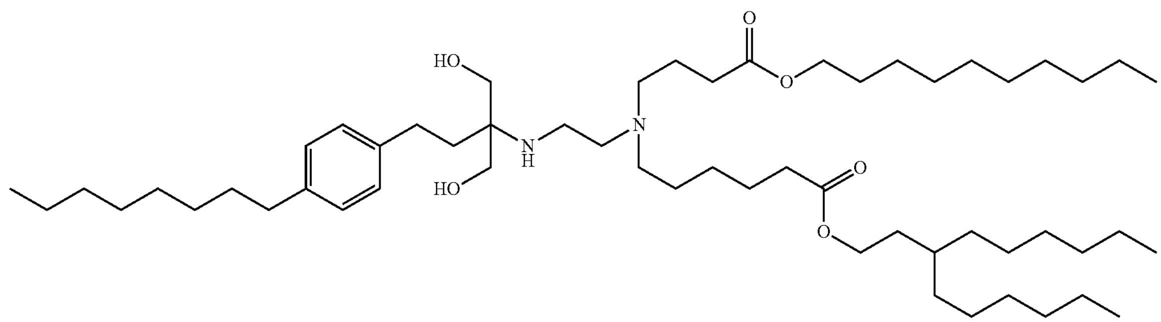

,

YK-910

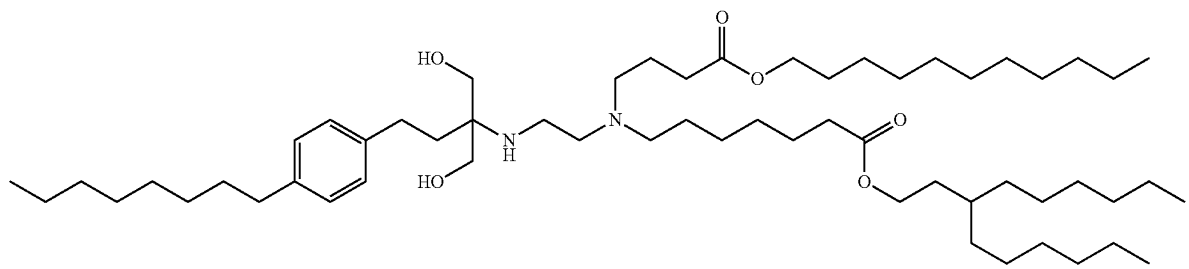

,

YK-911

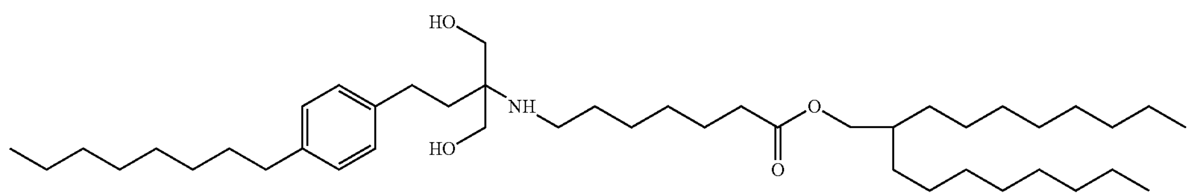

,

YK-912

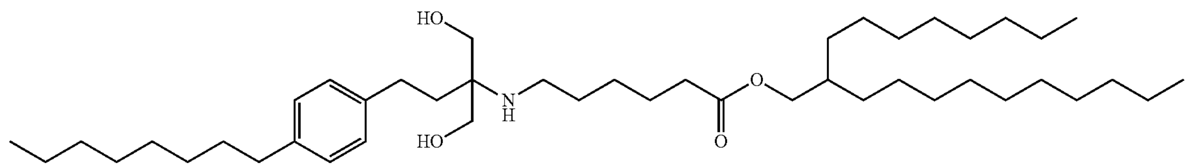

.

A further compound of formula (I), or an N-oxide thereof, a solvate thereof, a pharmaceutically acceptable salt thereof, or a stereoisomer thereof, wherein the compound of formula (I) is compound YK-908 having a structure as follows:

YK-908

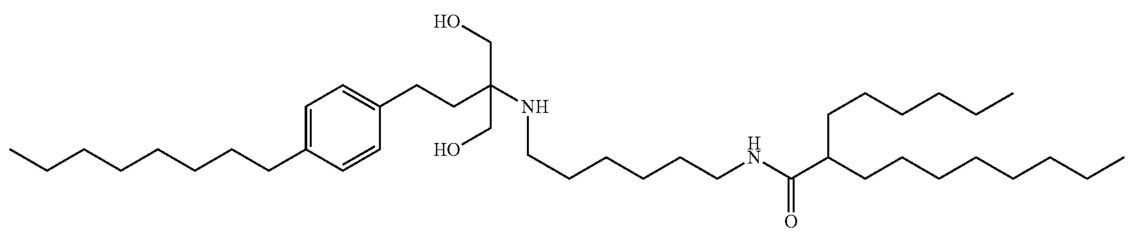

A further compound of formula (I), or an N-oxide thereof, a solvate thereof, a pharmaceutically acceptable salt thereof, or a stereoisomer thereof, wherein the compound of formula (I) is compound YK-909 having a structure as follows:

YK-909

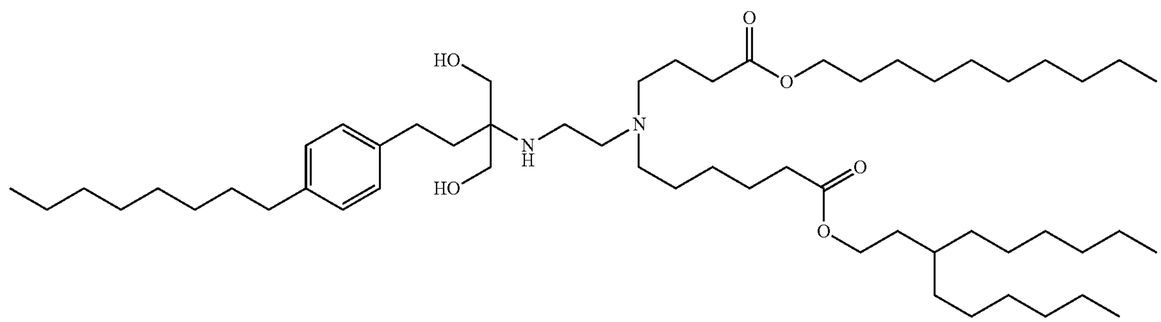

A preferred composition, wherein the neutral lipid comprises one or more of phosphatidylcholine, phosphatidylethanolamine, sphingomyelin, ceramide, sterol, and derivatives thereof.

A further compound of formula (I), or an N-oxide thereof, a solvate thereof, a pharmaceutically acceptable salt thereof, or a stereoisomer thereof, wherein the compound of formula (I) is compound YK-910 having a structure as follows:

YK-910

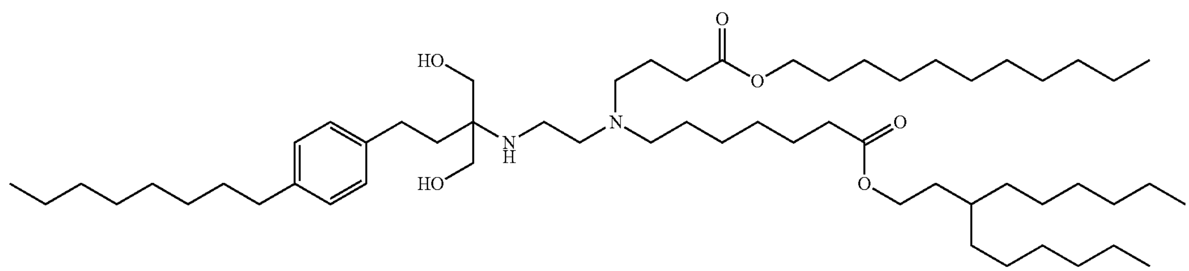

A further compound of formula (I), or an N-oxide thereof, a solvate thereof, a pharmaceutically acceptable salt thereof, or a stereoisomer thereof, wherein the compound of formula (I) is compound YK-912 having a structure as follows:

YK-912

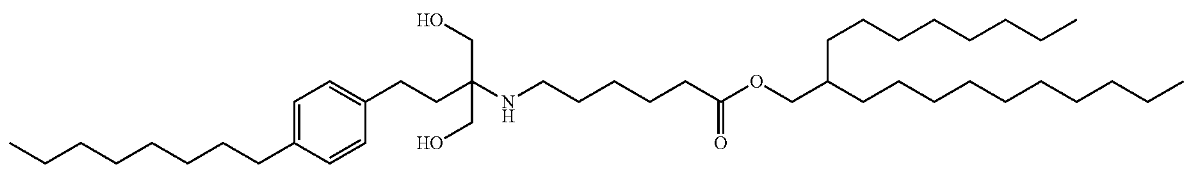

A second aspect of the present disclosure provides a composition comprising a vector, wherein the vector comprises a cationic lipid, and the cationic lipid comprises the compound of formula (I), or the N-oxide thereof, the solvate thereof, the pharmaceutically acceptable salt thereof, or the stereoisomer thereof as described in any item of the preceding first aspect.

A preferred composition, wherein the molar ratio of the cationic lipid in the vector is 25% to 75%.

A preferred composition, wherein the vector further comprises a neutral lipid.

A preferred composition, wherein the molar ratio of the cationic lipid to the neutral lipid is 1:1 to 15:1, preferably 4:1 to 5:1, most preferably 4.9:1.

A preferred composition, wherein the neutral lipid is selected from one or more of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine ($C_{16}$ Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

A preferred composition, wherein the neutral lipid is DOPE and/or DSPC.

A preferred composition, wherein the vector further comprises a structural lipid.

A preferred composition, wherein the molar ratio of the cationic lipid to the structural lipid is 0.6:1 to 3:1.

A preferred composition, wherein the structural lipid is selected from one or more of cholesterol, nonsterol, sitosterol, ergosterol, campesterol, stigmasterol, brassinosterol, tomatidine, ursolic acid, α-tocopherol, corticosteroid.

A preferred composition, wherein the structural lipid is cholesterol.

A preferred composition, wherein the vector further comprises a polymer-conjugated lipid.

A preferred composition, wherein the molar ratio of the polymer-conjugated lipid in the vector is 0.5% to 10%, preferably 1.5%.

A preferred composition, wherein the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, PEG-modified dialkylglycerol.

A preferred composition, wherein the polymer-conjugated lipid is selected from one or more of distearoyl phosphatidylethanolamine polyethylene glycol 2000 (DSPE-PEG2000), dimyristoylglycero-3-methoxypolyethylene glycol 2000 (DMG-PEG2000), and methoxypolyethylene glycol ditetradecylacetamide (ALC-0159).

A preferred composition, wherein the vector further comprises a neutral lipid, a structural lipid, and a polymer-conjugated lipid, and the molar ratio of the cationic lipid, the neutral lipid, the structural lipid, and the polymer-conjugated lipid is (25 to 75):(5 to 25):(15 to 65):(0.5 to 10).

A preferred composition, wherein the molar ratio of the cationic lipid, the neutral lipid, the structural lipid, and the polymer-conjugated lipid is (35 to 49):(7.5 to 15): (35 to 55):(1 to 5). Herein, the molar ratios of the cationic lipid, the neutral lipid, the structural lipid, and the polymer-conjugated lipid add up to 100.

A preferred composition, wherein the molar ratio of the cationic lipid, the neutral lipid, the structural lipid, and the polymer-conjugated lipid is 45:10:43.5:1.5 or 49:10:39.5:1.5.

A preferred composition, wherein the composition is a nanoparticle preparation, and the average particle size of the nanoparticle preparation is 10 nm to 300 nm; the polydispersity index of the nanoparticle preparation is ≤50%.

A preferred composition, wherein the composition is a nanoparticle preparation, and the average particle size of the nanoparticle preparation is 90 nm to 280 nm; the polydispersity index of the nanoparticle preparation is ≤45%.

A preferred composition, wherein the cationic lipid further comprises one or more other ionizable lipid compounds.

A preferred composition, further comprising a therapeutic or prophylactic agent.

A preferred composition, wherein the mass ratio of the vector to the therapeutic or prophylactic agent is 10:1 to 30:1.

A preferred composition, wherein the mass ratio of the vector to the therapeutic or prophylactic agent is 12.5:1 to 20:1.

A preferred composition, wherein the mass ratio of the vector to the therapeutic or prophylactic agent is 15:1.

A preferred composition, wherein the therapeutic or prophylactic agent comprises one or more of nucleic acid molecules, small molecule compounds, polypeptides, or proteins.

A preferred composition, wherein the therapeutic or prophylactic agent is a vaccine or compound capable of eliciting an immune response.

A preferred composition, wherein the therapeutic or prophylactic agent is nucleic acid.

A preferred composition, wherein the therapeutic or prophylactic agent is ribonucleic acid (RNA).

A preferred composition, wherein the therapeutic or prophylactic agent is deoxyribonucleic acid (DNA).

A preferred composition, wherein the RNA is selected from the group consisting of small interfering RNA (siRNA), asymmetric interfering RNA (aiRNA), microRNA (miRNA), dicer-substrate RNA (dsRNA), short hairpin RNA (shRNA), messenger RNA (mRNA), and mixtures thereof.

A preferred composition, wherein the RNA is mRNA.

A preferred composition, wherein the composition further comprises one or more pharmaceutically acceptable excipients or diluents.

A third aspect of the present disclosure provides a use of the compound of formula (I), or the N-oxide thereof, the solvate thereof, the pharmaceutically acceptable salt thereof, or the stereoisomer thereof as described in the first aspect, or the composition as described in the second aspect, in the preparation of nucleic acid drugs, gene vaccines, small molecule drugs, polypeptides, or protein drugs.

A fourth aspect of the present disclosure provides a use of the compound of formula (I), or the N-oxide thereof, the solvate thereof, the pharmaceutically acceptable salt thereof, or the stereoisomer thereof as described in the first aspect, or the composition as described in the second aspect, in the preparation of a drug for the treatment of a disease or condition in a subject in need thereof.

A further use, wherein the disease or condition is characterized by dysfunctional or abnormal protein or polypeptide activity.

A further use, wherein the disease or condition is selected from the group consisting of infectious diseases, cancer and proliferative diseases, genetic diseases, autoimmune diseases, diabetes, neurodegenerative diseases, cardiovascular and renal vascular diseases, and metabolic diseases.

A further use, wherein the infectious diseases are selected from diseases caused by coronaviruses, influenza viruses, or HIV viruses, pediatric pneumonia, rift valley fever, yellow fever, rabies, and various herpes.

A further use, wherein the subject is a mammal, preferably the mammal is a human.

A further use, wherein the composition is administered intravenously, intramuscularly, intradermally, subcutaneously, intranasally, or by inhalation.

A further use, wherein the composition is administered subcutaneously.

A further use, wherein the therapeutic or prophylactic agent is administered to the subject in a dose of about 0.001 mg/kg to about 10 mg/kg.

A fifth aspect of the present disclosure provides a use of the compound, or the N-oxide thereof, the solvate thereof, the pharmaceutically acceptable salt thereof, or the stereoisomer thereof as described in the first aspect in improving cellular transfection efficiency and/or reducing cytotoxicity, for example, in improving cellular transfection efficiency in vitro and/or reducing cytotoxicity in vitro.

A sixth aspect of the present disclosure provides a use of the compound, or the N-oxide thereof, the solvate thereof, the pharmaceutically acceptable salt thereof, or the stereoisomer thereof as described in the first aspect in enhancing the targeting specificity of nucleic acid drugs in organs and/or cells, and/or in increasing the expression levels of nucleic acid drugs in target organs and/or target cells.

A preferred embodiment according to the present disclosure, wherein the nucleic acid drug comprises mRNA.

A preferred embodiment according to the present disclosure, wherein the (exogenous) nucleic acid is mRNA.

BRIEF DESCRIPTION OF THE DRAWINGS

To more clearly illustrate the technical solutions of the examples of the present disclosure, a brief description to the drawings related to the examples is provided below. It is evident that the drawings described below are only related to some examples of the present disclosure and are not intended to limit the present disclosure.

DETAILED DESCRIPTION OF THE PREFERRED EMBODIMENT

Figure 1:
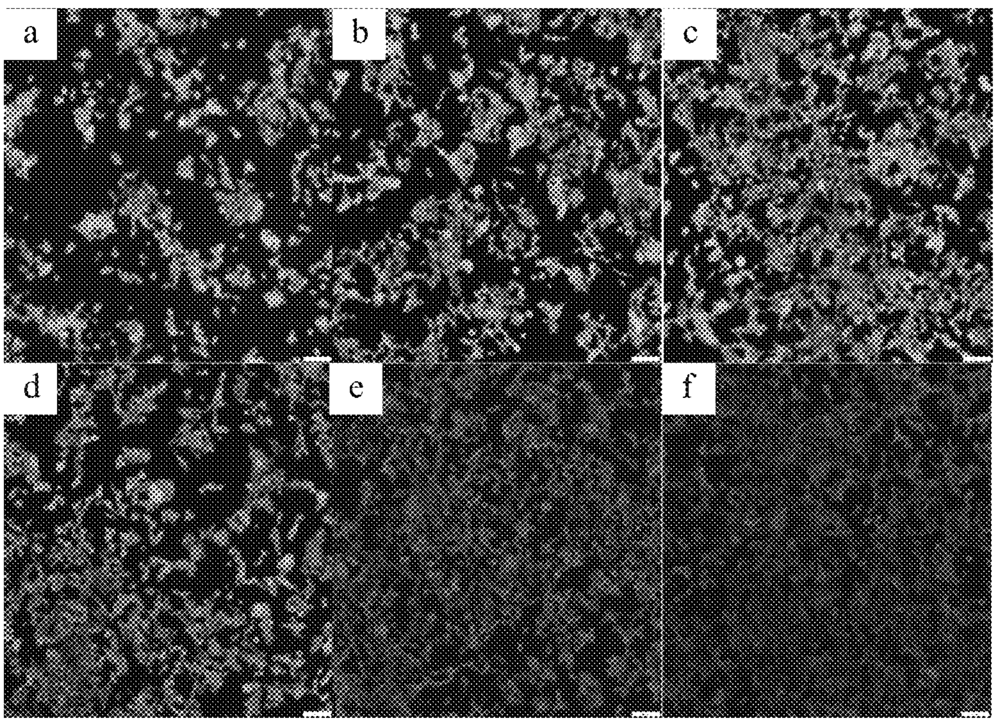
FIG. 1 shows the results of a cell transfection experiment for LNP preparations of Fluc-mRNA prepared with YK-908, YK-909, YK-910, YK-912, SM-102, and compound 7, where a represents YK-908, b represents YK-909, c represents YK-910, d represents YK-912, e represents SM-102, and f represents compound 7.

In order to make the purpose, technical solutions, and advantages of the embodiments of the present disclosure clearer, the technical solutions of the embodiments of the present disclosure will be clearly and completely described below in conjunction with the drawings of the examples of the present disclosure. Apparently, the described embodiments are some of the embodiments of the present disclosure, not all of them. Based on the described embodiments of the present disclosure, all other embodiments obtained by those of ordinary skill in the art without the need for creative effort shall fall within the scope of protection of the present disclosure.

The present disclosure may be embodied in other specific forms without departing from the essential attributes of the present disclosure. It should be understood that any and all embodiments of the present disclosure may be combined with technical features in any other embodiment or a plurality of other embodiments to obtain additional embodiments under the premise of no conflict. The present disclosure includes additional embodiments obtained from such combinations.

All publications and patents mentioned in the present disclosure are incorporated herein by reference in their entirety. If usage or terminology used in any publications and patents incorporated by reference conflicts with usage or terminology used in the present disclosure, the usage and terminology in the present disclosure shall prevail.

The section headings used herein are for the sole purpose of organizing the article and should not be construed as a limitation on the subject matter described.

Unless otherwise specified, all technical and scientific terms used herein have their ordinary meanings in the art to which the claimed subject matter pertains. If there are multiple definitions for a term, the definition herein shall prevail.

Except in the working examples or otherwise indicated, all numbers stating quantitative properties, such as doses, in the specification and claims should be understood as modified in all instances by the term "about". It should also be understood that any numerical range recited in the present disclosure is intended to include all sub-ranges within the range and any combination of the various endpoints of the range or sub-ranges.

The words "comprising", "including", or "containing" and similar words used in the present disclosure mean that the element appearing before the word covers the elements listed after the word and their equivalents, and does not exclude unrecited elements. The term "comprising" or "including (containing)" as used herein can be open, semi-closed, and closed. In other words, the term also includes "consisting essentially of" or "consisting of".

The term "pharmaceutically acceptable" in the present disclosure means that a compound or composition is chemically and/or toxicologically compatible with the other ingredients making up the preparation and/or with the human or mammal in which it is used to prevent or treat a disease or condition.

The term "subject" or "patient" in the present disclosure includes humans and mammals.

The term "treatment," as used herein, refers to the administration of one or more pharmaceutical substances to a patient or subject who has a disease or exhibits symptoms of the disease, with the aim of curing, alleviating, mitigating, improving, or affecting the disease or the symptoms of the disease. In the context of the present disclosure, unless specifically stated to the contrary, the term "treatment" may also include prevention.

The term "solvate" in the present disclosure refers to a complex formed by combining a compound of formula (I) or a pharmaceutically acceptable salt thereof with a solvent (e.g., ethanol or water). It should be understood that any solvate of a compound of formula (I) for use in the treatment of a disease or condition may provide different properties (including pharmacokinetic properties), however will result in the compound of formula (I) upon absorbed into a subject, such that the use of the compound of formula (I) encompasses the use of any solvate of the compound of formula (I) respectively.

The term "hydrate" refers to the situation where the solvent in the above term "solvate" is water.

It should be further understood that the compound of formula (I) or the pharmaceutically acceptable salt thereof may be isolated in the form of a solvate, and therefore any such solvate is included within the scope of the present disclosure. For example, the compound of formula (I) or the pharmaceutically acceptable salt thereof may exist in an unsolvated form as well as a solvated form with a pharmaceutically acceptable solvent (e.g., water, ethanol).

The term "pharmaceutically acceptable salt" refers to relatively non-toxic inorganic or organic acid addition salts of the compounds of the present disclosure. For example, see S. M. Berge et al., "Pharmaceutical Salts", *J. Pharm. Sci.* 1977, 66, 1-19. Herein, inorganic acids include, for example, hydrochloric acid, hydrobromic acid, hydroiodic acid, sulfuric acid, phosphoric acid, nitric acid, etc.; organic acids include, for example, formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphanic acid, cinnamic acid, cyclopentylpropionic acid, digluconic acid, 3-hydroxy-2-naphthoic acid, nicotinic acid, pamoic acid, pectinic acid, 3-phenylpropionic acid, picric acid, pivalic acid, 2-hydroxyethanesulfonic acid, itaconic acid, aminosulfonic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptonic acid, glycerophosphoric acid, aspartic acid, sulfosalicylic acid, etc. For example, a pharmaceutically acceptable salt can be formed using HCl (or hydrochloric acid), HBr (or hydrobromic acid solution), methanesulfonic acid, sulfuric acid, tartaric acid, or fumaric acid with the compound of formula (I).

The nitrogen-containing compounds of formula (I) in the present disclosure can be converted into N-oxides by treatment with oxidizing agents (such as m-chloroperbenzoic acid, hydrogen peroxide, or ozone). Therefore, where valence and structure allow, the compounds claimed in the present disclosure include not only the nitrogen-containing compounds of the structural formula but also their N-oxide derivatives.

Certain compounds of the present disclosure may exist as one or more stereoisomers. Stereoisomers include geometric isomers, diastereomers, and enantiomers. Accordingly, the claimed compounds of the present disclosure also include racemic mixtures, single stereoisomers, and optically active mixtures. It should be understood by those skilled in the art that one stereoisomer may have better efficacy and/or lower side effects than other stereoisomers. Single stereoisomers and optically active mixtures can be obtained by methods such as chiral source synthesis, chiral catalysis, and chiral resolution. The racemate can be chirally resolved by chromatographic resolution or chemical resolution. For example, a chiral acid resolution reagent such as chiral tartaric acid and chiral malic acid can be added to form a salt with the compound of the present disclosure, and the physicochemical properties of the product, such as the difference in solubility, can be utilized for separation.

The present disclosure also includes all suitable isotopic variants of the compounds of the present disclosure. Isotopic variants are defined as compounds in which at least one atom is replaced by an atom with the same atomic number but a different atomic mass than the naturally occurring or predominant atomic mass. Examples of isotopes that can be introduced into the compounds of the present disclosure include isotopes of hydrogen, carbon, nitrogen, and oxygen, such as $^{2}H$ (deuterium), $^{3}H$ (tritium), $^{11}C$, $^{13}C$, $^{14}C$, $^{15}N$, $^{17}O$, and $^{18}O$, respectively.

The term "alkyl", as used in the present disclosure, refers to branched or linear saturated aliphatic monovalent hydrocarbyl groups having a specified number of carbon atoms. The term "alkylene", as used in the present disclosure, refers to branched or linear saturated aliphatic divalent hydrocarbyl groups having a specified number of carbon atoms. $C_{n-m}$ refers to groups with n to m carbon atoms. For example, $C_{2-5}$ alkylene includes $C_2$ alkylene, $C_3$ alkylene, $C_4$ alkylene, and $C_5$ alkylene.

An alkyl (or alkylene) group can be unsubstituted or substituted, where at least one hydrogen is substituted by another chemical group. Unless otherwise specifically defined or indicated, the term "alkyl" (or "alkylene") in the present disclosure includes both unsubstituted and substituted alkyl (or alkylene) groups.

A "therapeutically effective amount" is the amount of a therapeutic agent that, when administered to a patient, can improve the disease or symptoms. A "preventatively effective amount" is the amount of a prophylactic agent that, when administered to a subject, can prevent the disease or symptoms. The amount constituting a "therapeutically effective amount" of a therapeutic agent or a "preventatively effective amount" of a prophylactic agent varies depending on the therapeutic/prophylactic agent, the disease state and its severity, and factors such as the age and weight of the patient to be treated/subject to be prevented. Those skilled in the art can routinely determine the therapeutically effective amount and preventatively effective amount based on their knowledge and the present disclosure.

In the present disclosure, when there is an inconsistency between the name of a compound and its structural formula, the structural formula shall prevail.

It should be understood that the term "compound of the present disclosure" as used herein may include a compound of formula (I), an N-oxide thereof, a solvate thereof, a pharmaceutically acceptable salt thereof, a stereoisomer thereof, or mixtures thereof according to the context.

The term "cationic lipid" as used herein refers to a lipid that is positively charged at a selected pH value.

Cationic lipids readily bind with negatively charged nucleic acids, interacting via electrostatic forces with the negatively charged phosphate groups present in nucleic acids, to form lipid nanoparticles (LNPs). Lipid nanoparticles (LNPs) are currently one of the mainstream delivery vectors.

During the screening of a large number of compounds, the inventors found that it is extremely challenging to identify suitable cationic lipid compounds that meet the following conditions: significantly different from the representative cationic lipid structures in the prior art, while also exhibiting extremely high transfection efficiency, very low cytotoxicity, and high and sustained expression in mice in vivo. The inventors discovered several compounds, such as YK-908, YK-909, YK-910, and YK-912, which, compared with cationic lipids with very different chemical structures in the prior art, can deliver nucleic acids with significantly improved intracellular transfection efficiency, significantly reduced cytotoxicity, and significantly increased expression levels and duration in animals in vivo.

In summary, the present disclosure is at least based on the following findings:

The cationic lipid compounds of the present disclosure can be used to deliver nucleic acid molecules, small molecule compounds, polypeptides, or proteins. Compared with known cationic lipid compounds, the cationic lipid compounds of the present disclosure result in higher transfection efficiency and lower cytotoxicity, with significantly increased expression levels in the spleen of animals, thereby improving delivery efficiency and having significant clinical importance.

1. In the series of cationic lipid compounds designed, including YK-908, YK-909, YK-910, and YK-912, compared with representative cationic lipids in the prior art, some show significant chemical structure differences, such as SM-102, MC3 (Dlin-MC3-DMA), YK-501, YK-506, and HHMA, while some have similar chemical structures, such as compound 7 and I-1.

SM-102 is a cationic lipid compound disclosed by Moderna, Inc. in WO20170409245A2 (page 29 of the specification).

MC3 is a cationic lipid compound disclosed by Alnylam Pharmaceuticals, Inc. in CN102625696B (page 6 of the specification).

YK-501 and YK-506 are cationic lipid compounds disclosed by Beijing Youcare Kechuang Pharmaceutical Technology Co., Ltd. in CN116082275B (page 2 of the specification).

HHMA is a cationic lipid compound disclosed by Suzhou Abogen Biosciences Co., Ltd. in CN112979483B (page 7 of the specification).

Compound 7 is a cationic lipid compound disclosed by Suzhou Abogen Biosciences Co., Ltd. in CN114206827A (page 45 of the specification).

I-1 is a cationic lipid compound disclosed by Acuitas Therapeutics, Inc in CN110799492A (page 19 of the specification).

The chemical structures of representative cationic lipids and structurally similar cationic lipids in the prior art are as follows:

SM-102

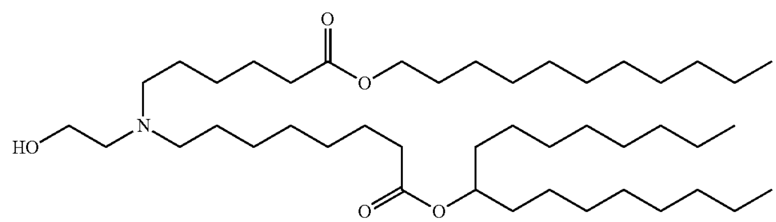

(WO2017049245A2, page 29 of the specification);

YK-501

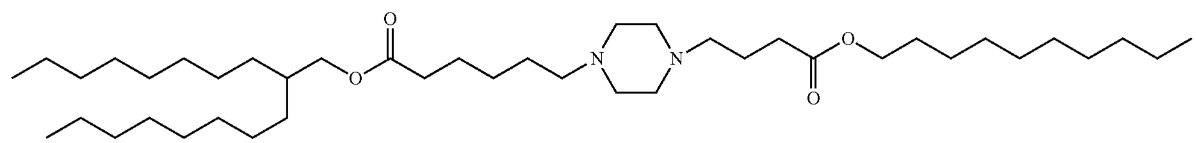

YK-506

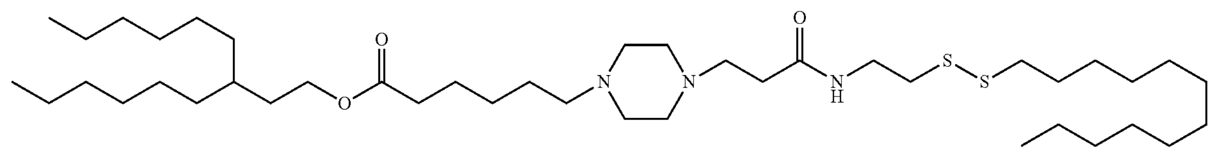

(CN116082275N, page 2 of the specification);

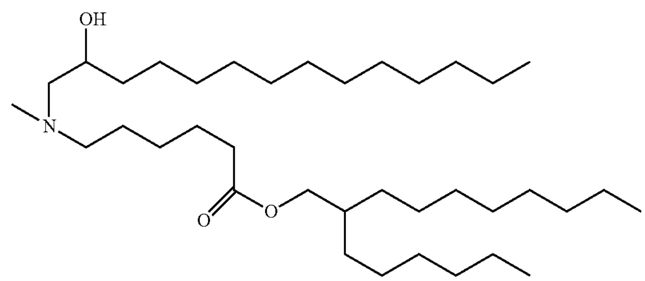

(CN1129794836B, page 12 of the specification);

HHMA

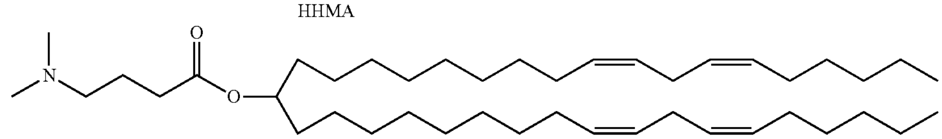

D-Lin-MC3-DMA (CN102625696B, page 6 of the specification);

-continued

7

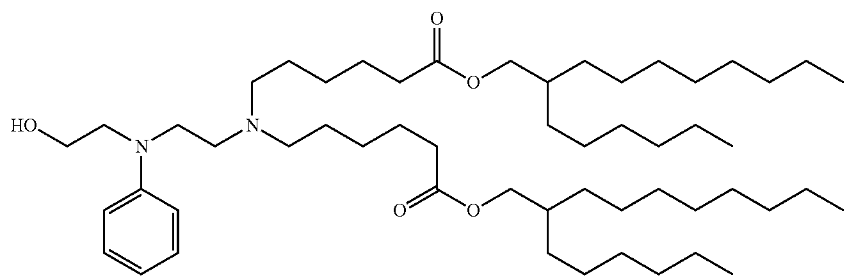

(CN114206827A, page 45 of the specification);

I-1

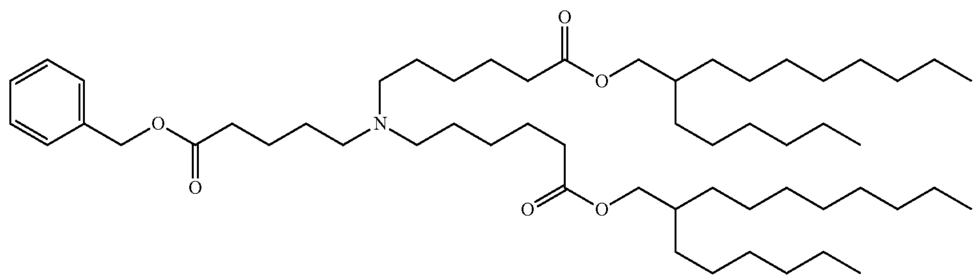

(CN110799492A, page 19 of the specification).

2. In the series of compounds designed in the present disclosure, LNP preparations prepared with YK-908, YK-909, YK-910, and YK-912, compared with representative and structurally similar cationic lipids in the prior art, result in significantly improved cellular transfection efficiency, significantly reduced cytotoxicity, and significantly increased distribution of mRNA and small nucleic acids in the spleen of mice. For example, the cellular transfection efficiency of YK-910 can reach 6.04 times that of SM-102, 186.59 times that of YK-501, 13.19 times that of YK-506, 8.53 times that of HHMA, 90.92 times that of MC3, 33.51 times that of compound 7, 42.56 times that of I-1, and 10.24 times that of Lipofectamine 3000. The cell viability of YK-910 can reach 12% higher than that of SM-102, 31% higher than that of YK-501, 17% higher than that of HHMA, 20% higher than that of MC3, 21% higher than that of compound 7, 26% higher than that of I-1, and 63% higher than that of Lipofectamine 3000. The expression level of mRNA in animals in vivo 24 hours after administration resulting from YK-910 can reach 6.78 times that of SM-102, 12.21 times that of YK-501, 8.28 times that of YK-506, and 11.50 times that of compound 7. The expression level of mRNA in the spleen resulting from YK-910 can reach 9.49 times that of SM-102, 17.04 times that of YK-501, and 3.40 times that of YK-506. The distribution of small nucleic acids in the spleen resulting from YK-910 can reach 51.19 times that of SM-102, 11.91 times that of YK-501, and 2.85 times that of YK-506. Although the fluorescence intensity of YK-912 in the spleen and liver is 1.25 times and 10.82 times that of SM-102, respectively, its distribution in the kidney is significantly reduced, being 0.14 times that of SM-102.

3. In the series of compounds designed in the present disclosure with minimal differences in chemical structure, LNP preparations prepared with YK-908, YK-909, YK-910, and YK-912, compared with other compounds, result in significantly improved cellular transfection efficiency, significantly reduced cytotoxicity, and significantly increased distribution of small nucleic acids in the spleen of mice than direct administration. For example, when delivering mRNA, the cellular transfection efficiency of YK-910 can reach 345.06 times that of YK-903 and 313.25 times that of YK-906, while the cytotoxicity of YK-910 can be 58% lower than that of YK-902. When delivering small nucleic acids, the fluorescence intensity of YK-908, YK-909, YK-910, and YK-912 in the spleen is 100.55 times, 126.85 times, 150.67 times, and 31.80 times that of direct administration, respectively. However, the distribution of small nucleic acids resulting from YK-912 in the kidney is 0.09 times that of direct administration.

4. Through unique design and screening, the present disclosure has identified several compounds, such as YK-908, YK-909, YK-910, and YK-912, which, compared with other structurally similar compounds in the prior art, can result in significantly improved cellular transfection efficiency, significantly reduced cytotoxicity, and significantly increased expression levels in the spleen of animals in vivo, thereby enhancing delivery efficiency and achieving unexpected technical effects.

In summary, through unique design and screening, the present disclosure has discovered several compounds, such as YK-908, YK-909, YK-910, and YK-912. Compared with representative and structurally similar cationic lipids in the prior art, these compounds result in significantly improved cellular transfection efficiency, significantly reduced cytotoxicity, and significantly increased expression levels in the spleen of animals, thereby enhancing delivery efficiency.

Details are as follows:

1. Among the Compounds Designed in the Present Disclosure, Including YK-908, YK-909, YK-910, and YK-912, Compared with Representative Cationic Lipids in the Prior Art, Some Show Large Differences in Chemical Structure, Such as SM-102, MC3, YK-501, YK-506, and HHMA, while Some Show Smaller Differences, Such as Compound 7 and I-1.

Representative cationic lipids in the prior art, such as SM-102, MC3, YK-501, YK-506, HHMA, compound 7, and I-1, are compared with the compounds designed in this series:

1) SM-102, MC3, YK-501, YK-506, and HHMA exhibit significant differences in chemical structure compared with the compounds designed in the present disclosure. From the chemical structural formula, it can be seen that the series of compounds in the present disclosure introduce the structure of 2-amino-2-[2-(4-(alkyl)phenyl)ethyl]-1,3-propanediol, where the amino group is connected to a lipid at the head of ethyl tertiary amine, a linear alkyl group containing ester groups or amide groups, or a branched alkyl group containing ester groups or amide groups. In contrast, SM-102, MC3, YK-501, YK-506, and HHMA do not contain the 2-amino-2-[2-(4-(alkyl)phenyl)ethyl]-1,3-propanediol structure. The amino head structure of SM-102 is a simple ethanolamine structure; the amino head structure of MC3 is a dimethyl tertiary amine structure without a hydroxyl structure; the amino head of YK-501 and YK-506 is a piperazinyl group; the amino head of HHMA is a methyl tertiary amine structure with the hydroxyl group located at the 2-position of the fatty chain, and other groups also show significant differences.

2) Compound 7 and I-1 have chemical structures that are relatively close to the compounds designed in the present disclosure, as both contain a benzene ring structure.

2. In Vitro Cellular Transfection Efficiency is Significantly Improved Compared with Representative Cationic Lipids and Structurally Similar Compounds in the Prior Art.

1) In the series of compounds designed, LNP preparations prepared with YK-908, YK-909, YK-910, and YK-912 result in the highest cellular transfection efficiency. Compared with representative cationic lipids in the prior art (such as SM-102, MC3, YK-501, YK-506, HHMA, compound 7, and I-1), their cellular transfection efficiency is significantly improved. For example, the cellular transfection efficiency of YK-910 can reach 6.04 times that of SM-102, 186.59 times that of YK-501, 13.19 times that of YK-506, 8.53 times that of HHMA, 90.92 times that of MC3, 33.51 times that of compound 7, 42.56 times that of I-1, and 10.24 times that of Lipofectamine 3000.

2) A series of structurally similar compounds, where $X_1$ is CH, $R_1$ is $C_{6-25}$ linear or branched alkyl, $R_2$ is H, $M_1$ is —C(O)O—, $M_2$ is H, $G_1$ is —$CH_2$—, $G_2$ is $C_1$-4 alkylene, and $G_3$ is —H, such as YK-901, YK-902, YK-903, YK-904, YK-905, and YK-911, are compared with YK-912. The structural differences among these compounds are only minor variations in individual groups (Table 1). Cellular transfection results (Table 4 and FIG. 2) show that the activity differences within this series of compounds are very large. The cellular transfection efficiency of YK-912 can reach 131.47 times that of YK-901, 18.35 times that of YK-902, 228.30 times that of YK-903, 45.65 times that of YK-904, 78.83 times that of YK-905, and 4.39 times that of YK-911, indicating that the transfection efficiency is significantly improved.

3) A series of structurally similar compounds, where $X_1$ is CH, $R_1$ is $C_{6-25}$ linear or branched alkyl, $R_2$ is H, $M_1$ is —C(O)NH— or —NHC(O)—, $M_2$ is H, $G_1$ is —$CH_2$—, $G_2$ is $C_{1-4}$ alkylene, and $G_3$ is —H, such as YK-907, are compared with YK-908. The cellular transfection efficiency of YK-908 is significantly improved, reaching 134.49 times that of YK-907.

4) Compared with the structurally similar compound YK-906, where $X_1$ is N, $R_1$ is $C_{10-11}$ linear alkyl, $R_2$ is $C_{15}$ branched alkyl or $C_{18}$ branched alkyl, $M_1$ is —C(O)O—, $M_2$ is —C(O)O—, $G_1$ is $C_2$ alkylene, $G_2$ is $C_{3-4}$ alkylene, and $G_3$ is $C_{5-6}$ alkylene, the cellular transfection efficiency of YK-909 and YK-910 is significantly improved, reaching 246.15 times and 313.25 times that of YK-906, respectively.

3. Cytotoxicity is Significantly Reduced Compared with Representative Cationic Lipids and Structurally Similar Compounds in the Prior Art.

1) In the series of compounds designed in the present disclosure, including YK-908, YK-909, YK-910, and YK-912, compared with representative cationic lipids in the prior art, some show large differences in chemical structure, such as SM-102, MC3, and HHMA, while some show smaller differences, such as compound 7 and I-1. LNP preparations prepared with YK-909 and YK-910 result in the lowest cytotoxicity. Compared with representative cationic lipids in the prior art, their cell viability is significantly improved. For example, the cell viability of YK-910 can be 12% higher than that of SM-102, 31% higher than that of YK-501, 17% higher than that of HHMA, 20% higher than that of MC3, 21% higher than that of compound 7, 26% higher than that of I-1, and 63% higher than that of Lipofectamine 3000. It is impossible to predict the cytotoxicity of LNP preparations based on the structure of the cationic lipid compounds. Whether they are compounds with huge structural differences or similar structures, the toxicity to transfected cells is very likely to vary greatly.

2) A series of structurally similar compounds, where $X_1$ is CH, $R_1$ is $C_{6-25}$ linear or branched alkyl, $R_2$ is H, $M_1$ is —C(O)O—, $M_2$ is H, $G_1$ is —$CH_2$—, $G_2$ is $C_1$-4 alkylene, and $G_3$ is —H, such as YK-901, YK-902, YK-903, YK-904, YK-905, and YK-911 are compared with YK-912. The structural differences among these compounds are only minor variations in individual groups, yet their cytotoxicity differs greatly. Among them, the cell viability of YK-912 is the highest, which is 29% higher than that of YK-901, 51% higher than that of YK-902, 40% higher than that of YK-903, 35% higher than that of YK-904, 36% higher than that of YK-905, and 25% higher than that of YK-911, indicating that the cell viability is significantly improved.

3) A series of structurally similar compounds, where $X_1$ is CH, $R_1$ is $C_{6-25}$ linear or branched alkyl, $R_2$ is H, $M_1$ is —C(O)NH— or —NHC(O)—, $M_2$ is H, $G_1$ is —$CH_2$—, $G_2$ is $C_1$-4 alkylene, and $G_3$ is —H, such as YK-907, are compared with YK-908. The cell viability of YK-908 is significantly improved, being 16% higher than that of YK-907.

4) Compared with the structurally similar compound YK-906, where $X_1$ is N, $R_1$ is $C_{10-11}$ linear alkyl, $R_2$ is $C_{15}$ branched alkyl or $C_{18}$ branched alkyl, $M_1$ is-C(O)O—, $M_2$ is-C(O)O—, $G_1$ is $C_2$ alkylene, $G_2$ is $C_{3-4}$ alkylene, and $G_3$ is $C_{5-6}$ alkylene, the cellular transfection efficiency of YK-909 and YK-910 is significantly improved, being 29% and 31% higher than that of YK-906, respectively.

4. The protein expression and duration of mRNA in mice in vivo are significantly improved compared with representative cationic lipids and structurally similar compounds in the prior art; the expression level of mRNA in the spleen of animals is significantly higher than that of representative cationic lipids in the prior art; the distribution of small nucleic acids in the spleen of animals is significantly increased compared with representative cationic lipids in the prior art and direct administration.

1) LNP preparations prepared with YK-908, YK-909, YK-910, and YK-912 result in the highest mRNA expression levels in mice in vivo and sustained expression compared with representative cationic lipids in the prior art. The expression levels at 6 h, 24 h, 48 h, and 7 d are significantly higher than those of representative cationic lipids in the prior art. For example, data at 24 hours show that the expression level of YK-910 in animals in vivo can reach 6.78 times that of SM-102, 12.21 times that of YK-501, 8.28 times that of YK-506, and 11.50 times that of compound 7.

2) Compared with compound YK-904, which has a similar structure with slight differences in individual groups, LNP preparations prepared with YK-908, YK-909, YK-910, and YK-912 result in the highest mRNA expression intensity and the longest duration in mice in vivo. For example, at 48 hours, the expression level of YK-910 can reach 23.07 times that of YK-904, and at 7 days, it can still reach 26.32 times.

3) LNP preparations prepared with YK-908, YK-909, YK-910, and YK-912 result in significantly increased expression levels of mRNA in the spleen of mice compared with representative cationic lipids in the prior art. For example, YK-908, YK-909, YK-910, and YK-912 result in abundantly expressed in the spleen and the expression levels are 6.59, 8.00, 9.49, and 6.86 times that of SM-102, respectively. LNP preparations containing Fluc-mRNA prepared with all compounds result in very different expression levels in various organs of mice. YK-908, YK-909, YK-910, and YK-912 result in almost exclusive expression in the spleen, with no expression in other organs such as the heart, lung, and kidney, and little or no expression in the liver. SM-102 results in expression in both the liver and spleen, with no expression in the heart, lung, or kidney.

4) LNP preparations prepared with YK-908, YK-909, and YK-910 result in significantly increased distribution of small nucleic acid drugs in the spleen of mice compared with representative cationic lipids in the prior art. For example, the distribution of small nucleic acid resulting from YK-908, YK-909, and YK-910 in the spleen increases significantly, with the fluorescence intensity of YK-908, YK-909, and YK-910 in the spleen being 34.16 times, 43.10 times, and 51.19 times that of SM-102, respectively; 7.95 times, 10.02 times, and 11.91 times that of YK-501, respectively; and 1.90 times, 2.40 times, and 2.85 times that of YK-506, respectively.

Surprisingly, although the fluorescence intensity of YK-912 in the spleen and liver is 1.25 times and 10.82 times that of SM-102, respectively, its distribution in the kidney decreases significantly, being only 0.14 times that of SM-102, indicating its potential for long-lasting delivery of small nucleic acid drugs. The LNP preparations containing Cy5 fluorescently labeled Leqvio, prepared with all compounds, result in significant differences in distribution in different organs of mice. For example, YK-908, YK-909, and YK-910 result in expression in the liver, spleen, and kidney, but result in no expression in other organs, such as the heart, lung, and lymph.

Compared with direct administration, the LNP preparations prepared with YK-908, YK-909, and YK-910 result in significantly increased distribution of small nucleic acid drugs in the spleen of mice. For example, the fluorescence intensities of YK-908, YK-909, and YK-910 in the spleen are 100.55 times, 126.85 times, and 150.67 times that of direct administration, respectively. The distribution of small nucleic acid resulting from YK-912 in the kidney is 0.09 times that of direct administration, further indicating its potential for long-lasting delivery of small nucleic acid drugs.

5) Compared with representative cationic lipids in the prior art, such as SM-102 and compound 7, the liposomes prepared with the compounds we designed result in reduced protein expression in the liver or do not remain in the liver to express the target protein. Therefore, compared with the cationic lipids in the prior art, the LNP preparations prepared from the compounds we designed exhibit reduced liver toxicity or are non-toxic.

The present disclosure provides a novel cationic lipid compound for delivering a therapeutic or prophylactic agent. The cationic lipid compounds of the present disclosure can be used to deliver nucleic acid molecules, small molecule compounds, polypeptides, or proteins. Compared with known cationic lipid compounds, the cationic lipid compounds of the present disclosure exhibit higher transfection efficiency and lower cytotoxicity, improving delivery efficiency and safety.

An aspect of the present disclosure provides a new cationic lipid compound, which is a compound of formula (I)

I

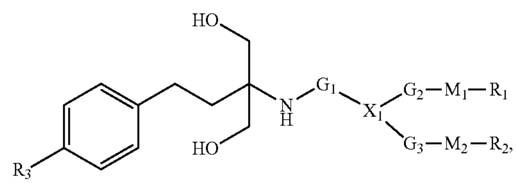

or an N-oxide, a solvate, a pharmaceutically acceptable salt, or a stereoisomer thereof, wherein:

$G_1$ is $C_{1-4}$ alkylene, preferably $C_1$ alkylene or $C_2$ alkylene, more preferably unsubstituted $C_1$ alkylene or unsubstituted $C_2$ alkylene;

$G_2$ is $C_{1-8}$ alkylene, preferably $C_{1-4}$ alkylene, more preferably unsubstituted $C_1$ alkylene, unsubstituted $C_3$ alkylene, or unsubstituted $C_4$ alkylene;

$G_3$ is $C_{2-8}$ alkylene or H, preferably $C_{4-6}$ alkylene or H, more preferably unsubstituted $C_5$ alkylene, unsubstituted $C_6$ alkylene, or H;

$R_1$ is $C_{6-25}$ linear, branched, or substituted alkyl, preferably unsubstituted $C_{8-15}$ linear alkyl or unsubstituted $C_{16-24}$ branched alkyl, more preferably unsubstituted $C_{10-15}$ linear alkyl, or

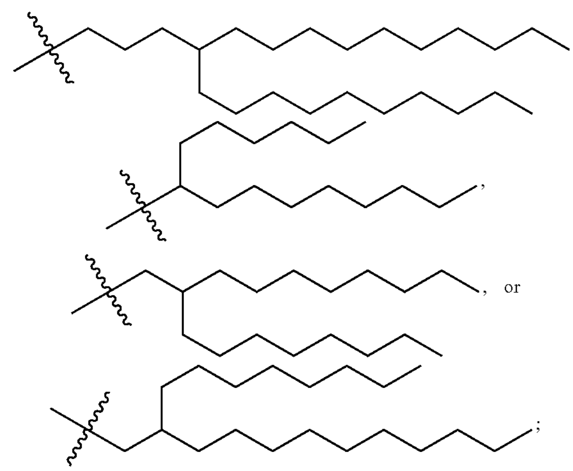

, , or ;

$R_2$ is $C_{6-25}$ linear alkyl, $C_{6-25}$ branched alkyl, $C_{6-25}$ substituted alkyl, or H, preferably unsubstituted $C_{16-22}$ branched alkyl or H, more preferably

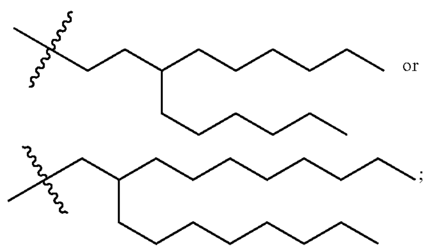

or

;

$R_3$ is $C_{1-25}$ linear alkyl, $C_{1-25}$ branched alkyl, $C_{1-25}$ substituted alkyl, or H, preferably unsubstituted $C_{4-15}$ linear alkyl, more preferably $C_8$ linear alkyl;

$M_1$ is —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, aryl, heteroaryl, or H, preferably —C(O)O—, —C(O)NH—, or —NHC(O)—;

$M_2$ is —C(O)O—, —OC(O)—, —C(O) N(R')—, —N(R')C(O)—, —C(O)—, —C(S)—, —C(S)S—, —SC(S)—, —CH(OH)—, —P(O) (OR')O—, —$S(O)_2$—, —S—S—, aryl, heteroaryl, or H, preferably H or —C(O)O—;

R' is $C_{1-18}$ alkyl, $C_{2-18}$ alkenyl, or H, preferably H;

$X_1$ is —CH— or N.

In one embodiment, $G_1$ is unsubstituted $C_1$ alkylene, for example, —$CH_2$—.

In one embodiment, $G_1$ is unsubstituted $C_2$ alkylene, for example, —$(CH_2)_2$—.

In one embodiment, $G_2$ is unsubstituted $C_1$ alkylene, for example, —$CH_2$—.

In one embodiment, $G_2$ is unsubstituted $C_3$ alkylene, for example, —$(CH_2)_3$—.

In one embodiment, $G_2$ is unsubstituted $C_4$ alkylene, for example, —$(CH_2)_4$—.

In one embodiment, $G_3$ is H, for example, —H.

In one embodiment, $G_3$ is unsubstituted $C_5$ alkylene, for example, —$(CH_2)_5$—.

In one embodiment, $G_3$ is unsubstituted $C_6$ alkylene, for example, —$(CH_2)_6$—.

In one embodiment, $R_1$ is unsubstituted $C_{10}$ linear alkyl, i.e., —$(CH_2)_9CH_3$.

In one embodiment, $R_1$ is unsubstituted $C_{11}$ linear alkyl, i.e., —$(CH_2)_{10}CH_3$.

In one embodiment, $R_1$ is unsubstituted $C_{14}$ linear alkyl, i.e., —$(CH_2)_{13}CH_3$.

In one embodiment, $R_1$ is unsubstituted $C_{24}$ branched alkyl. For example, $R_1$ is

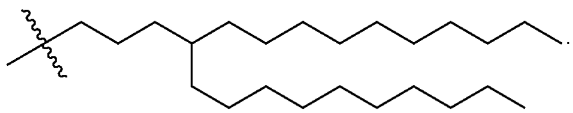 [SMILES: *CCCC(CCCCCCCCCC)CCCCCCCCCC]

.

In one embodiment, $R_1$ is unsubstituted $C_{15}$ branched alkyl. For example, $R_1$ is

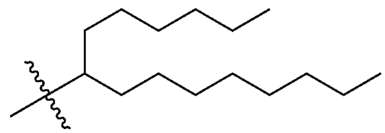

.

In one embodiment, $R_1$ is unsubstituted $C_{18}$ branched alkyl. For example, $R_1$ is

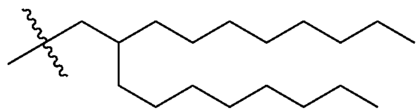

.

In one embodiment, $R_1$ is unsubstituted $C_{22}$ branched alkyl. For example, $R_1$ is

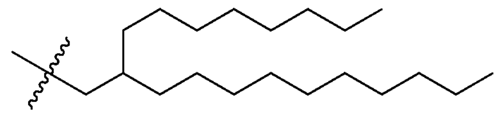

.

In one embodiment, $R_2$ is H.

In one embodiment, $R_2$ is unsubstituted $C_{15}$ branched alkyl. For example, $R_2$ is

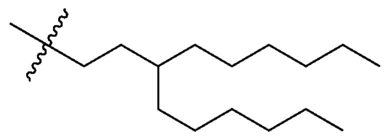

.

In one embodiment, $R_2$ is unsubstituted $C_{18}$ branched alkyl. For example, $R_2$ is

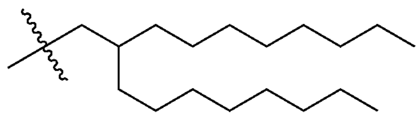

.

In one embodiment, $R_3$ is unsubstituted $C_8$ linear alkyl, i.e., —$(CH_2)$ $7CH_3$.

In one embodiment, $M_1$ is an ester bond. For example, $M_1$ is —C(O)O—.

In one embodiment, $M_1$ is an amide bond. For example, $M_1$ is —C(O)NH— or —NHC(O)—.

In one embodiment, $M_2$ is H.

In one embodiment, $M_2$ is an ester bond. For example, $M_2$ is —C(O)O—.

In one embodiment, $X_1$ is —CH—.

In one embodiment, $X_1$ is N.

In exemplary embodiments, the compound is selected from the compounds as follows, or the N-oxide thereof, the solvate thereof, the pharmaceutically acceptable salt thereof, or the stereoisomer thereof:

TABLE 1
| Structure of compound of formula (I) | Groups of cationic lipid structure | | | | |
|---|---|---|---|---|---|
| | $X_1$ | $R_1$ | $R_2$ | $R_3$ | $M_1$ |
| 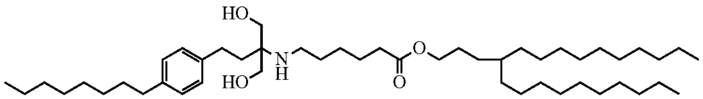 YK-901 | CH | $—(CH_2)_3CH[(CH_2)_9CH_3](CH_2)_9CH_3$ | \ | $—(CH_2)_7CH_3$ | —C(O)O— |
| 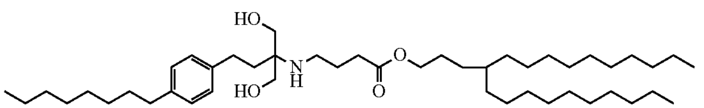 YK-902 | CH | $—(CH_2)_3CH[(CH_2)_9CH_3](CH_2)_9CH_3$ | \ | $—(CH_2)_7CH_3$ | —C(O)O— |
| 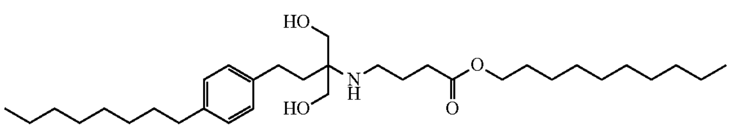 YK-903 | CH | $—(CH_2)_9CH_3$ | \ | $—(CH_2)_7CH_3$ | —C(O)O— |
| 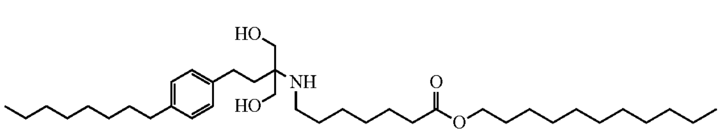 YK-904 | CH | $—(CH_2)_{10}CH_3$ | \ | $—(CH_2)_7CH_3$ | —C(O)O— |
| 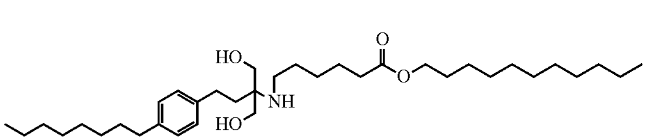 YK-905 | CH | $—(CH_2)_{10}CH_3$ | \ | $—(CH_2)_7CH_3$ | —C(O)O— |

TABLE 1-continued
| Groups of cationic lipid structure | | | | | |
|---|---|---|---|---|---|
| 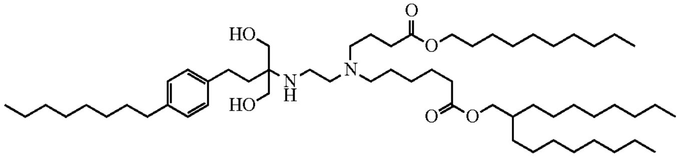 YK-906 | N | $—(CH_2)_9CH_3$ | $—CH_2CH[(CH_2)_7CH_3](CH_2)_7CH_3$ | $—(CH_2)_7CH_3$ | —C(O)O— |
| 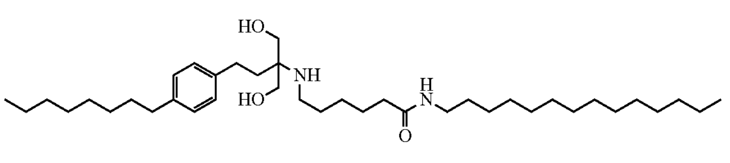 YK-907 | CH | $—(CH_2)_{13}CH_3$ | \ | $—(CH_2)_7CH_3$ | —C(O)NH— |
| 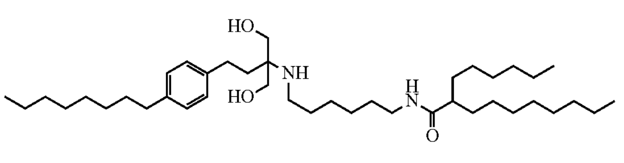 YK-908 | CH | $—CH[(CH_2)_5CH_3](CH_2)_7CH_3$ | \ | $(CH_2)_7CH_3$ | —NHC(O)— |
| 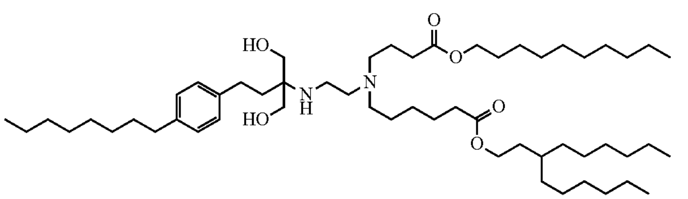 YK-909 | N | $—(CH_2)_9CH_3$ | $—(CH_2)_2CH[(CH_2)_5CH_3](CH_2)_5CH_3$ | $—(CH_2)_7CH_3$ | —C(O)O— |

TABLE 1-continued
| Groups of cationic lipid structure | | | | | |
|---|---|---|---|---|---|
| 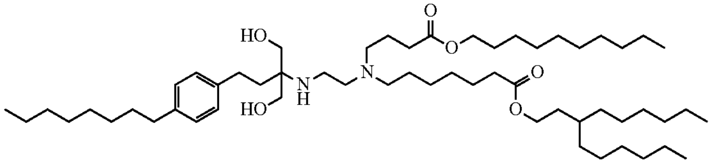<br>YK-910 | N | —$(CH_2)_{10}CH_3$ | —$(CH_2)_2CH[(CH_2)_5CH_3](CH_2)_5CH_3$ | —$(CH_2)_7CH_3$ | —C(O)O— |
| 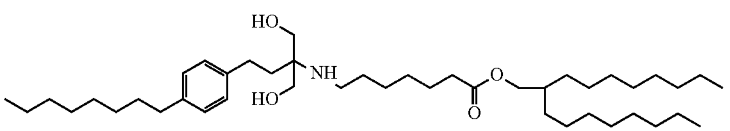<br>YK-911 | CH | —$CH_2CH[(CH_2)_7CH_3](CH_2)_7CH_3$ | \ | —$(CH_2)_7CH_3$ | —C(O)O— |
| 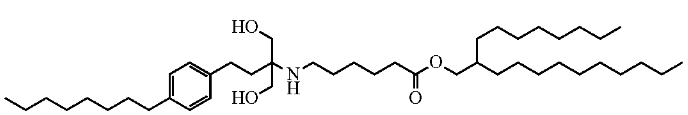<br>YK-912 | CH | —$CH_2CH[(CH_2)_7CH_3](CH_2)_9CH_3$ | \ | —$(CH_2)_7CH_3$ | —C(O)O— |
| Structure of compound of formula (I) | $M_2$ | $G_1$ | $G_2$ | $G_3$ |
|---|---|---|---|---|
| 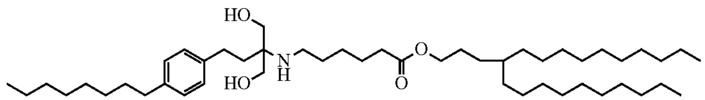<br>YK-901 | \ | —$CH_2$— | —$(CH_2)_3$— | —H |
| 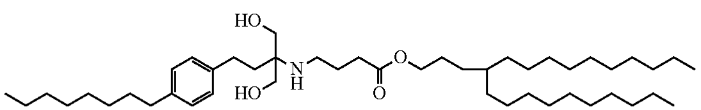<br>YK-902 | \ | —$CH_2$— | —$CH_2$— | —H |

TABLE 1-continued
| Groups of cationic lipid structure | | | | |
|---|---|---|---|---|
| 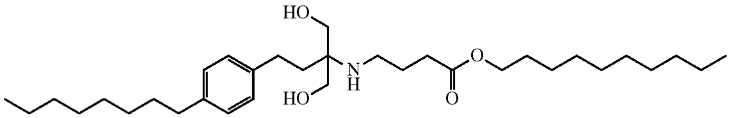 YK-903 | \ | $-CH_2-$ | $-CH_2-$ | $-H$ |
| 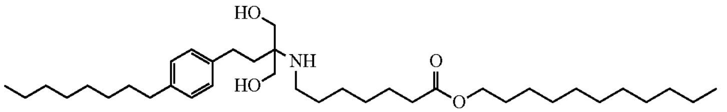 YK-904 | \ | $-CH_2-$ | $-(CH_2)_4-$ | $-H$ |
| 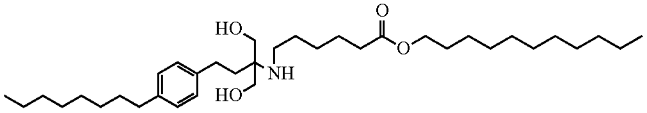 YK-905 | \ | $-CH_2-$ | $-(CH_2)_3-$ | $-H$ |
| 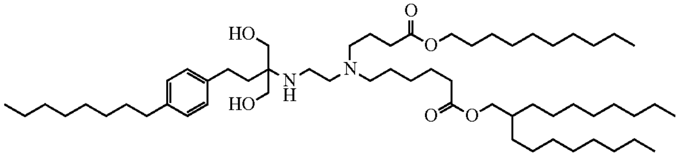 YK-906 | $-C(O)O-$ | $-(CH_2)_2-$ | $-(CH_2)_3-$ | $-(CH_2)_3-$ |
| 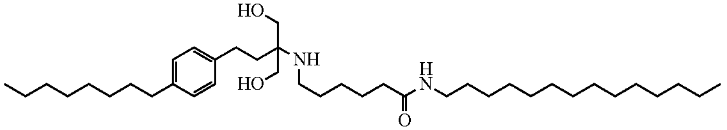 YK-907 | \ | $-CH_2-$ | $-(CH_2)_3-$ | $-H$ |

TABLE 1-continued
| Groups of cationic lipid structure | | | | |
|---|---|---|---|---|
| 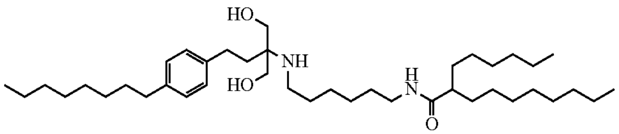<br>YK-908 | \ | —$CH_2$— | —$(CH_2)_4$— | —H |
| 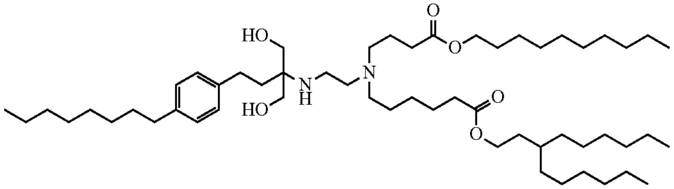<br>YK-909 | —C(O)O— | —$(CH_2)_2$— | —$(CH_2)_3$— | —$(CH_2)_5$— |
| 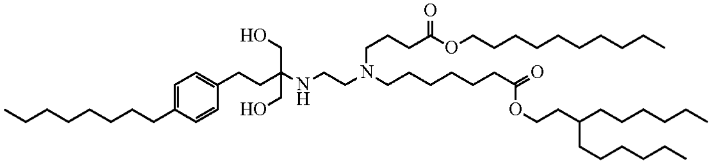<br>YK-910 | —C(O)O— | —$(CH_2)_2$— | —$(CH_2)_3$— | —$(CH_2)_6$— |
| 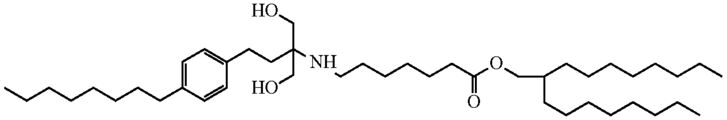<br>YK-911 | \ | —$CH_2$— | —$(CH_2)_4$— | —H |
| 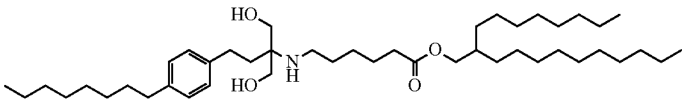<br>YK-912 | \ | —$CH_2$— | —$(CH_2)_3$— | —H |
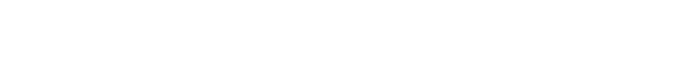

A second aspect of the present disclosure provides a composition comprising a vector, wherein the vector comprises a cationic lipid, and the cationic lipid comprises the compound of formula (I), or the N-oxide thereof, the solvate thereof, the pharmaceutically acceptable salt thereof, or the stereoisomer thereof as described above.

In one embodiment, the composition is a nanoparticle preparation, and the average particle size of the nanoparticle preparation is 10 nm to 300 nm, preferably 90 nm to 260 nm; the polydispersity index of the nanoparticle preparation is ≤50%, preferably ≤40%, more preferably ≤30%.

Cationic Lipids

In one embodiment of the composition/vector of the present disclosure, the cationic lipid is selected from one or more of the above compound of formula (I), the N-oxide thereof, the solvate thereof, the pharmaceutically acceptable salt thereof, or the stereoisomer thereof. In one embodiment, the cationic lipid is selected from the above compound of formula (I). For example, the cationic lipid is compound YK-908, YK-909, YK-910, or YK-912. In one preferred embodiment, the cationic lipid is compound YK-908. In another preferred embodiment, the cationic lipid is compound YK-909. In yet another preferred embodiment, the cationic lipid is compound YK-910. In yet another preferred embodiment, the cationic lipid is compound YK-912.

In another embodiment of the composition/vector of the present disclosure, the cationic lipid includes: (a) one or more selected from the above compound of formula (I), the N-oxide thereof, the solvate thereof, the pharmaceutically acceptable salt thereof, or the stereoisomer thereof; (b) one or more additional ionizable lipid compounds different from (a). The (b) cationic lipid compound may be a commercially available cationic lipid or a cationic lipid compound reported in the literature. For example, the (b) cationic lipid compound may be SM-102 from CN102625696B, DLin-K-$C_2$-DMA from CN102245590B, or compound 1 from CN113039174A.

In one embodiment, the molar ratio of the cationic lipid in the vector is 25% to 75%, for example, 30%, 40%, 50%, 55%, 60%, 65%, or 70%.

The vector may be used for delivering an active ingredient, such as a therapeutic or prophylactic agent. The active ingredient may be encapsulated within or combined with the vector.

For example, the therapeutic or prophylactic agent includes one or more of nucleic acid molecules, small molecule compounds, polypeptides, or proteins. The nucleic acid molecules include, but are not limited to, single-stranded DNA, double-stranded DNA, and RNA. Suitable RNA includes, but is not limited to, small interfering RNA (siRNA), asymmetric interfering RNA (aiRNA), microRNA (miRNA), dicer-substrate RNA (dsRNA), small hairpin RNA (shRNA), messenger RNA (mRNA), and mixtures thereof.

Neutral Lipids

The vector may comprise a neutral lipid. In the present disclosure, the neutral lipid refers to an auxiliary lipid that is uncharged or exists in a zwitterionic form at a selected pH value. The neutral lipid may regulate the fluidity of nanoparticles into a lipid bilayer structure and improve efficiency by promoting lipid phase transition, and may also affect target organ specificity.

In one embodiment, the molar ratio of the cationic lipid to the neutral lipid is about 1:1 to 15:1, for example, about 14:1, 13:1, 12:1, 11:1, 10:1, 9:1, 8:1, 7:1, 6:1, 5:1, 4:1, 3:1, or 2:1. In one preferred embodiment, the molar ratio of the cationic lipid to the neutral lipid is about 5:1 (for example, it may be 4.5:1, 4.6:1, 4.7:1, 4.8:1, 4.9:1, 5:1, or a range between any of the aforementioned values and any intermediate ratio therein).

For example, the neutral lipid may include one or more of phosphatidylcholine, phosphatidylethanolamine, sphingomyelin, ceramide, sterol, or derivatives thereof.

The vector components of a composition containing the cationic lipid may include one or more neutral lipids—phospholipids, such as one or more (poly) unsaturated lipids. The phospholipid can be assembled into one or more lipid bilayers. Generally, the phospholipid may comprise a phospholipid moiety and one or more fatty acid moieties.

The neutral lipid moiety may be selected from the non-limiting group consisting of phosphatidylcholine, phosphatidylethanolamine, phosphatidylglycerol, phosphatidylserine, phosphatidic acid, 2-lysophosphatidylcholine, and sphingomyelin. The fatty acid moiety may be selected from the non-limiting group consisting of lauric acid, myristic acid, myristelaidic acid, palmitic acid, palmitoleic acid, stearic acid, oleic acid, linoleic acid, α-linolenic acid, erucic acid, phytanic acid, arachidic acid, arachidonic acid, eicosapentaenoic acid, behenic acid, docosapentaenoic acid, and docosahexaenoic acid. Also contemplated are non-natural species which include natural species with modifications and substitutions including branching, oxidation, cyclization, and alkynes. For example, the phospholipid can be functionalized with or cross-linked with one or more alkynes (e.g., an alkenyl group in which one or more double bonds are replaced by a triple bond). Under appropriate reaction conditions, alkynyl groups may undergo copper-catalyzed cycloaddition reactions upon exposure to azides. These reactions can be used to functionalize the lipid bilayer of the composition to facilitate membrane penetration or cell recognition, or to couple the composition to useful components such as targeting or imaging moieties (e.g., dyes).

The neutral lipid for use in these compositions may be selected from the non-limiting group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine ($C_{16}$ Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2 diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

In some embodiments, the neutral lipid comprises DSPC. In certain embodiments, the neutral lipid comprises DOPE. In some embodiments, the neutral lipid comprises both DSPC and DOPE.

Structural Lipids

The vector of the composition containing the cationic lipid may further comprise one or more structural lipids. In the present disclosure, the structural lipid refers to a lipid that enhances the stability of nanoparticles by filling the gaps between lipids.

In one embodiment, the molar ratio of the cationic lipid to the structural lipid is about 0.5:1 to 5:1, preferably 0.6:1 to 3:1, for example, about 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

The structural lipid may be selected from, but is not limited to, the group consisting of cholesterol, nonsterol, sitosterol, ergosterol, campesterol, stigmasterol, brassinosterol, tomatidine, ursolic acid, α-tocopherol, corticosteroid, and mixtures thereof. In some embodiments, the structural lipid is cholesterol. In some embodiments, the structural lipid includes cholesterol, corticosteroid (e.g., prednisolone, dexamethasone, prednisone, and hydrocortisone), or a combination thereof.

Polymer-Conjugated Lipids

The vector of the composition containing the cationic lipid may further comprise one or more polymer-conjugated lipids. The polymer-conjugated lipid mainly refers to a lipid modified with polyethylene glycol (PEG). Hydrophilic PEG stabilizes LNPs, regulates nanoparticle size by limiting lipid fusion, and increases nanoparticle half-life by reducing non-specific interactions with macrophages.

In one embodiment, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, or PEG-modified dialkylglycerol. The molecular weight of PEG for the PEG modification is usually 350 to 5000 Da.

For example, the polymer-conjugated lipid is selected from one or more of distearoyl phosphatidylethanolamine polyethylene glycol 2000 (DSPE-PEG2000), dimyristoylglycero-3-methoxypolyethylene glycol 2000 (DMG-PEG2000), or methoxypolyethylene glycol ditetradecylacetamide (ALC-0159).

In one embodiment of the composition/vector of the present disclosure, the polymer-conjugated lipid is DMG-PEG2000.

In one embodiment of the composition/vector of the present disclosure, the vector further comprises a neutral lipid, a structural lipid, and a polymer-conjugated lipid, and the molar ratio of the cationic lipid, the neutral lipid, the structural lipid, and the polymer-conjugated lipid is (25 to 75):(5 to 25):(15 to 65):(0.5 to 10), for example, (30 to 49):(7.5 to 15):(35 to 55):(1 to 5). The molar ratios of the cationic lipid, the neutral lipid, the structural lipid, and the polymer-conjugated lipid add up to 100.

In one embodiment of the composition/vector of the present disclosure, the vector further comprises a neutral lipid, a structural lipid, and a polymer-conjugated lipid, and the molar ratio of the cationic lipid, the neutral lipid, the structural lipid, and the polymer-conjugated lipid is 40:10:48.5:1.5 or 49:10:39.5:1.5, preferably 49:10:39.5:1.5.

Therapeutic and/or Prophylactic Agents

The composition may comprise one or more therapeutic and/or prophylactic agents. In one embodiment, the mass ratio of the vector to the therapeutic or prophylactic agent is 10:1 to 30:1, for example, 12:1, 13:1, 14:1, 15:1, 16:1, 17:1, 18:1, 19:1, 20:1, 21:1, 22:1, 23:1, 24:1, or 25:1.

In one embodiment, the mass ratio of the vector to the therapeutic or prophylactic agent is 12.5:1 to 20:1. For example, it may be 12.5:1, 13:1, 13.5:1, 14:1, 14.5:1, 15:1, 15.5:1, 16:1, 16.5:1, 17:1, 17.5:1, 18:1, 18.5:1, 19:1, 19.5:1, or 20:1, with a preferred ratio of 15:1.

The therapeutic or prophylactic agent includes, but is not limited to, one or more of nucleic acid molecules, small molecule compounds, polypeptides, or proteins.

For example, the therapeutic or prophylactic agent is a vaccine or compound capable of eliciting an immune response.

The vector of the present disclosure can deliver the therapeutic and/or prophylactic agent to mammalian cells or organs. Therefore, the present disclosure further provides a method for treating a disease or condition in a mammal in need thereof. The method comprises administering to the mammal a composition comprising the therapeutic and/or prophylactic agent and/or contacting mammalian cells with the composition.

The therapeutic and/or prophylactic agent comprises a bioactive substance and is alternatively referred to as "active agent". The therapeutic and/or prophylactic agent may be a substance that, after being delivered to cells or organs, cause the desired changes in the cells, organs, or other body tissues or systems. Such substances may be used to treat one or more diseases, conditions, or disorders. In some embodiments, the therapeutic and/or prophylactic agent is a small molecule drug that can be used to treat specific diseases, conditions, or disorders. Examples of the drug that can be used in the composition include, but are not limited to, anti-proliferative agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracycline, alkylating agents, platinum compounds, antimetabolites, and nucleoside analogs such as methotrexate and purine and pyrimidine analogs), anti-infective agents, local anesthetics (e.g., dibucaine and chlorpromazine), β-adrenergic blockers (e.g., propranolol, timolol, and labetalol), antihypertensive agents (e.g., clonidine and hydralazine), antidepressants (e.g., imipramine, amitriptyline, and doxepin), anticonvulsants (e.g., phenytoin), antihistamines (e.g., diphenhydramine, chlorpheniramine, and promethazine), antibiotics/antibacterials (e.g., gentamycin, ciprofloxacin, and cefoxitin), antifungals (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, sedatives, and imaging agents.

In some embodiments, the therapeutic and/or prophylactic agent is a cytotoxin, a radioactive ion, a chemotherapeutic agent, a vaccine, a compound that elicits an immune response, and/or another therapeutic and/or prophylactic agent. The cytotoxin or cytotoxic agent includes any agents harmful to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxy anthracenedione, mitoxantrone, mithramycin, actinomycin D, 1-dehydrotestosterone, glucocorticoids, procaine, tetracaine, lidocaine, propranolol, puromycin, maytansinoids such as maytansinol, rachelmycin (CC-1065), and analogs or homologs thereof. Radioactive ions include, but are not limited to, iodine (e.g., iodine-125 or iodine-131), strontium-89, phosphorus, palladium, cesium, iridium, phosphate, cobalt, yttrium-90, samarium-153, and praseodymium. The vaccine includes compounds and preparations capable of providing immunity against one or more conditions related to infectious diseases such as influenza, measles, human papillomavirus (HPV), rabies, meningitis, whooping cough, tetanus, plague, hepatitis, and pulmonary tuberculosis, and may include mRNA encoding antigens and/or epitopes derived from infectious disease sources. The vaccine may further comprise a compound or preparation that guides an immune response against cancer cells, and may comprise mRNA encoding antigens, epitopes, and/or neoepitopes derived from tumor cells. The compound that elicits an immune response may include vaccines, corticosteroids (e.g., dexamethasone), and other species. In some embodiments, the vaccine and/or compound capable of eliciting an immune response is administered intramuscularly through a composition comprising a compound of formula (I), (IA), (IB), (II), (IIa), (IIb), (IIc), (IId), (IIe), (IIf), (IIg), or (III) (e.g., compound 3, 18, 20, 25, 26, 29, 30, 60, 108 to 112, or 122). The another therapeutic and/or prophylactic agent includes, but is not limited to, antimetabolites (e.g., methotrexate, 6-mercaptopurine, 6-thioguanine, cytarabine, and 5-fluorouracil dacarbazine), alkylating agents (e.g., mechlorethamine, thiotepa, chlorambucil, azithromycin (CC-1065), melphalan, carmustine (BSNU), lomustine (CCNU), cyclophosphamide, busulfan, dibromomannitol, streptozotocin, mitomycin C, cis-diammineplatinum (II) dichloride (DDP), and cisplatin), anthracyclines (e.g., daunorubicin (formerly called daunomycin) and doxorubicin), antibiotics (e.g., dactinomycin (formerly called actinomycin), bleomycin, mithramycin, and anthramycin (AMC)), and antimitotic agents (e.g., vincristine, vinblastine, paclitaxel, and maytansinoids).

In other embodiments, the therapeutic and/or prophylactic agent is a protein. Therapeutic proteins that can be used in the nanoparticles of the present disclosure include, but are not limited to, gentamicin, amikacin, insulin, erythropoietin (EPO), granulocyte colony-stimulating factor (G-CSF), granulocyte-macrophage colony-stimulating factor (GM-CSF), factor VIR, luteinizing hormone-releasing hormone (LHRH) analogs, interferons, heparin, hepatitis B surface antigen, typhoid vaccine, and cholera vaccine.

In some embodiments, the therapeutic agent is a polynucleotide or nucleic acid (e.g., ribonucleic acid or deoxyribonucleic acid). The term "polynucleotide" in its broadest sense includes any compound and/or substance that is an oligonucleotide chain or can be incorporated into an oligonucleotide chain. Exemplary polynucleotides used according to the present disclosure include, but are not limited to, one or more of the following: deoxyribonucleic acid (DNA); ribonucleic acid (RNA), including messenger RNA (mRNA) and its hybrids; RNAi-inducing factors; RNAi factors; siRNA; shRNA; miRNA; antisense RNA; ribozymes; catalytic DNA; RNA inducing triple-stranded helix formation; aptamers, and others. In some embodiments, the therapeutic and/or prophylactic agent is RNA. RNA that can be used in the composition and method described herein may be selected from, but is not limited to, the group consisting of shortmer, antagomir, antisense RNA, ribozymes, small interfering RNA (siRNA), asymmetric interfering RNA (aiRNA), microRNA (miRNA), dicer-substrate RNA (dsRNA), small hairpin RNA (shRNA), transfer RNA (tRNA), messenger RNA (mRNA), and mixtures thereof. In some embodiments, the RNA is mRNA.

In some embodiments, the therapeutic and/or prophylactic agent is mRNA. The mRNA may encode any polypeptide of interest, including any naturally occurring or non-naturally occurring or otherwise modified polypeptide. The polypeptide encoded by the mRNA can be of any size and may have any secondary structure or activity. In some embodiments, the polypeptide encoded by the mRNA may have therapeutic effects when expressed in a cell.

In other embodiments, the therapeutic and/or prophylactic agent is siRNA. siRNA can selectively reduce the expression of a gene of interest or downregulate its expression. For example, the selection of siRNA can result in gene silencing related to a specific disease, condition, or disorder after administering a composition comprising the siRNA to a subject in need thereof. siRNA may comprise a sequence complementary to the mRNA sequence encoding the gene or protein of interest. In some embodiments, siRNA may be immunomodulatory siRNA.

In some embodiments, the therapeutic and/or prophylactic agent is sgRNA and/or cas9 mRNA. sgRNA and/or cas9 mRNA can be used as gene-editing tools. For example, the sgRNA-cas9 complex can affect the mRNA translation of a gene in the cell.

In some embodiments, the therapeutic and/or prophylactic agent is shRNA or its encoding vector or plasmid. shRNA can be produced inside target cells after the appropriate construct is delivered into the nucleus. The constructs and mechanisms related to shRNA are well known in the relevant field.

Diseases or Conditions

The composition/vector of the present disclosure can deliver a therapeutic or prophylactic agent to a subject or patient. The therapeutic or prophylactic agent includes, but is not limited to, one or more of nucleic acid molecules, small molecule compounds, polypeptides, or proteins. Therefore, the composition of the present disclosure can be used for the preparation of nucleic acid drugs, gene vaccines, small molecule drugs, polypeptides, or protein drugs. Due to the variety of the therapeutic or prophylactic agents described above, the composition of the present disclosure can be used to treat or prevent a variety of diseases or conditions.

In one embodiment, the disease or condition is characterized by dysfunctional or abnormal protein or polypeptide activity.

For example, the disease or condition is selected from the group consisting of infectious diseases, cancer and proliferative diseases, genetic diseases, autoimmune diseases, diabetes, neurodegenerative diseases, cardiovascular and renal vascular diseases, and metabolic diseases.

In one embodiment, the infectious diseases are selected from diseases caused by coronaviruses, influenza viruses, or HIV viruses, pediatric pneumonia, rift valley fever, yellow fever, rabies, and various herpes.

Other Components

The composition may comprise one or more components in addition to those described in the previous sections. For example, the composition may include one or more hydrophobic small molecules, such as vitamins (e.g., vitamin A or vitamin E) or sterols.

The composition may further comprise one or more permeability-enhancing molecules, carbohydrates, polymers, surface-modifying agents, or other components. Permeability-enhancing molecules may be, for example, those described in U.S. Patent Application Publication No. 2005/

0222064. Carbohydrates may include simple sugars (e.g., glucose) and polysaccharides (e.g., glycogen and its derivatives and analogs).

Surface-modifying agents may include, but are not limited to, anionic proteins (e.g., bovine serum albumin), surfactants (e.g., cationic surfactants such as dimethyldioctadecyl ammonium bromide), sugars or sugar derivatives (e.g., cyclodextrins), nucleic acids, polymers (e.g., heparin, polyethylene glycol, and poloxamer), mucolytics (e.g., acetylcysteine, *artemisia argyi*, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). Surface-modifying agents may be placed inside and/or on the surface of the nanoparticles in the composition (e.g., through coating, adsorption, covalent linkage, or other methods).

The composition may further comprise one or more functionalized lipids. For example, lipids may be functionalized with alkynyl groups, which, under appropriate reaction conditions, may undergo cycloaddition reactions when exposed to azides. To be precise, the lipid bilayer can be functionalized in this manner with one or more groups that effectively promote membrane permeability, cell recognition, or imaging. The surface of the composition may also be conjugated with one or more useful antibodies. Functional groups and conjugates that can be used for targeted cell delivery, imaging, and membrane permeability are well known in the art.

In addition to these components, the composition may comprise any substances that can used in a pharmaceutical composition. For example, the composition may comprise one or more pharmaceutically acceptable excipients or auxiliary components, such as, but not limited to, one or more solvents, dispersion media, diluents, dispersing aids, suspending aids, granulating aids, disintegrants, fillers, glidants, liquid vehicles, binders, surfactants, isotonic agents, thickeners or emulsifiers, buffers, lubricants, oils, preservatives, flavoring agents, coloring agents, and others. The excipients are, for example, starch, lactose, or dextrin. The pharmaceutically acceptable excipients are well known in the art (see, for example, Remington's The Science and Practice of Pharmacy, 21st Edition, A.R. Gennaro; Lippincott, Williams & Wilkins, Baltimore, MD, 2006).

Examples of diluents may include, but are not limited to, calcium carbonate, sodium carbonate, calcium phosphate, dicalcium phosphate, calcium sulfate, calcium hydrogen phosphate, sodium phosphate, lactose, sucrose, cellulose, microcrystalline cellulose, kaolin, mannitol, sorbitol, inositol, sodium chloride, dried starch, corn starch, powdered sugar, and/or combinations thereof.

In some embodiments, the composition comprising one or more lipids described herein may further comprise one or more adjuvants, for example, glucopyranosyl lipid adjuvant (GLA), CpG oligodeoxynucleotides (e.g., class A or class B), poly(I:C), aluminum hydroxide, and Pam3CSK4.

The composition of the present disclosure may be prepared in the form of solid, semi-solid, liquid, or gaseous preparations, for example, tablets, capsules, ointments, elixirs, syrups, solutions, emulsions, suspensions, injections, or aerosols. The composition of the present disclosure can be prepared with methods well known in the pharmaceutical field. For example, sterile injectable solutions can be prepared by incorporating the required amount of the therapeutic or prophylactic agent with various other components into a suitable solvent, such as sterile distilled water, followed by sterilization via filtration. Surfactants may also be added to facilitate the formation of a uniform solution or suspension.

For example, the composition of the present disclosure may be administered intravenously, intramuscularly, intradermally, subcutaneously, intranasally, or by inhalation. In one embodiment, the composition is administered subcutaneously.

The composition is administered in a therapeutically effective amount, and the amount may vary depending on the specific agent selected, the route of administration, the nature of the disease being treated, and the age and condition of the patient, and may ultimately be determined by the attending physician or clinician. For example, the therapeutic or prophylactic agent may be administered to a subject (preferably a mammal, such as a human) in a dose of about 0.001 mg/kg to about 10 mg/kg.

EXAMPLES

The present disclosure is further described below in conjunction with examples. However, the present disclosure is not limited to the following examples. The implementation conditions adopted in the examples may be further adjusted based on different requirements of specific use, and any conditions not specifically indicated are conventional conditions in the art. In the specific examples of the present disclosure, all raw materials used are commercially available. Unless otherwise indicated, percentages in the context refer to weight percentages, and all temperatures are given in degrees Celsius. The technical features involved in the various embodiments of the present disclosure may be combined with each other as long as there is no conflict.

The following abbreviations represent the following reagents:

DCM: dichloromethane; EDCI: 1-(3-dimethylaminopropyl)-3-ethylcarbodiimide hydrochloride; DMAP: 4-dimethylaminopyridine; DIEA: N,N-diisopropylethylamine; CAN: acetonitrile; TsOH: p-toluenesulfonic acid; rt: room temperature.

Example 1: Synthesis of cationic lipid compound

1. Synthesis of YK-901

The synthesis route is as follows:

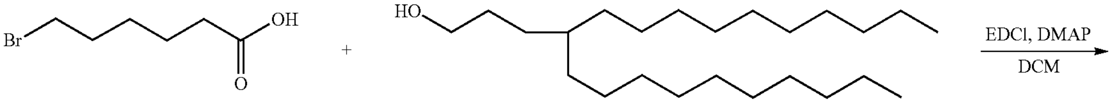

-continued

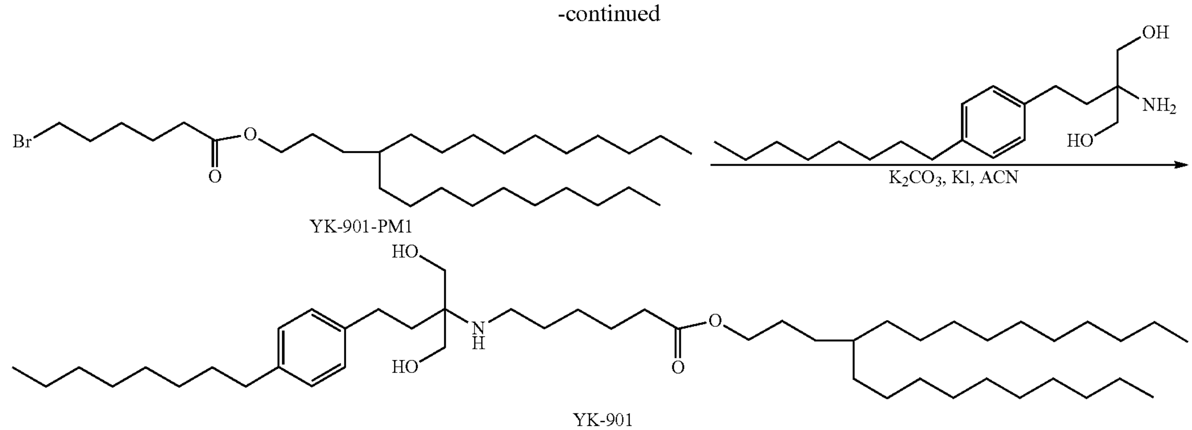

YK-901-PM1

YK-901

Step 1: Synthesis of 4-decyltetradecyl 6-bromohexanoate (YK-901-PM1)

6-Bromohexanoic acid (280 mg, 1.44 mmol) and 4-decyltetradecan-1-ol (510 mg, 1.44 mmol) were dissolved in dichloromethane (10 mL). 1-Ethyl-(3-dimethylaminopropyl) carbodiimide hydrochloride (413 mg, 3.92 mmol) and 4-dimethylaminopyridine (18 mg, 0.26 mmol) were sequentially added to the above mixture. The reaction mixture was stirred and reacted at room temperature overnight. After the reaction was completed, the solvent was removed under reduced pressure, and the residue was purified by silica gel flash chromatography (ethyl acetate/n-hexane) to obtain YK-901-PM1 (550 mg, 1.03 mmol, 71.8%).

Step 2: Synthesis of 4-decyltetradecyl 6-((1-hydroxy-2-(hydroxymethyl)-4-(4-octylphenyl) butan-2-yl)amino) hexanoate (YK-901)

YK-901-PM1 (261 mg, 0.49 mmol) and 2-amino-2-[2-(4-octylphenyl)ethyl]-1,3-propanediol (100 mg, 0.33 mmol) were dissolved in acetonitrile (1.5 mL). Potassium carbonate (135 mg, 0.96 mmol) and potassium iodide (11 mg, 0.064 mmol) were added to the above mixture, and the reaction mixture was stirred at 70° C. for 12 hours. After the reaction was completed, the solid was removed by filtration, and the filtrate was distilled under reduced pressure. The residue was purified by silica gel flash chromatography (methanol/dichloromethane) to obtain YK-901 (100 mg, 0.13 mmol, 40.0%). $C_{49}H_{91}NO_4$, MS(ES): m/z $(M+H^+)$ 758.7.

$^1H$ NMR (400 MHz, $CDCl_3$) δ 7.13 (s, 4H), 4.10-4.00 (m, 4H), 3.93 (d, J=12.5 Hz, 2H), 3.04-2.96 (m, 2H), 2.74-2.65 (m, 2H), 2.63-2.54 (m, 2H), 2.35 (t, J=7.3 Hz, 2H), 2.01-1.87 (m, 4H), 1.75-1.55 (m, 6H), 1.50-1.41 (m, 2H), 1.40-1.20 (m, 50H), 0.91 (t, J=6.6 Hz, 9H).

2. Synthesis of YK-902

The synthesis route is as follows:

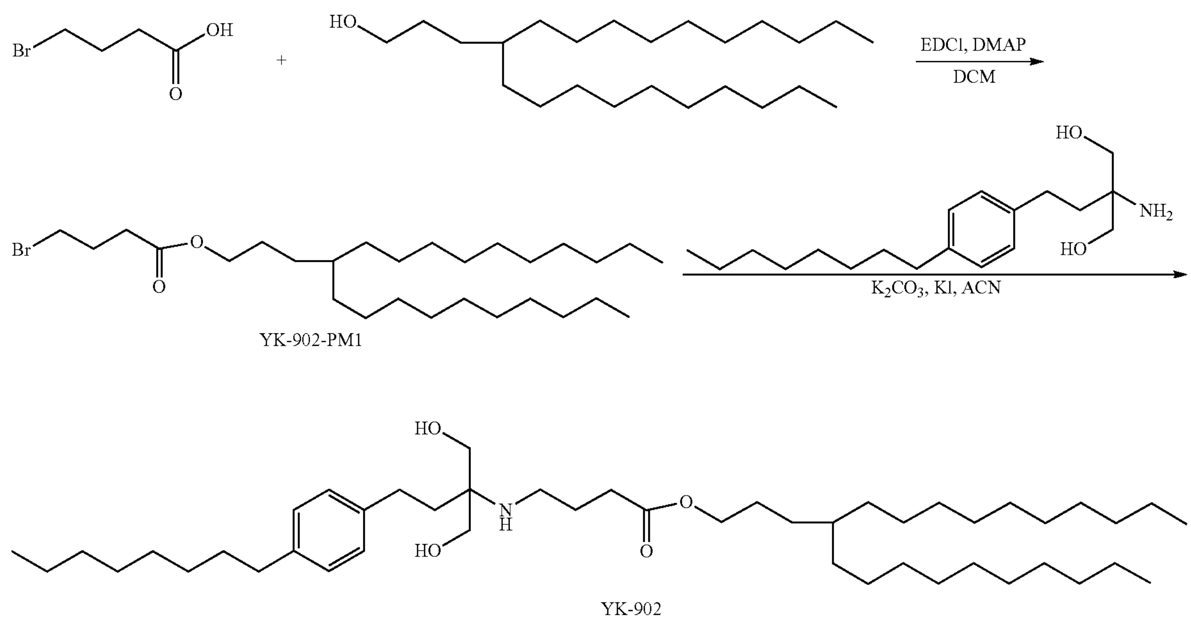

YK-902-PM1

YK-902

Step 1: Synthesis of 4-decyltetradecyl 4-bromobutanoate (YK-902-PM1)

Using 4-bromobutyric acid (612 mg, 3.66 mmol) and 4-decyltetradecan-1-ol (1.3 g, 3.66 mmol) as starting materials, YK-902-PM1 (1.5 g, 2.98 mmol, 81.4%) was obtained following the synthesis method of YK-901-PM1.

Step 2: Synthesis of 4-decyltetradecyl 4-((1-hydroxy-2-(hydroxymethyl)-4-(4-octylphenyl) butan-2-yl)amino) butanoate (YK-902)

Using YK-902-PM1 (196 mg, 0.39 mmol) and 2-amino-2-[2-(4-octylphenyl)ethyl]-1,3-propanediol (100 mg, 0.33 mmol) as starting materials, YK-902 (60 mg, 0.08 mmol, 24.9%) was obtained following the synthesis method of YK-901. $C_{47}H_{87}NO_4$, MS(ES): m/z (M+H$^+$) 730.6. $^1$H NMR (400 MHZ, $CDCl_3$) δ 7.12 (s, 4H), 4.13-4.03 (m, 2H), 3.76 (pd, J=11.9, 6.8 Hz, 4H), 3.52 (s, 4H), 2.91 (t, J=6.8 Hz, 2H), 2.70-2.54 (m, 4H), 2.50 (q, J=7.1 Hz, 2H), 2.13-1.99 (m, 2H), 1.82 (dd, J=10.2, 6.8 Hz, 2H), 1.60 (d, J=6.8 Hz, 4H), 1.28 (d, J=15.1 Hz, 46H), 0.91 (t, J=6.5 Hz, 9H).

3. Synthesis of YK-903

The synthesis route is as follows:

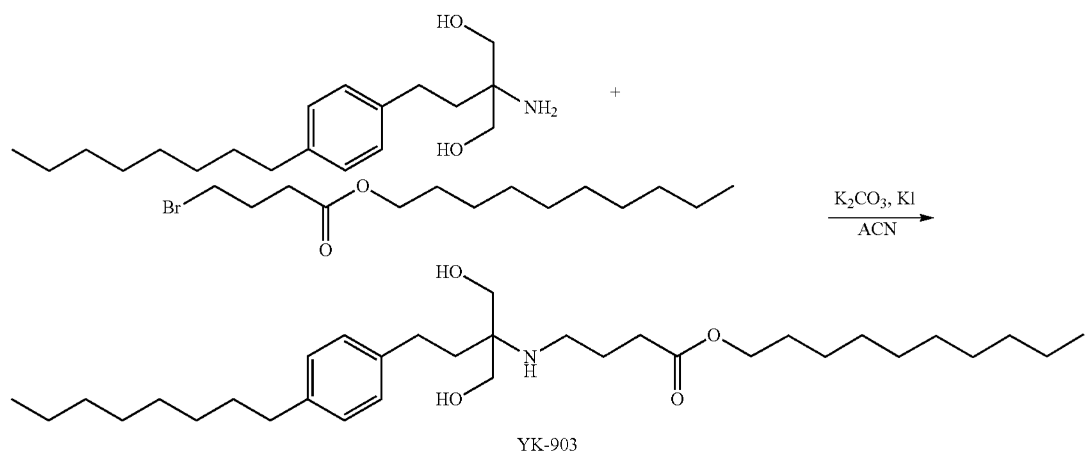

YK-903

Synthesis of decyl 4-((1-hydroxy-2-(hydroxymethyl)-4-(4-octylphenyl) butan-2-yl)amino) butanoate (YK-903)

Using decyl 4-bromobutyrate (200 mg, 0.65 mmol) and 2-amino-2-(4-octylphenethyl)-1,3-propanediol (100 mg, 0.33 mmol) as starting materials, YK-903 (85 mg, 0.16 mmol, 48.2%) was obtained following the synthesis method of YK-901. $C_{33}H_{59}NO_4$, MS(ES): 534.45 m/z (M+H$^+$). $^1$H NMR (400 MHZ, $CDCl_3$) δ 7.09 (s, 4H), 4.04-4.10 (m, 2H), 3.59-3.66 (m, 2H), 2.69 (t, J=6.8 Hz, 2H), 2.56 (d, J=32.0 Hz, 6H), 2.43 (t, J=7.2 Hz, 2H), 1.86 (s, 2H), 1.68 (d, J=17.2 Hz, 2H), 1.59 (d, J=27.2 Hz, 4H), 1.43-1.15 (m, 25H), 0.88 (t, J=6.4 Hz, 6H).

4. Synthesis of YK-904

The synthesis route is as follows:

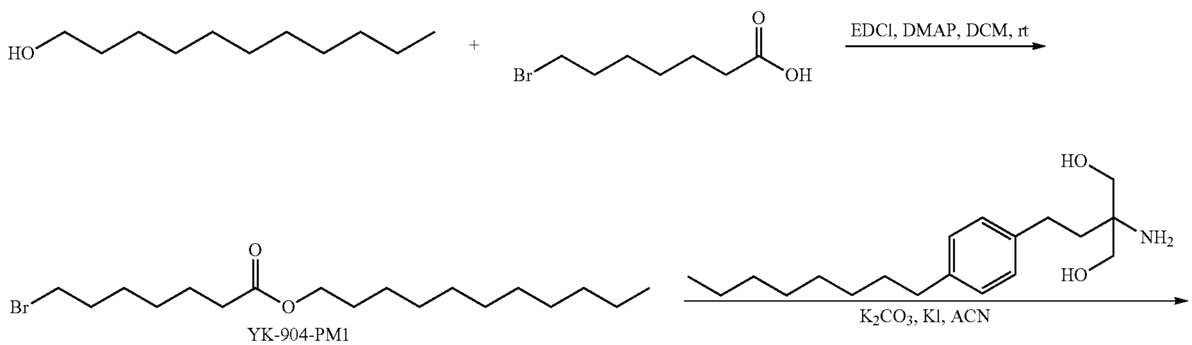

YK-904-PM1

-continued

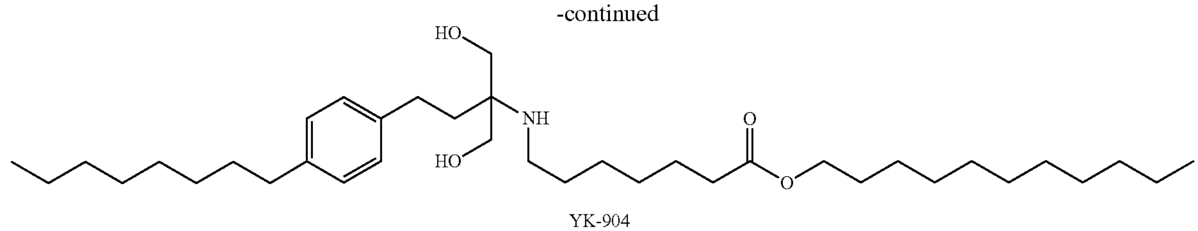

YK-904

Step 1: Synthesis of undecyl 7-bromoheptanoate (YK-904-PM1)

Using 7-bromoheptanoic acid (728 mg, 3.48 mmol) and undecanol (500 mg, 2.90 mmol) as starting materials, YK-904-PMI (900 mg, 2.48 mmol, 85.4%) was obtained following the synthesis method of YK-901-PM1.

Step 2: Synthesis of undecyl 7-((1-hydroxy-2-(hydroxymethyl)-4-(4-octylphenyl) butan-2-yl)amino) heptanoate (YK-904)

Using YK-904-PM1 (182 mg, 0.50 mmol) and 2-amino-2-[2-(4-octylphenyl)ethyl]-1,3-propanediol (100 mg, 0.33 mmol) as starting materials, YK-904 (90 mg, 0.15 mmol, 46.2%) was obtained following the synthesis method of YK-901. $C_{37}H_{67}NO_4$, MS(ES): m/z ($M+H^+$) 590.55. $^1H$ NMR (400 MHZ, $CDCl_3$) δ 7.08 (s, 4H), 4.05-4.02 (m, 4H), δ 3.76-3.70 (m, 4H), 2.72-2.70 (m, 2H), 2.60-2.53 (m, 4H), 2.30-2.27 (m, 2H), 1.75-1.70 (m, 2H), 1.65-1.60 (m, 8H), 1.30-1.25 (m, 31H), 0.89-0.85 (m, 6H).

5. Synthesis of YK-905

The synthesis route is as follows:

Step 1: Synthesis of undecyl 6-bromohexanoate (YK-905-PM1)

Using 6-bromohexanoic acid (3.00 g, 15.38 mmol) and undecanol (2.66 g, 15.44 mmol) as starting materials, YK-905-PM1 (3.20 g, 9.16 mmol, 59.6%) was obtained following the synthesis method of YK-901-PM1.

Step 2: Synthesis of undecyl 6-((1-hydroxy-2-(hydroxymethyl)-4-(4-octylphenyl) butan-2-yl)amino) hexanoate (YK-905)

Using YK-905-PM1 (453 mg, 1.30 mmol) and 2-amino-2-(2-(4-octylphenyl)ethyl)-1,3-propanediol (200 mg, 0.65 mmol) as starting materials, YK-905 (130 mg, 0.23 mmol, 34.7%) was obtained following the synthesis method of YK-901. $C_{36}H_{65}NO_4$, MS(ES): m/z ($M+H^+$) 576.5. $^1H$ NMR (400 MHZ, $CDCl_3$) δ 7.09 (s, 4H), 4.05 (t, J=6.8 Hz, 2H), 3.67 (s, 3H), 2.76-2.44 (m, 8H), 2.31 (t, J=6.4 Hz, 2H), 1.79-1.51 (m, 10H), 1.48-1.07 (m, 28H), 0.95-0.83 (m, 6H).

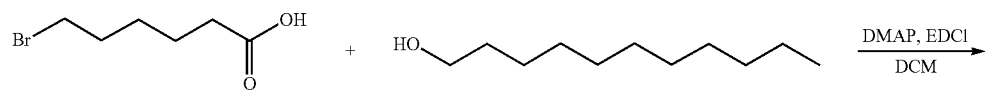

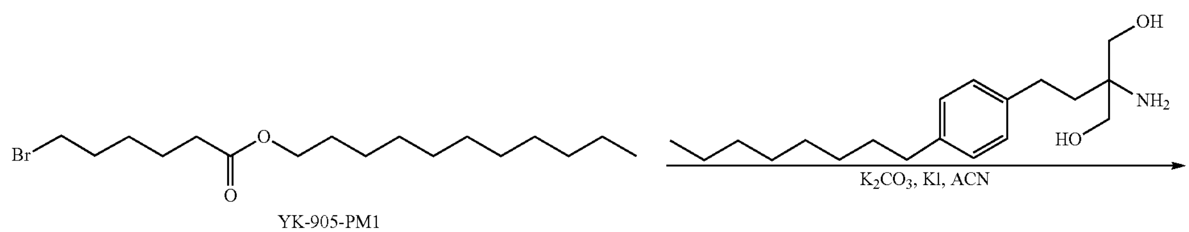

YK-905-PM1

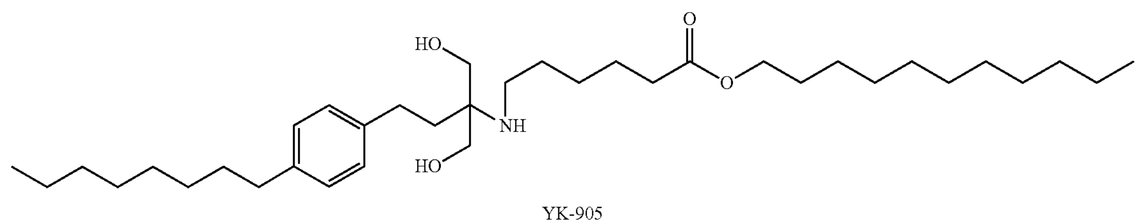

YK-905

6. Synthesis of YK-906

The synthesis route is as follows:

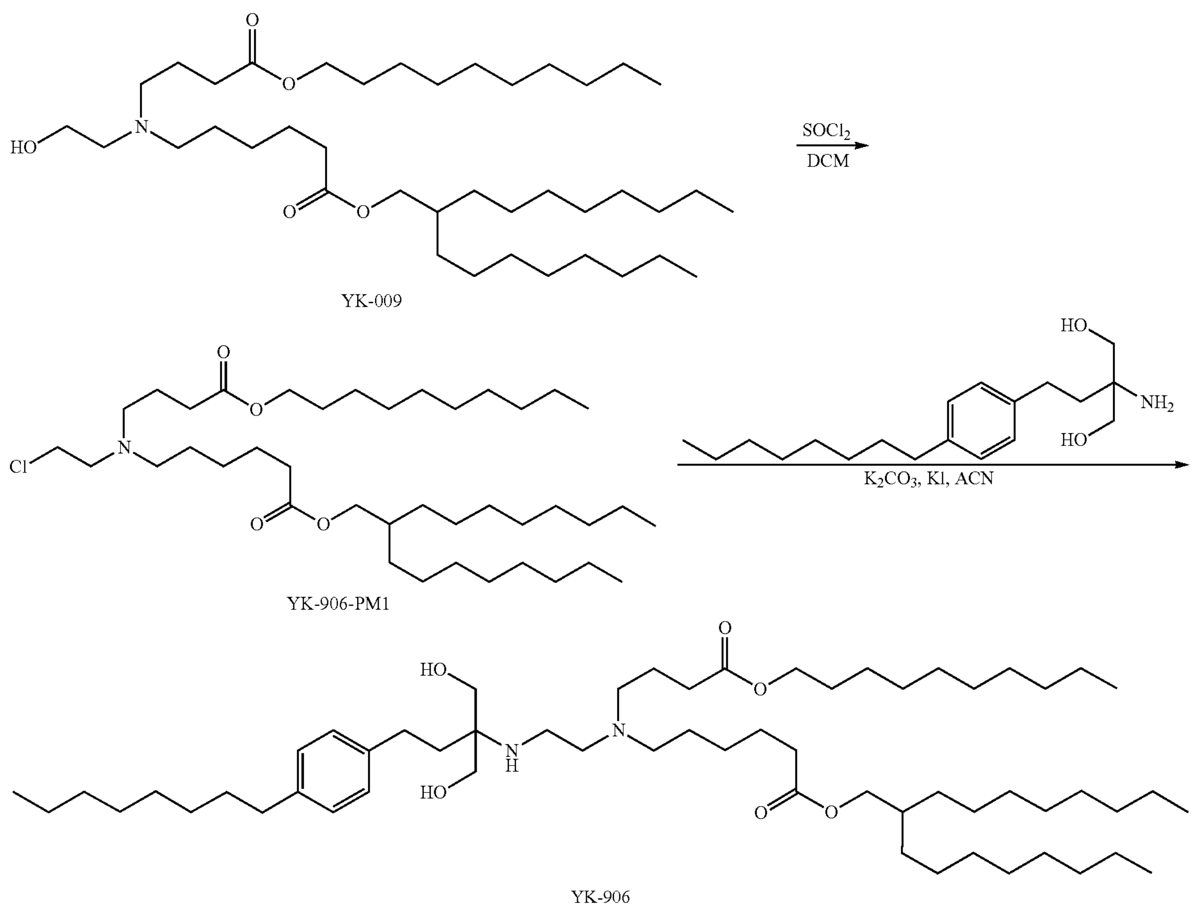

YK-009

YK-906-PM1

YK-906

Step 1: Synthesis of 2-octyldecyl 6-((2-chloroethyl) (4-(decyloxy)-4-oxobutyl)amino) hexanoate (YK-906-PM1)

YK-009 (600 mg, 0.92 mmol, synthesis method detailed in CN114044741B) was dissolved in dichloromethane (6 mL). The system was cooled to 0° C., and thionyl chloride (220 mg, 1.83 mmol) was added dropwise at 0° C. After the dropwise addition was completed, the temperature was raised to room temperature, and the reaction was carried out for 3 hours at room temperature. The mixture was rotary evaporated to dryness under reduced pressure to obtain YK-906-PM1 (600 mg, 0.89 mmol, 97.3%).

Step 2: Synthesis of 2-octyldecyl 6-((4-(decyloxy)-4-oxobutyl) (2-((1-hydroxy-2-(hydroxymethyl)-4-(4-octylphenyl) butan-2-yl)amino)ethyl)amino) hexanoate (YK-906)

YK-906-PM1 (600 mg, 0.89 mmol), 2-amino-2-[2-(4-octylphenyl)ethyl]-1,3-propanediol (200 mg, 0.65 mmol), potassium iodide (11 mg, 0.07 mmol), and potassium carbonate (270 mg, 1.95 mmol) were added to acetonitrile (2 mL). The mixture was stirred at 80° C. for 7 hours. The reaction system was cooled to room temperature and the mixture was filtered. The filtrate was distilled under reduced pressure. The residue was purified by silica gel flash chromatography (0-10% methanol/dichloromethane) to obtain YK-906 (200 mg, 0.21 mmol, 32.6%). $C_{59}H_{110}N_2O_6$, MS(ES): m/z ($M+H^+$) 943.8. $^1H$ NMR (400 MHZ, $CDCl_3$) δ 7.09 (s, 4H), 4.06-4.02 (m, 4H), 3.94-3.91 (m, 4H), 2.72-2.52 (m, 4H), 2.36-2.27 (m, 4H), 1.93-1.58 (m, 8H), 1.64-1.26 (m, 68H), 0.88 (t, J=6.4 Hz, 12H).

7. Synthesis of YK-907

The synthesis route is as follows:

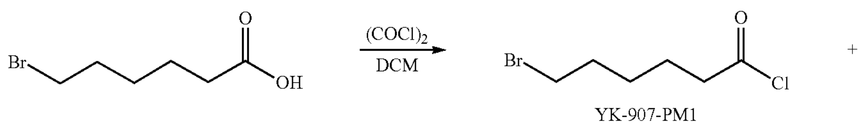

YK-907-PM1

+

-continued

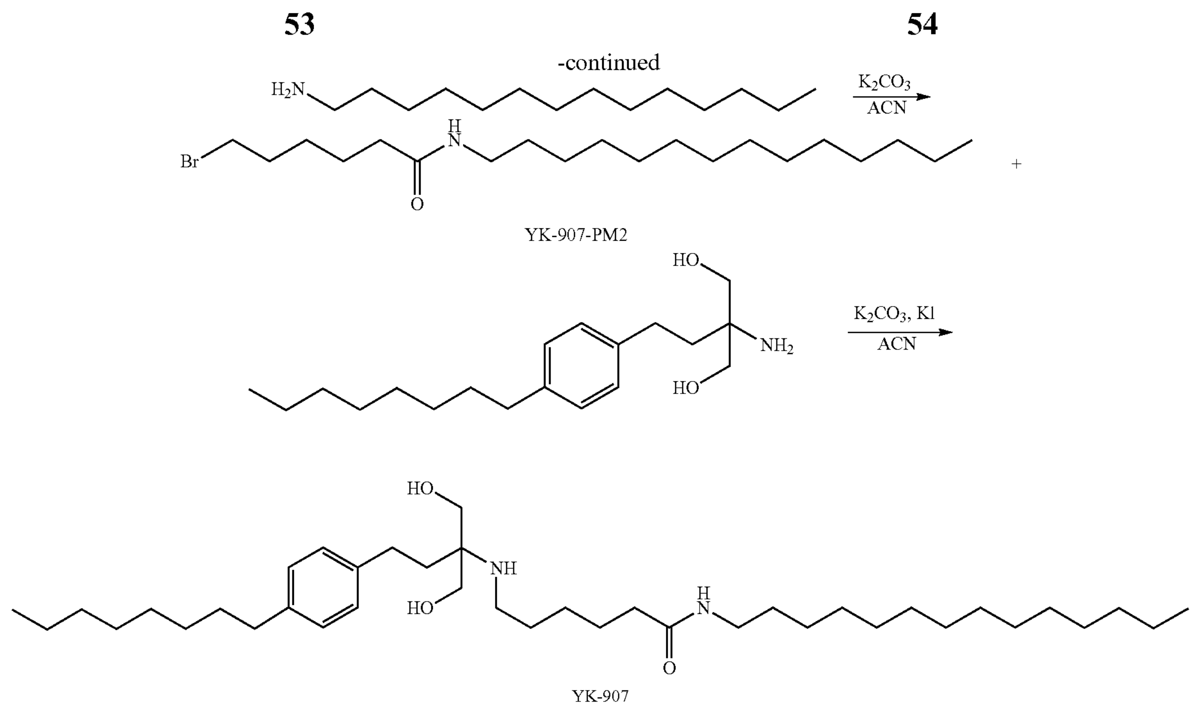

YK-907-PM2

YK-907

Step 1: Synthesis of 6-bromohexanoyl chloride (YK-907-PM1)

6-Bromohexanoic acid (1.0 g, 5.13 mmol) was dissolved in dichloromethane (3 mL), and oxalyl chloride (976 mg, 7.69 mmol) was added to the mixture under an ice bath. The mixture was stirred and reacted at room temperature overnight. After the reaction was completed, the solvent was removed under reduced pressure, thus obtaining YK-907-PM1 (1.08 g, 5.06 mmol, 98.6%).

Step 2: Synthesis of 6-bromo-N-tetradecylhexanamide (YK-907-PM2)

YK-907-PM1 (1.08 g, 5.06 mmol) and tetradecylamine (1.09 g, 5.11 mmol) were dissolved in acetonitrile (8 mL). Potassium carbonate (2.12 g, 15.30 mmol) was added to the above mixture, and the mixture was stirred and reacted at room temperature for 4 hours. After the reaction was completed, the reaction mixture was filtered under reduced pressure to remove solids. The filtrate was rotary evaporated to dryness under reduced pressure. The residue was purified by silica gel chromatography (ethyl acetate/n-hexane) to obtain YK-907-PM2 (650 mg, 1.66 mmol, 32.9%).

Step 3: Synthesis of 6-((1-hydroxy-2-(hydroxymethyl)-4-(4-octylphenyl) butan-2-yl)amino)-N-tetradecylhexanamide (YK-907)

Using YK-907-PM2 (190 mg, 0.49 mmol) and 2-amino-2-[2-(4-octylphenyl)ethyl]-1,3-propanediol (100 mg, 0.33 mmol) as starting materials, YK-907 (66 mg, 0.11 mmol, 32.4%) was obtained following the synthesis method of YK-901. $C_{39}H_{72}N_2O_3$, MS(ES): m/z ($M+H^+$) 617.6. $^1H$ NMR (400 MHZ, $CDCl_3$) δ 7.13 (s, 4H), 3.73 (s, 4H), 3.23-3.20 (m, 2H), 2.80-2.69 (m, 2H), 2.66-2.49 (m, 4H), 2.27-2.15 (m, 2H), 1.80-1.17 (m, 44H), 0.96-0.82 (m, 6H).

8. Synthesis of YK-908

The synthesis route is as follows:

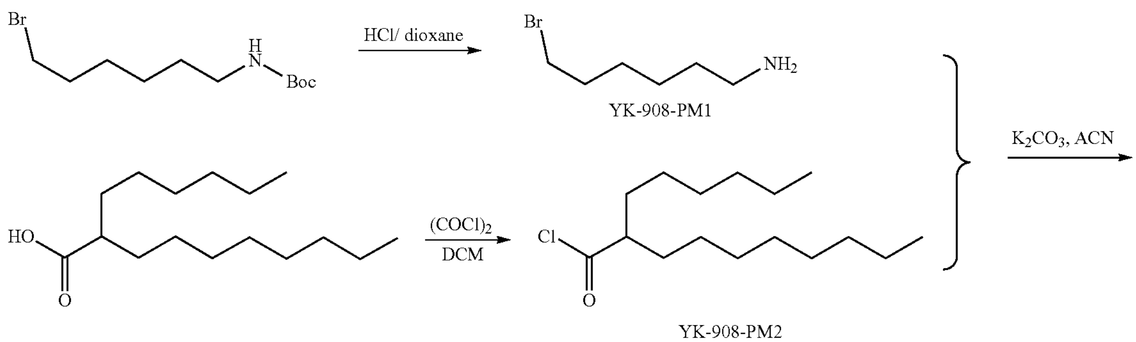

YK-908-PM1

YK-908-PM2

-continued

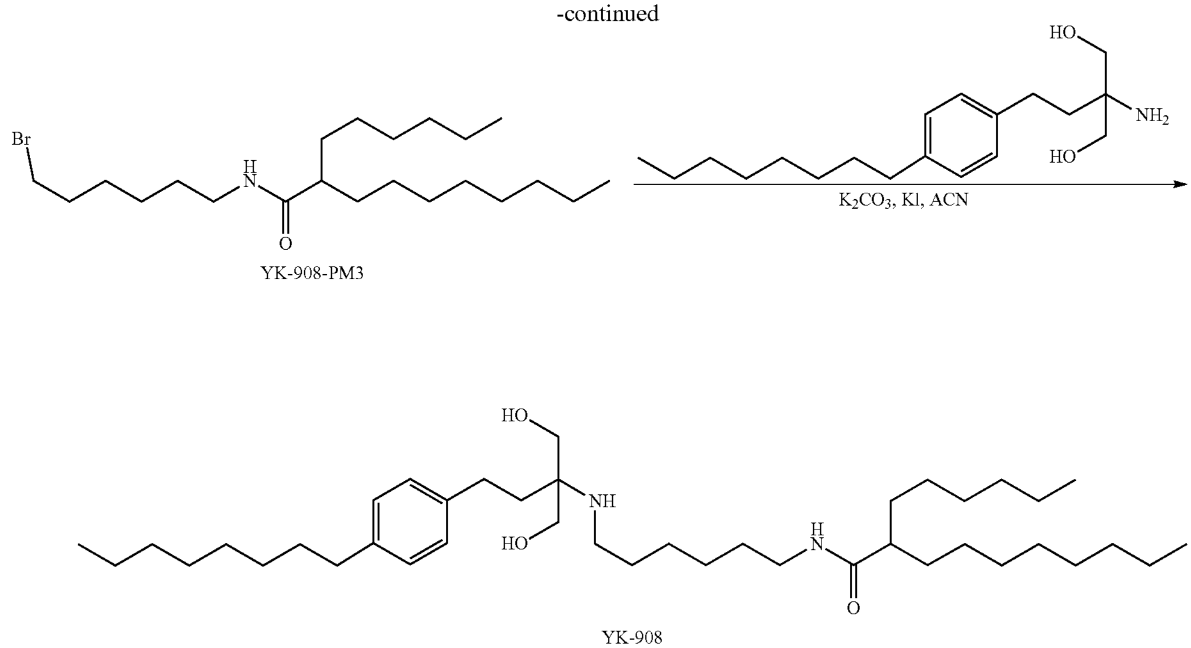

YK-908-PM3

YK-908

Step 1: Synthesis of 6-bromohexylamine (YK-908-PM1)

tert-Butyl (6-bromohexyl) carbamate (500 mg, 1.78 mmol) was dissolved in HCl/dioxane (4M, 2 mL), and the mixture was stirred and reacted at room temperature overnight. After the reaction was completed, the solvent was removed by rotary evaporation, thus obtaining YK-908-PM1 (320 mg, 1.78 mmol, 100%).

Step 2: Synthesis of 2-hexyldecanoyl chloride (YK-908-PM2)

2-Hexyldecanoic acid (456 mg, 1.78 mmol) was dissolved in dichloromethane (2 mL), and oxalyl chloride (270 mg, 2.14 mmol) and N,N-dimethylformamide (0.05 mL) were sequentially added to the above mixture under an ice bath. The mixture was stirred and reacted at room temperature overnight. After the reaction was completed, the solvent was removed under reduced pressure, thus obtaining YK-908-PM2 (489 mg, 1.78 mmol, 100%).

Step 3: Synthesis of N-(6-bromohexyl)-2-hexyldecanamide (YK-908-PM3)

Using YK-908-PM1 (320 mg, 1.78 mmol) and YK-908-PM2 (489 mg, 1.78 mmol) as starting materials, YK-908-PM3 (60 mg, 0.14 mmol, 8.1%) was obtained following the synthesis method of YK-907-PM2.

Step 4: Synthesis of 2-hexyl-N-(6-((1-hydroxy-2-(hydroxymethyl)-4-(4-octylphenyl) butan-2-yl) amino) hexyl) decanamide (YK-908)

Using YK-908-PM3 (60 mg, 0.14 mmol) and 2-amino-2-[2-(4-octylphenyl)ethyl]-1,3-propanediol (53 mg, 0.17 mmol) as starting materials, YK-908 (20 mg, 0.03 mmol, 22.1%) was obtained following the synthesis method of YK-901. $C_{41}H_{76}N_2O_3$, MS(ES): m/z $(M+H^+)$ 645.6. $^1H$ NMR (400 MHZ, $CDCl_3$) δ 7.14 (s, 4H), 4.04 (dd, J=43.2, 12.5 Hz, 4H), 3.31 (d, J=6.4 Hz, 2H), 3.13 (s, 2H), 2.82-2.65 (m, 2H), 2.63-2.50 (m, 2H), 2.04 (dt, J=36.5, 25.2 Hz, 5H), 1.69-1.18 (m, 44H), 0.90 (dd, J=6.3, 4.0 Hz, 9H).

9. Synthesis of YK-909

The synthesis route is as follows:

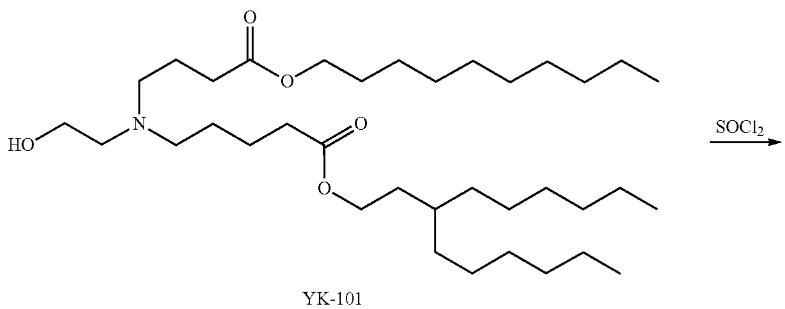

YK-101

-continued

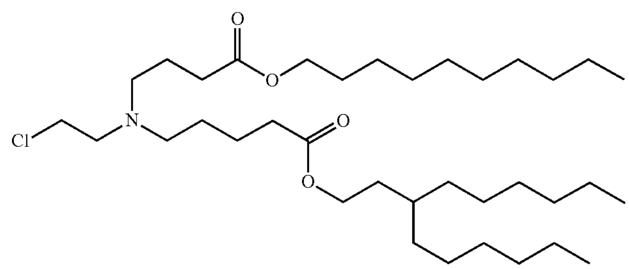

YK-909-PM1

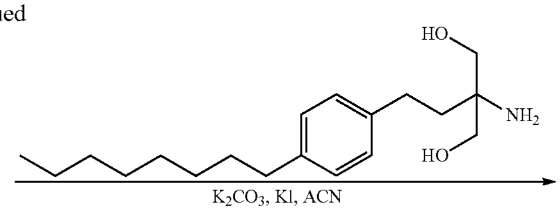

$K_2CO_3$, KI, ACN

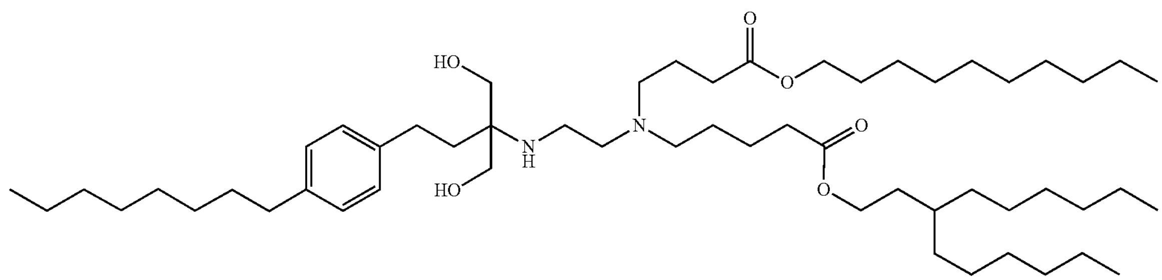

YK-909

Step 1: Synthesis of 3-hexylnonyl 6-((2-chloroethyl) (4-(decyloxy)-4-oxobutyl)amino) hexanoate (YK-909-PM1)

Using 3-hexylnonyl 6-((4-(decyloxy)-4-oxobutyl) (2-hydroxyethyl)amino) hexanoate (YK-101, synthesis method detailed in CN116178193B) (200 mg, 0.33 mmol) as the starting material, YK-909-PM1 (200 mg, 0.32 mmol, 96.1%) was obtained following the synthesis method of YK-906-PM1.

Step 2: Synthesis of 3-hexylnonyl 6-((4-(decyloxy)-4-oxobutyl) (2-((1-hydroxy-2-(hydroxymethyl)-4-(4-octylphenyl) butan-2-yl)amino)ethyl)amino) hexanoate (YK-909)

Using YK-909-PM1 (200 mg, 0.32 mmol) and 2-amino-2-(4-octylphenethyl)-1,3-propanediol (100 mg, 0.33 mmol) as starting materials, YK-909 (130 mg, 0.14 mmol, 45.1%) was obtained following the synthesis method of YK-906. $C_{56}H_{104}N_2O_6$, MS(ES): 901.8m/z ($M+H^+$). $^1H$ NMR (400 MHz, $CDCl_3$) δ 7.09 (s, 4H), 4.47 (s, 4H), 4.02-4.14 (m, 7H), 3.82-3.93 (m, 4H), 3.05 (d, J=28.0 Hz, 4H), 2.62-2.71 (m, 5H), 2.53-2.57 (m, 2H), 2.27-2.38 (m, 4H), 2.04 (s, 3H), 1.83-1.92 (m, 4H), 1.54-1.67 (m, 11H), 1.25-1.30 (m, 38H), 0.86-0.89 (m, 14H).

10. Synthesis of YK-910

The synthesis route is as follows:

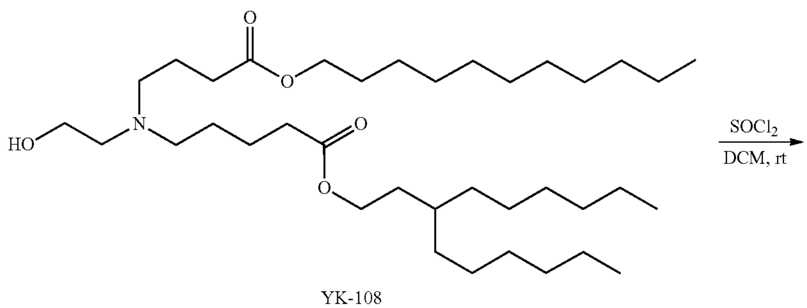

YK-108

-continued

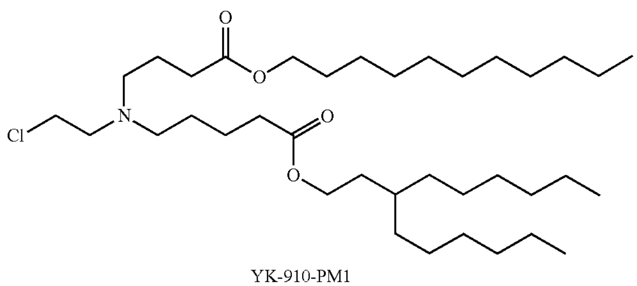

YK-910-PM1

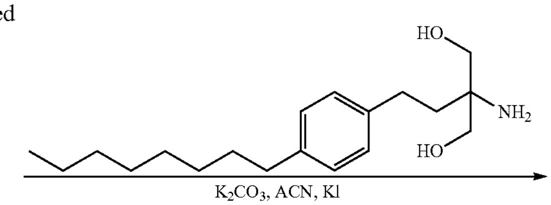

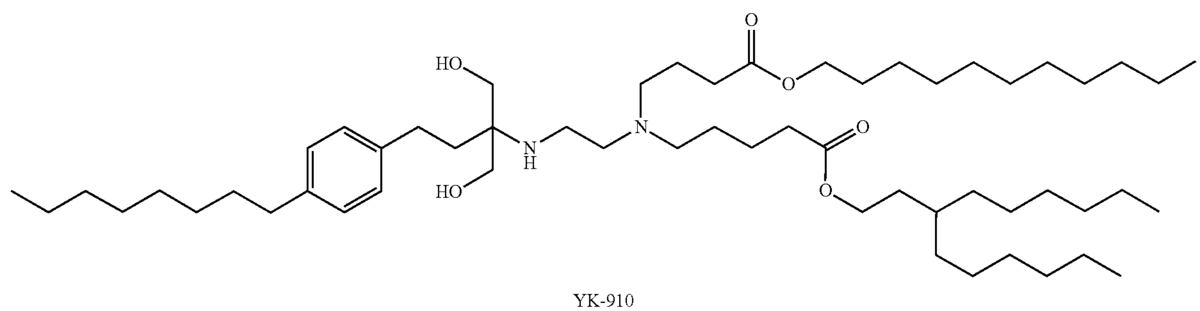

YK-910

Step 1: Synthesis of 3-hexylnonyl 7-((2-chloroethyl) (4-oxo-4-(undecyloxy)butyl)amino) heptanoate (YK-910-PM1)

Using 3-hexylnonyl 7-((2-hydroxyethyl) (4-oxo-4-(undecyloxy)butyl)amino) heptanoate (YK-108, synthesis method detailed in CN116178193B) (300 mg, 0.47 mmol) as the starting material, YK-910-PM1 (300 mg, 0.46 mmol, 96.9%) was obtained following the synthesis method of YK-906-PM1.

Step 2: Synthesis of 3-hexylnonyl 7-((2-((1-hydroxy-2-(hydroxymethyl)-4-(4-octylphenyl) butan-2-yl)amino)ethyl) (4-oxo-4-(undecyloxy)butyl) amino) heptanoate (YK-910)

Using YK-910-PM1 (300 mg, 0.46 mmol) and 2-amino-2-[2-(4-octylphenyl)ethyl]-1,3-propanediol (106 mg, 0.34 mmol) as starting materials, YK-910 (160 mg, 0.17 mmol, 50.6%) was obtained following the synthesis method of YK-901. $C_{58}H_{108}N_2O_6$, MS(ES): m/z ($M+H^+$) 929.8. YK-910: $^1H$ NMR (400 MHZ, $CDCl_3$) δ 7.08 (s, 4H), 4.09-4.03 (m, 4H), δ 3.83-3.71 (m, 4H), 2.95-2.87 (m, 4H), 2.64-2.53 (m, 7H), 2.35-2.27 (m, 4H), 1.84-1.80 (m, 4H), 1.59-1.54 (m, 9H), 1.28-1.25 (m, 54H), 0.89-0.86 (m, 12H).

11. Synthesis of YK-911

The synthesis route is as follows:

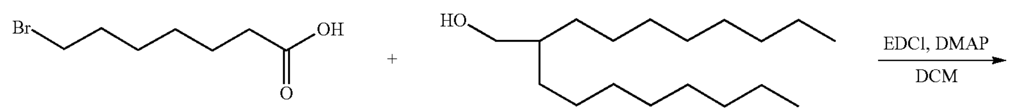

-continued

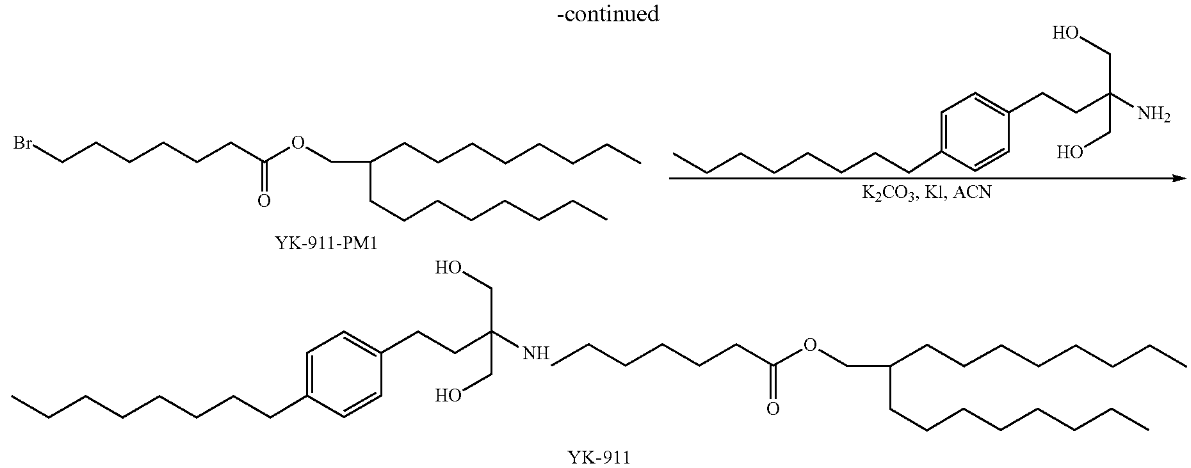

YK-911-PM1

YK-911

Step 1: Synthesis of 2-octyldecyl 7-bromoheptanoate (YK-911-PM1)

Using 7-bromoheptanoic acid (255 mg, 1.22 mmol) and 2-octyldecanol (300 mg, 1.11 mmol) as starting materials, YK-911-PM1 (450 mg, 0.97 mmol, 87.8%) was obtained following the synthesis method of YK-901-PM1.

Step 2: Synthesis of 2-octyldecyl 7-((1-hydroxy-2-(hydroxymethyl)-4-(4-octylphenyl) butan-2-yl) amino) heptanoate (YK-911)

Using YK-911-PM1 (260 mg, 0.56 mmol) and 2-amino-2-(4-octylphenethyl)-1,3-propanediol (174 mg, 0.57 mmol) as starting materials, YK-911 (100 mg, 0.15 mmol, 25.9%) was obtained following the synthesis method of YK-901. $C_{44}H_{81}NO_4$, MS(ES): 688.6 m/z (M+H$^+$). $^1$H NMR (400 MHz, $CDCl_3$) 1H NMR (400 MHZ, CDCl3) δ 7.08 (s, 4H), 4.09-4.14 (m, 3H), 3.95 (d, J=8.0 Hz, 2H), 3.71-3.79 (m, 5H), 2.75 (t, J=8.0 Hz, 2H), 2.53-2.63 (m, 4H), 2.29 (t, J=8.0 Hz, 2H), 2.04 (s, 5H), 1.76-1.80 (m, 2H), 1.65-1.71 (m, 2H), 1.53-1.64 (m, 4H), 1.37 (s, 3H), 1.24-1.29 (m, 34H), 0.87 (t, J=8.0 Hz, 9H).

12. Synthesis of YK-912

The synthesis route is as follows:

Step 1: Synthesis of 2-octyldodecyl 6-bromohexanoate (YK-912-PM1)

Using 2-octyldodecanol (1.00 g, 3.35 mmol) and 6-bromohexanoic acid (0.78 g, 4.00 mmol) as starting materials, YK-912-PM1 (1.15 g, 2.42 mmol, 72.2%) was obtained following the synthesis method of YK-901-PM1.

Step 2: Synthesis of 2-octyldodecyl 6-((1-hydroxy-2-(hydroxymethyl)-4-(4-octylphenyl) butan-2-yl) amino) hexanoate (YK-912)

Using YK-912-PM1 (302 mg, 0.63 mmol) and 2-amino-2-[2-(4-octylphenyl)ethyl]-1,3-propanediol (130 mg, 0.42 mmol) as starting materials, YK-912 (85 mg, 0.12 mmol, 28.8%) was obtained following the synthesis method of YK-901. $C_{45}H_{83}NO_4$, MS(ES): m/z (M+H$^+$) 702.6. $^1$H NMR (400 MHZ, $CDCl_3$) δ 7.09 (s, 4H), 3.96 (d, J=5.8 Hz, 2H), 3.66-3.60 (m, 4H), 2.65-2.53 (m, 6H), 2.32 (t, J=7.4 Hz, 2H), 1.72-1.56 (m, 9H), 1.44-1.25 (m, 44H), 0.88 (t, J=6.4 Hz, 9H).

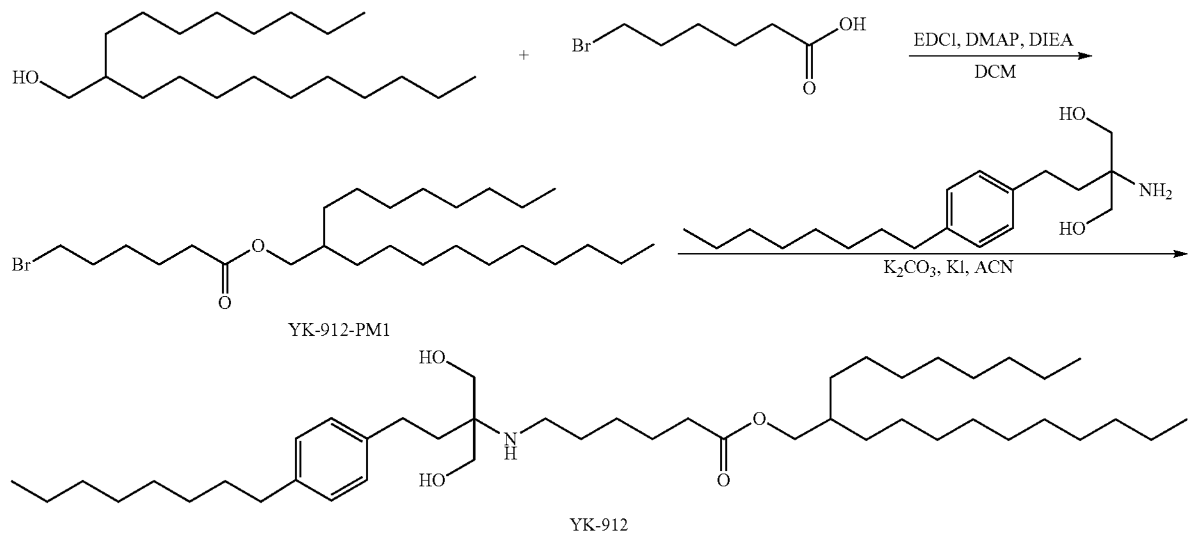

YK-912-PM1

YK-912

13. Synthesis of compound 7

The synthesis route is as follows:

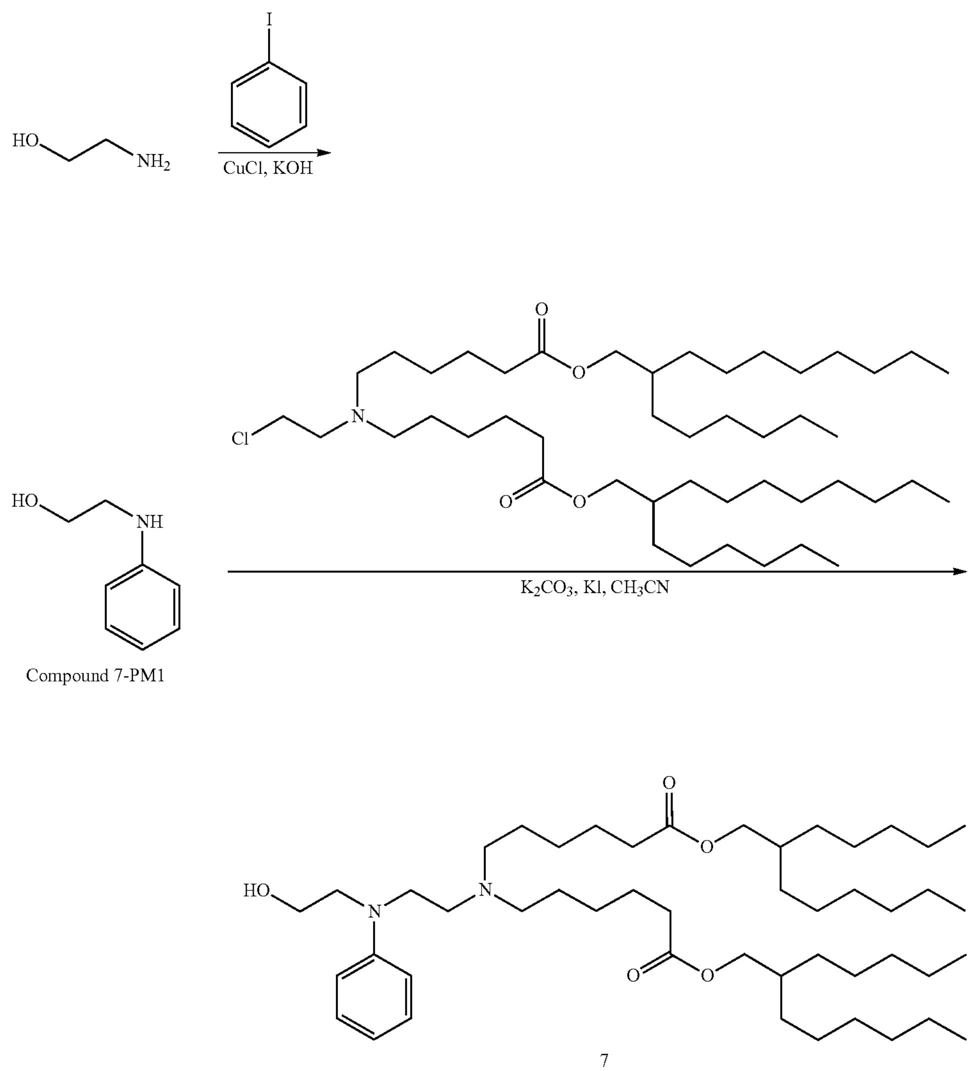

Compound 7-PM1

7

Step 1: Synthesis of 2-(phenylamino) ethan-1-ol (compound 7-PM1)

Iodobenzene (810 mg, 3.97 mmol), ethanolamine (730 mg, 11.95 mmol), copper (I) chloride (39.6 mg, 0.40 mmol), and potassium hydroxide (730 mg, 13.01 mmol) were dissolved in a single-necked flask (10 mL). Under nitrogen atmosphere, the mixture was stirred and reacted at room temperature overnight. After the reaction was completed, 10 mL of purified water was added to quench the reaction. The mixture was extracted with ethyl acetate, dried over anhydrous sodium sulfate, and the solvent was removed under reduced pressure. The residue was purified by silica gel flash chromatography (ethyl acetate/n-hexane) to obtain compound 7-PM1 (430 mg, 3.13 mmol, 79.0%).

Step 2: Synthesis of bis(2-hexyldecyl) 6,6'-((2-((2-hydroxyethyl) (phenyl)amino)ethyl) azanediyl)dihexanoate (compound 7)

Using compound 7-PM1 (100 mg, 0.73 mmol) and bis (2-hexyldecyl) 6,6'-((2-chloroethyl) azetidinyl)dihexanoate (184 mg, 0.24 mmol) as starting materials, compound 7 (92 mg, 0.11 mmol, 44.7%) was obtained following the synthesis method of YK-906. $C_{54}H_{100}N_2O_5$, MS(ES): m/z $(M+H^+)$ 857.8. $^1$HNMR (400 MHZ, $CDCl_3$) δ 7.27-7.13 (m, 2H), 6.73-6.43 (m, 3H), 3.93-3.80 (m, 4H), 3.70-3.58 (m, 5H), 2.68 (s, 1H), 2.42 (t, J=7.4 Hz, 2H), 2.34 (s, 2H), 1.62-1.56 (m, 12H), 1.41-1.28 (m, 56H), 0.88 (t, J=6.3 Hz, 12H).

14. Synthesis of I-1

The synthesis route is as follows:

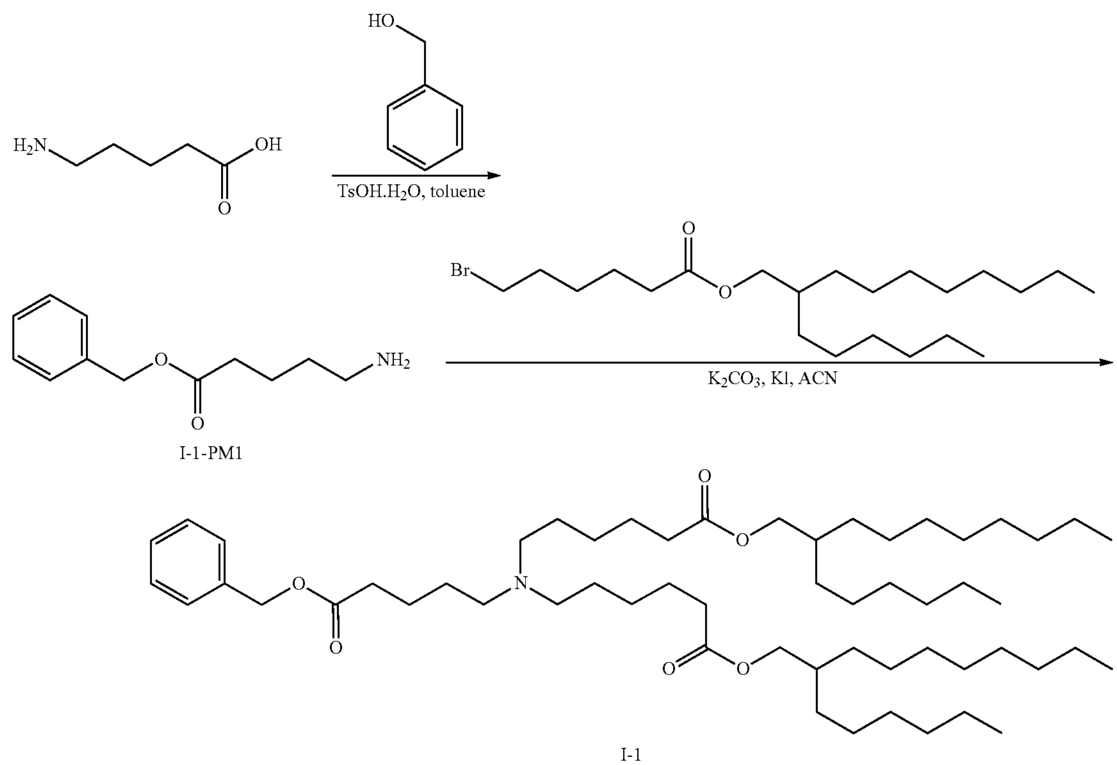

I-1-PM1

I-1

Step 1: Synthesis of 2-(phenylamino) ethan-1-ol (I-1-PM1)

5-Aminopentanoic acid (2.50 g, 21.3 mmol), benzyl alcohol (6.92 g, 64.0 mmol), and p-toluenesulfonic acid monohydrate (4.45 g, 23.4 mmol) were dissolved in toluene (90 mL). A Dean-Stark apparatus and a condenser tube were installed, and the mixture was heated under reflux, stirred and reacted overnight. After the reaction was completed, the mixture was cooled to room temperature and filtered to obtain the p-toluenesulfonate salt of compound I-1-PM1 (5.95 g, 15.7 mmol, 73.6%).

Step 2: Synthesis of bis(2-hexyldecyl) 6,6'-((5-(benzyloxy)-5-oxopentyl) azanediyl)dihexanoate (I-1)

Using the p-toluenesulfonate salt of I-1-PM1 (1.50 g, 3.95 mmol) and 2-hexyldecyl 6-bromohexanoate (2.65 g, 6.32 mmol) as starting materials, I-1 (797 mg, 0.90 mmol, 22.8%) was obtained following the synthesis method of YK-906. $C_{56}H_{101}NO_6$, MS(ES): m/z ($M+H^+$) 884.8. $^1H$ NMR (400 MHZ, $CDCl_3$) δ 7.40-7.33 (m, 5H), 5.11 (s, 2H), 3.94-3.83 (m, 4H), 2.42-2.33 (m, 8H), 2.33 (m, 4H), 1.66-1.59 (m, 8H), 1.51-1.40 (m, 6H), 1.41-1.18 (m, 52H), 0.88 (t, J=6.5 Hz, 12H).

15. Synthesis of YK-501

The synthesis was carried out following the synthesis method described in Example 1 of CN116082275B.

16. Synthesis of YK-506

The synthesis was carried out following the synthesis method described in Example 1 of CN116082275B.

Example 2: Optimization of Lipid Nanoparticles (LNP Preparations) Preparation Conditions 1. Optimization of the Ratio of Vector (liposome) to mRNA The cationic lipid compounds YK-908, YK-909, YK-910, and YK-912, synthesized in Example 1, were each mixed with DSPC (AVT (Shanghai) Pharmaceutical Technology Co., Ltd.), cholesterol (AVT (Shanghai) Pharmaceutical Technology Co., Ltd.), and DMG-PEG2000 in a molar ratio of 49:10:39.5:1.5 and dissolved in ethanol to prepare ethanol lipid solutions. Using the ethanol injection method, the ethanol lipid solutions were quickly added to a citrate buffer (pH between 4 and 5), and vortexed for 30 seconds for later use. eGFP-mRNA (purchased from Shanghai BioHub Biotechnology Co., Ltd.) was diluted in citrate buffer (pH between 4 and 5) to obtain an mRNA aqueous solution. A certain volume of the lipid solution was mixed with the mRNA aqueous solution to prepare liposomes at total lipid-to-mRNA weight ratios of 5:1, 10:1, 15:1, 20:1, 30:1, and 35:1, respectively. The mixtures were sonicated at 25° C. for 15 minutes (ultrasonic frequency: 40 kHz, ultrasonic power: 800 W). The resulting liposomes were diluted 10-fold with PBS, followed by ultrafiltration using a 300 kDa ultrafiltration tube to remove ethanol. After adjusting the volume with PBS, LNP preparations encapsulating eGFP-mRNA were obtained using the cationic lipid YK-908 (or YK-909, YK-910, YK-912), DSPC, cholesterol, and DMG-PEG2000 at a molar ratio of 49:10:39.5:1.5.

Results from the cell transfection experiments showed that the vector-to-mRNA weight ratio in the range of 10:1 to 30:1 resulted in good transfection effects, with the best transfection effects observed at a ratio of 15:1. Transfection effects were poor at the ratios of 5:1 and 35:1, indicating that these ratios cannot be used for mRNA delivery.

2. Optimization of the Ratio of Cationic Lipid to Neutral Lipid

LNP preparations encapsulating eGFP-mRNA were prepared following the method described in section 1, with molar ratios of cationic lipid YK-908 (or YK-909, YK-910, YK-912) to neutral lipid DSPC at 1:1, 3:1, 3.5:1, 4:1, 4.9:1, 10:1, 15:1, and 20:1, respectively.

It can be observed from the cell transfection experiments that the molar ratios of cationic lipids to neutral lipids from 1:1 to 15:1 exhibited transfection effects, with the highest transfection efficiency observed at a molar ratio of 4.9:1.

3. Optimization of the Proportion of Polymer-Conjugated Lipid in Vector (Liposome)

LNP preparations encapsulating eGFP-mRNA were prepared following the method in section 1, with cationic lipid YK-908 (or YK-909, YK-910, YK-912) in the vector. The molar ratios of the polymer-conjugated lipid DMG-PEG2000 in the vector were 0.5%, 1.5%, 2.5%, 3.5%, 5%, 10%, and 15%, respectively.

Cell transfection experiments showed that the molar ratios of the polymer-conjugated lipid in the vector ranging from 0.5% to 10% exhibited transfection effects, with the highest transfection efficiency observed at 1.5% and the lowest observed at 10%.

4. Optimization of the Proportion of Each Component in Vector (Liposome)

LNP preparations encapsulating eGFP-mRNA were prepared following the method described in section 1, with molar ratios of cationic lipid YK-908 (or YK-909, YK-910, YK-912), neutral lipid DSPC, structural lipid cholesterol, and polymer-conjugated lipid DMG-PEG2000 as follows: 75:5:15:5, 65:8:25:2, 49:10:39.5:1.5, 45:10:43.5:1.5, 45:25:20:10, 40:10:48.5:1.5, 35:10:53.5:1.5, and 25:5:65:5, respectively.

It can be observed from the cell transfection experiments that transfection could be achieved at molar ratios of cationic lipids, neutral lipids, structural lipids, and polymer-conjugated lipids being 75:5:15:5, 65:8:25:2, 49:10:39.5:1.5, 45:10:43.5:1.5, 45:25:20:10, 40:10:48.5:1.5, 35:10:53.5:1.5, and 25:5:65:5. The molar ratio range of (35-49):(7.5-15):(35-55):(1-5) resulted in good transfection effects, with the best transfection effect observed at a molar ratio of 49:10:39.5:1.5.

Example 3: Cell Transfection Experiment with LNP Preparations of eGFP-mRNA

Cell recovery and passage: 293T cells were recovered and cultured in culture dishes. The cells were passaged until the required number of cells was obtained.

Seeding plates: The cells in culture dishes were digested and counted, then seeded in a 96-well plate at 10,000 cells per well and seeded in a 12-well plate at 150,000 cells per well. The cells were cultured overnight until cell adhesion.

Cell transfection experiment: LNP preparations containing 1.5 μg of eGFP-mRNA, prepared according to Example 2 (cationic lipids in the vector were YK-908, YK-909, YK-910, YK-912), and Lipofectamine 3000 preparations with eGFP-mRNA were added to the culture medium of cells in the 12-well plate. After 24 hours of continued culture, transfection efficiency was evaluated by observing the fluorescence intensity under a fluorescence microscope.

Based on the experimental results, the final preparation conditions for the lipid nanoparticles (LNP preparations) were determined as follows: a mass ratio of 15:1 for vector and mRNA; a molar ratio of 4.9:1 for cationic lipids and neutral lipids; a molar proportion of 1.5% for polymer-conjugated lipids in liposomes; and a molar ratio of 49:10:39.5:1.5 for cationic lipids, neutral lipids, structural lipids, and polymer-conjugated lipids. Subsequent experiments used these conditions to prepare the lipid nanoparticles (LNP preparations).

Example 4: Preparation of Lipid Nanoparticles (LNP preparations) Using the Optimal Ratio

TABLE 2

| Structure of cationic lipids | | |
|---|---|---|
| Name | Structure | Notes |
| YK-901 | 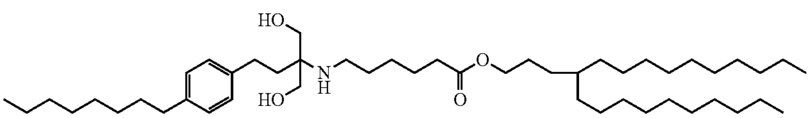 YK-901 | Synthesized in Example 1 |
| YK-902 | 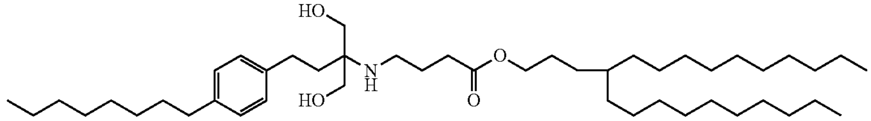 YK-902 | Synthesized in Example 1 |

TABLE 2-continued
| Structure of cationic lipids | | |
|---|---|---|
| Name | Structure | Notes |
| YK-903 | 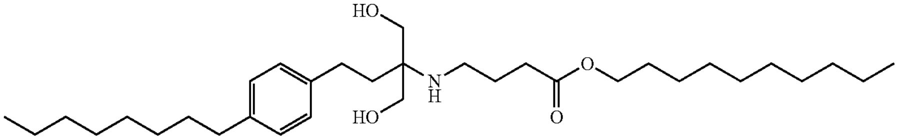 YK-903 | Synthesized in Example 1 |
| YK-904 | 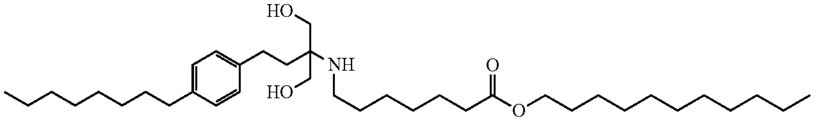 YK-904 | Synthesized in Example 1 |
| YK-905 | 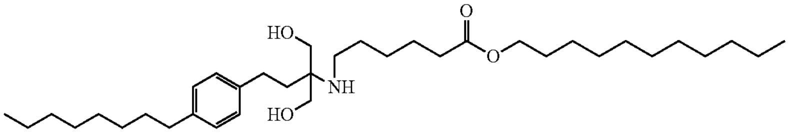 YK-905 | Synthesized in Example 1 |
| YK-906 | 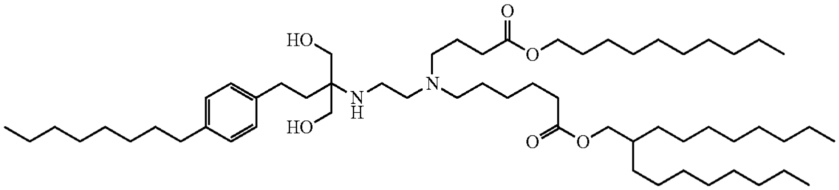 YK-906 | Synthesized in Example 1 |
| YK-907 | 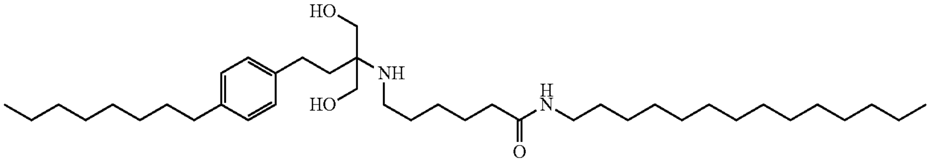 YK-907 | Synthsized in Example 1 |
| YK-908 | 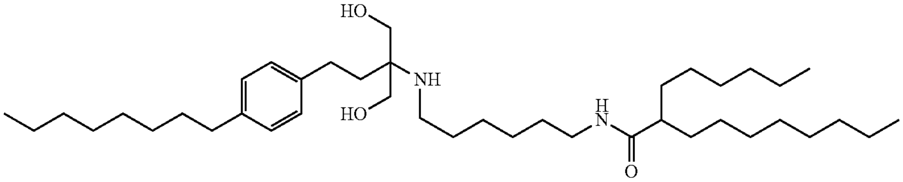 YK-908 | Synthesized in Example 1 |

TABLE 2-continued
| Structure of cationic lipids | | |
|---|---|---|
| Name | Structure | Notes |
| YK-909 | 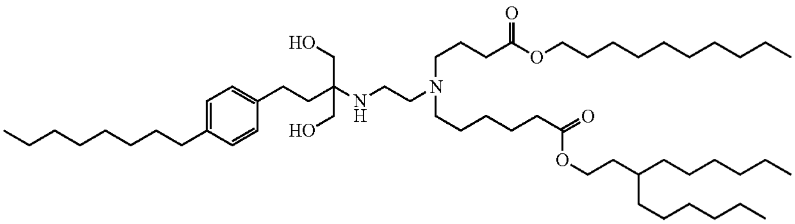 YK-909 | Synthesized in Example 1 |
| YK-910 | 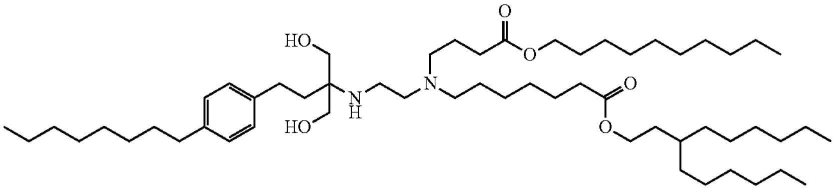 YK-910 | Synthesized in Example 1 |
| YK-911 | 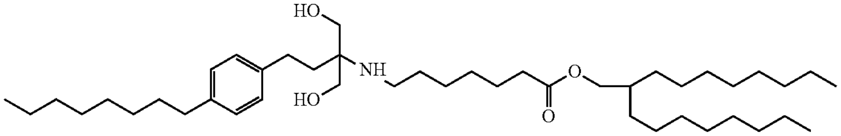 YK-911 | Synthesized in Example 1 |
| YK-912 | 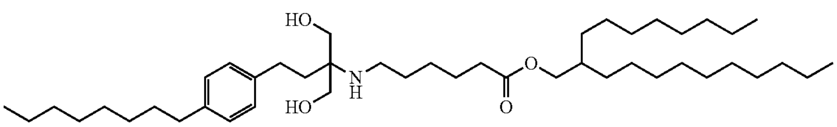 YK-912 | Synthesized in Example 1 |
| SM-102 | 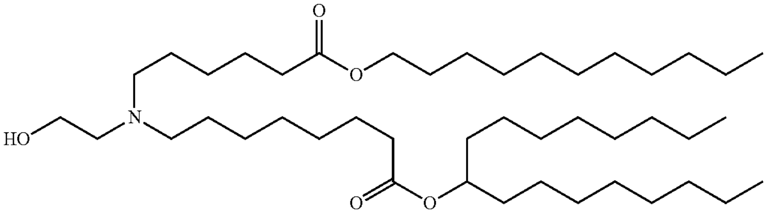 SM-102 | Purchased from Xiamen Sinopeg Biotech Co., Ltd., compound 25 in WO20170409245A2 |
| YK-501 | 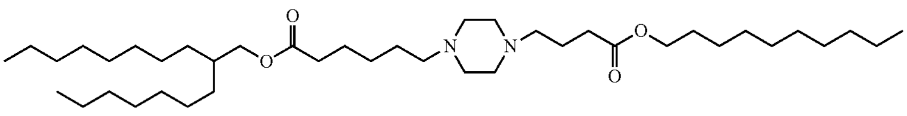 YK-501 | Synthesized in Example 1, YK-501 in CN116082275B |
| YK-506 | 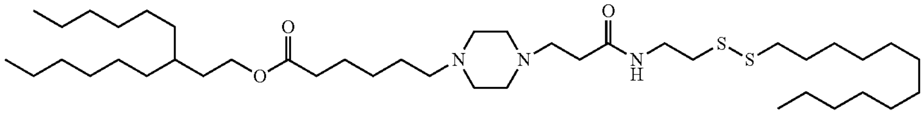 YK-506 | Synthesized in Example 1, YK-506 in CN116082275B |

TABLE 2-continued

| Structure of cationic lipids | | |
|---|---|---|
| Name | Structure | Notes |
| HHMA | 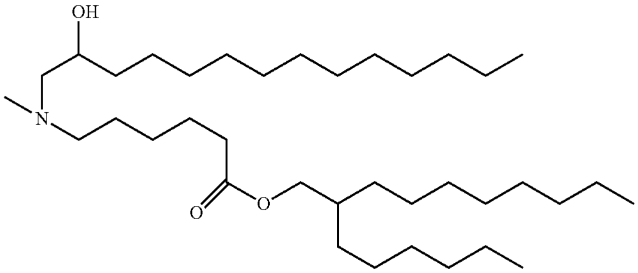 HHMA | Purchased from Xiamen Sinopeg Biotech Co., Ltd., compound 1 in CN108368028B |
| MC3 | 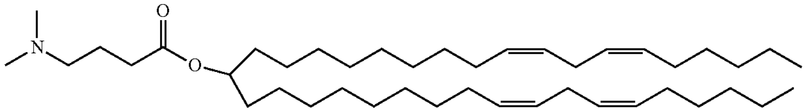 D-Lin-MC3-DMA | Purchased from Xiamen Sinopeg Biotech Co., Ltd., page 6 of the specification in CN102625696B |
| Compound 7 | 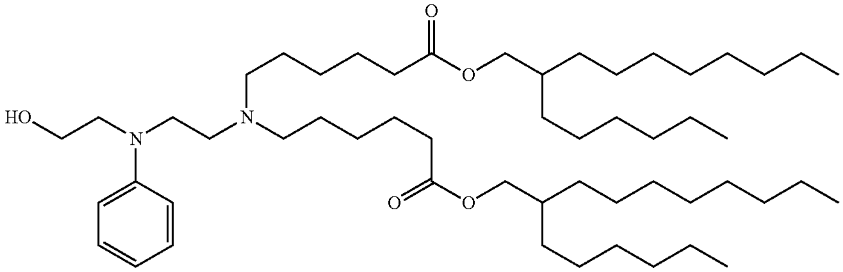 Compound 7 | Synthesized in Example 1, page 45 of the specification in CN114206827A |
| I-1 | 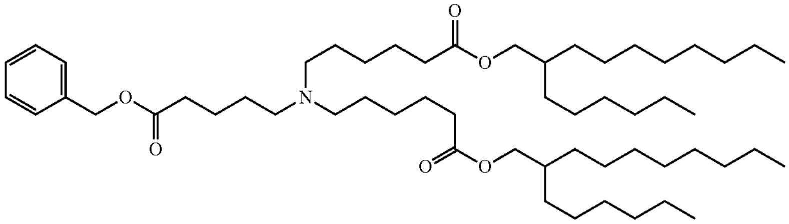 I-1 | Synthesized in Example 1, page 19 of the specification in CN110799492A |

The cationic lipids listed in Table 2 were each mixed with DSPC (AVT (Shanghai) Pharmaceutical Technology Co., Ltd.), cholesterol (AVT (Shanghai) Pharmaceutical Technology Co., Ltd.), and DMG-PEG2000 in a molar ratio of 49:10:39.5:1.5 and dissolved in ethanol to prepare ethanol lipid solutions. Using the ethanol injection method, the ethanol lipid solutions were quickly added to a citrate buffer (pH between 4 and 5), and vortexed for 30 seconds for later use. eGFP-mRNA (purchased from Shanghai BioHub Biotechnology Co., Ltd.), Fluc-mRNA (purchased from Shanghai BioHub Biotechnology Co., Ltd.), or Cy5 fluorescently labeled Leqvio (purchased from Sangon Biotech (Shanghai) Co., Ltd.) was diluted in a citrate buffer (pH between 4 and 5) to obtain an mRNA aqueous solution. A certain volume of the lipid solution and the mRNA aqueous solution were mixed to prepare liposomes at a total lipid-to-mRNA weight ratio of 15:1. The mixtures were sonicated at 25° C. for 15 minutes (ultrasonic frequency: 40 kHz, ultrasonic power: 800 W). The resulting liposomes were diluted 10-fold with PBS, followed by ultrafiltration using a 300 kDa ultrafiltration tube to remove ethanol. After adjusting the volume with PBS, LNP preparations encapsulating eGFP-mRNA or Fluc-mRNA were obtained, using cationic lipids, DSPC, cholesterol, and DMG-PEG2000 at a molar ratio of 49:10:39.5:1.5.

Lipofectamine 3000 transfection reagent is currently widely used for cell transfection, offering excellent transfection performance, high transfection efficiency, and improved cell viability, and is suitable for cell types that are difficult to transfect. Lipofectamine 3000 transfection reagent was used for comparison, and Lipofectamine 3000 preparations of eGFP-mRNA or Fluc-mRNA were prepared according to the manufacturer's instructions for Lipofectamine 3000 (Invitrogen Trading (Shanghai) Co.,Ltd.).

Example 5: Measurement of Particle Size and Polydispersity Index (PDI) of Lipid Nanoparticles The particle size and polydispersity index (PDI) were measured using dynamic light scattering with a Malvern laser diffraction particle size analyzer.

10 μL of liposome solution was diluted to 1 mL with RNase-free deionized water and added to the sample cell. Each sample was measured three times. The measurement conditions were as follows: 90° scattering angle, 25° C. The results are shown in Table 3:

TABLE 3

Particle size and polydispersity index (PDI) of lipid nanoparticles

| Name | Particle size (nm) | PDI (%) |
|---|---|---|
| YK-901 | 162 | 17.4 |
| YK-902 | 142 | 12.4 |
| YK-903 | 152 | 15.1 |
| YK-904 | 112 | 8.2 |
| YK-905 | 135 | 16.9 |
| YK-906 | 124 | 10.2 |
| YK-907 | 159 | 16.2 |
| YK-908 | 121 | 12.2 |
| YK-909 | 132 | 11.9 |
| YK-910 | 126 | 10.3 |
| YK-911 | 136 | 10.4 |
| YK-912 | 123 | 9.5 |
| SM-102 | 145 | 13.5 |
| YK-501 | 144 | 13.3 |
| YK-506 | 141 | 12.2 |
| HHMA | 146 | 16.3 |
| MC3 | 151 | 15.7 |
| Compound 7 | 162 | 14.3 |
| I-1 | 158 | 16.2 |

As shown in Table 3, the particle sizes of the lipid nanoparticles prepared in Example 4 were between 110 to 165 nm, all of which were suitable for mRNA delivery.

Among them, the particles prepared with YK-904 had the smallest size at 112 nm, while those prepared with YK-901 had the largest size at 162 nm.

The polydispersity index (PDI) of all lipid nanoparticles ranged from 8% to 18%, with the lowest being YK-904 at 8.2% and the highest being YK-901 at 17.4%.

The particle morphology of those prepared with YK-908, YK-909, YK-910, and YK-912 also exhibited favorable characteristics, with smaller particle sizes and better uniformity compared with particles prepared with other similar cationic lipids from the prior arts, such as SM-102, HHMA, MC3, compound 7, and I-1.

Example 6: In Vitro Validation of LNP Delivery Vector Performance

Cell recovery and passage: The method was the same as described in Example 3.

Seeding plates: The method was the same as described in Example 3.

1. Fluorescence Detection of Fluc-mRNA (Transfection Efficiency)

LNP preparations containing 0.3 μg of Fluc-mRNA (with the vector components of the LNP preparations of cationic lipids, DSPC, cholesterol, and DMG-PEG2000 in a molar ratio of 49:10:39.5:1.5, where the cationic lipids are those listed in Table 1) were added to the cell culture medium in a 96-well plate. After 24 hours of continued culture, the corresponding reagents were added according to the instructions in the *Gaussia* Luciferase Assay Kit. Fluorescence intensity in each well was detected using the IVIS fluorescence detection system. The chemical structures of the designed compounds and representative cationic lipids from the prior art are listed in Table 2. The transfection efficiency of LNP preparations prepared with a series of cationic lipid compounds designed in the present disclosure, as well as cationic lipids from the prior art, including SM-102, HHMA, MC3, compound 7, and I-1, is shown in Table 4.

Table 4 lists the fluorescence detection results of LNP preparations containing Fluc-mRNA, prepared with different cationic lipids.

TABLE 4

Fluorescence detection results of Fluc-mRNA

| No. | Cationic lipids | Relative light unit (RLU) | Multiple relative to YK-908 | Multiple relative to YK-909 | Multiple relative to YK-910 | Multiple relative to YK-912 |
|---|---|---|---|---|---|---|
| 1 | YK-901 | 43423 | 116.76 | 156.14 | 198.71 | 131.47 |
| 2 | YK-902 | 311132 | 16.30 | 21.79 | 27.73 | 18.35 |
| 3 | YK-903 | 25006 | 202.75 | 271.15 | 345.06 | 228.30 |
| 4 | YK-904 | 125048 | 40.55 | 54.22 | 69.00 | 45.65 |
| 5 | YK-905 | 72425 | 70.00 | 93.62 | 119.14 | 78.83 |
| 6 | YK-906 | 27546 | 184.06 | 246.15 | 313.25 | 207.25 |
| 7 | YK-907 | 37699 | 134.49 | 179.86 | 228.88 | 151.44 |
| 8 | YK-908 | 5070083 | 1.00 | 1.34 | 1.70 | 1.13 |
| 9 | YK-909 | 6780306 | 0.75 | 1.00 | 1.27 | 0.84 |
| 10 | YK-910 | 8628595 | 0.59 | 0.79 | 1.00 | 0.66 |
| 11 | YK-911 | 1299055 | 3.90 | 5.22 | 6.64 | 4.39 |
| 12 | YK-912 | 5708988 | 0.89 | 1.19 | 1.51 | 1.00 |
| 13 | SM-102 | 1428141 | 3.55 | 4.75 | 6.04 | 4.00 |
| 14 | YK-501 | 46243 | 109.64 | 146.62 | 186.59 | 123.45 |
| 15 | YK-506 | 654224 | 7.75 | 10.36 | 13.19 | 8.73 |
| 16 | HHMA | 1011156 | 5.01 | 6.71 | 8.53 | 5.65 |
| 17 | MC3 | 94904 | 53.42 | 71.44 | 90.92 | 60.16 |
| 18 | Compound 7 | 257490 | 19.69 | 26.33 | 33.51 | 22.17 |
| 19 | I-1 | 202730 | 25.01 | 33.44 | 42.56 | 28.16 |
| 20 | Lipofectamine 3000 | 842671 | 6.02 | 8.05 | 10.24 | 6.77 |

Experimental results analysis:

(1) Among the compounds designed in the present disclosure, including YK-908, YK-909, YK-910, and YK-912, compared with representative cationic lipids in the prior art, some show large differences in chemical structure, such as SM-102, MC3, YK-501, YK-506, and HHMA, while some show smaller differences, such as compound 7 and I-1.

Compared with SM-102, MC3, YK-501, YK-506, and HHMA, the compounds designed in the present disclosure exhibit significant differences in chemical structure. From the chemical structural formula, it can be seen that the series of compounds in the present disclosure introduce the structure of 2-amino-2-[2-(4-(alkyl)phenyl)ethyl]-1,3-propanediol, where the amino group is connected to a lipid at the head of ethyl tertiary amine, a linear alkyl group containing ester groups or amide groups, or a branched alkyl group containing ester groups or amide groups. In contrast, SM-102, MC3, YK-501, YK-506, and HHMA do not contain the 2-amino-2-[2-(4-(alkyl)phenyl)ethyl]-1,3-propanediol structure. The amino head structure of SM-102 is a simple ethanolamine structure; the amino head structure of MC3 is a dimethyl tertiary amine structure without a hydroxyl structure; the amino head of YK-501 and YK-506 is a piperazinyl group; the amino head of HHMA is a methyl tertiary amine structure with the hydroxyl group located at the 2-position of the fatty chain, and other groups also show significant differences.

Compound 7, I-1, and the compounds designed in the present disclosure all contain a benzene ring structure, resulting in smaller chemical structure differences.

(2) In the series of compounds designed, LNP preparations prepared with YK-908, YK-909, YK-910, and YK-912 resulted in significantly improved cellular transfection efficiency compared with representative cationic lipids in the prior art. For example, the cellular transfection efficiency of YK-910 ("the cellular transfection efficiency of YK-910" refers to the the cellular transfection efficiency of LNP preparations prepared with YK-910, and other similar expressions also refer to similar meanings) could reach 6.04 times that of SM-102, 186.59 times that of YK-501, 13.19 times that of YK-506, 8.53 times that of HHMA, 90.92 times that of MC3, 33.51 times that of compound 7, 42.56 times that of I-1, and 10.24 times that of Lipofectamine 3000.

SM-102, HHMA, and MC3 are representative cationic lipids from the prior art, with good transfection performance.

Figure 2:
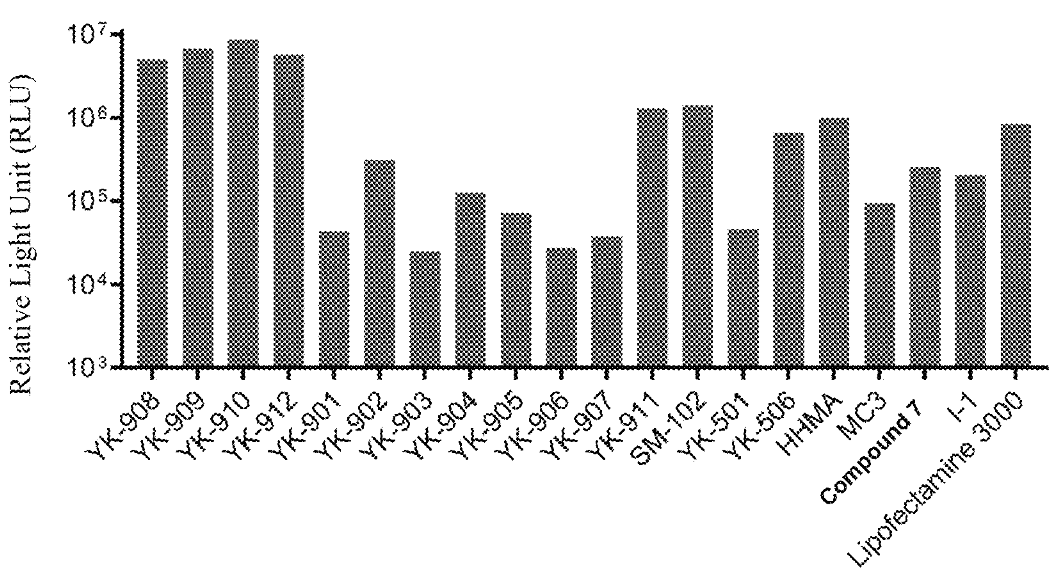
FIG. 2 shows the fluorescence intensity of LNP preparations of Fluc-mRNA prepared with different cationic lipids.

As shown in Table 4, the LNP preparations containing Fluc-mRNA prepared with YK-908, YK-909, YK-910, and YK-912 resulted in the strongest fluorescence absorption, with RLU values of U.S. Pat. Nos. 5,070,083, 6,780,306, 8,628,595, and 5,708,988, respectively (FIG. 1 and FIG. 2).

The cellular transfection efficiency of YK-908 could reach 3.55 times that of SM-102, 109.64 times that of YK-501, 7.75 times that of YK-506, 5.01 times that of HHMA, 53.42 times that of MC3, 19.69 times that of compound 7, 25.01 times that of I-1, and 6.02 times that of Lipofectamine 3000, demonstrating a significant improvement in transfection efficiency.

The cellular transfection efficiency of YK-909 could reach 4.75 times that of SM-102, 146.62 times that of YK-501, 10.36 times that of YK-506, 6.71 times that of HHMA, 71.44 times that of MC3, 26.33 times that of compound 7, 33.44 times that of I-1, and 8.05 times that of Lipofectamine 3000, demonstrating a significant improvement in transfection efficiency.

The cellular transfection efficiency of YK-910 could reach 6.04 times that of SM-102, 186.59 times that of YK-501, 13.19 times that of YK-506, 8.53 times that of HHMA, 90.92 times that of MC3, 33.51 times that of compound 7, 42.56 times that of I-1, and 10.24 times that of Lipofectamine 3000, demonstrating a significant improvement in transfection efficiency.

The cellular transfection efficiency of YK-912 could reach 4.00 times that of SM-102, 123.46 times that of YK-501, 8.73 times that of YK-506, 5.65 times that of HHMA, 60.16 times that of MC3, 22.17 times that of compound 7, 28.16 times that of I-1, and 6.77 times that of Lipofectamine 3000, demonstrating a significant improvement in transfection efficiency.

The cellular transfection efficiency of YK-902 was 0.22 times that of SM-102, 6.73 times that of YK-501, 0.48 times that of YK-506, 0.31 times that of HHMA, 3.28 times that of MC3, 1.21 times that of compound 7, and 1.53 times that of I-1.

It can be seen that it is impossible to predict the transfection efficiency of LNP preparations based on the structure of the cationic lipid compounds. Whether the structural differences are large or small, the cellular transfection efficiency is very likely to vary greatly.

(3) In the series of compounds where $M_1$ is-C(O)O—, the LNP preparations prepared with YK-912 resulted in significantly improved cellular transfection efficiency compared with other compounds. For example, the transfection efficiency of YK-912 could reach 228 times that of YK-903 and 131 times that of YK-901.

A series of structurally similar compounds where $M_1$ is-C(O)O—, including YK-901, YK-902, YK-903, YK-904, YK-905, YK-911, and YK-912, were compared. The differences between these compounds lie only in minor variations in certain groups (Table 2). The cellular transfection results demonstrated a wide range of activities within this series of compounds, with YK-912 achieving the highest cellular transfection efficiency, showing a significant improvement over the other compounds. The transfection efficiency of YK-912 could reach 131.47 times that of YK-901, 18.35 times that of YK-902, 228.30 times that of YK-903, 45.65 times that of YK-904, 78.83 times that of YK-905, and 4.39 times that of YK-911, demonstrating a significant improvement in transfection efficiency.

(4) Among the compounds where $M_1$ is an amide bond (—C(O)NH— or —NHC(O)—), the LNP preparations prepared with YK-908 resulted in significantly improved cellular transfection efficiency compared with YK-907, reaching 134 times that of YK-907.

The structurally similar compounds YK-907 and YK-908, where $M_1$ is —C(O)NH— or —NHC(O)—, were compared. It can be seen that the LNP preparations prepared with YK-908 resulted in significantly improved cellular transfection efficiency compared with YK-907, reaching 134.49 times that of YK-907.

(5) Among the series of compounds where $X_1$ is N, the LNP preparations prepared with YK-909 and YK-910 resulted in significantly improved cellular transfection efficiency compared with YK-906, reaching 246 times and 313 times that of YK-906, respectively.

The structurally similar compounds where $X_1$ is N, including YK-906, YK-909, and YK-910, were compared. The results showed that the LNP preparations prepared with YK-909 and YK-910 resulted in significantly improved cellular transfection efficiency compared with YK-906, reaching 246.15 and 313.25 times that of YK-906, respectively.

It can be seen that it is impossible to predict the cellular transfection activity of LNP preparations based on the structure of the cationic lipid compounds. Even among a series of structurally very similar cationic lipid compounds, the cellular transfection efficiency is very likely to vary greatly.

2. Cell Viability Assay

LNP preparations containing 1.5 μg of Fluc-mRNA (with the vector components of the LNP preparations of cationic lipids, DSPC, cholesterol, and DMG-PEG2000 in a molar ratio of 49:10:39.5:1.5, where the cationic lipids are those listed in Table 1) were added to the cell culture medium in a 96-well plate. After 24 hours of continued culture, 10 μL of CCK-8 solution was added to each well, and the culture plate was incubated in an incubator for 1 hour. The absorbance at 450 nm was measured using a microplate reader, and the cell viability results are shown in Table 5.

TABLE 5

| Cell viability | | |
|---|---|---|
| No. | Cationic lipids | Cell viability (%) |
| 1 | YK-901 | 58 |
| 2 | YK-902 | 36 |
| 3 | YK-903 | 47 |
| 4 | YK-904 | 52 |
| 5 | YK-905 | 51 |
| 6 | YK-906 | 63 |
| 7 | YK-907 | 73 |
| 8 | YK-908 | 89 |
| 9 | YK-909 | 92 |
| 10 | YK-910 | 94 |
| 11 | YK-911 | 62 |
| 12 | YK-912 | 87 |
| 13 | SM-102 | 82 |
| 14 | YK-501 | 63 |
| 15 | YK-506 | 90 |
| 16 | HHMA | 77 |
| 17 | MC3 | 74 |
| 18 | Compound 7 | 73 |
| 19 | I-1 | 68 |
| 20 | Lipofectamine 3000 | 31 |

Experimental Results Analysis:

(1) In the series of compounds designed in the present disclosure, including YK-908, YK-909, YK-910, and YK-912, compared with representative cationic lipids in the prior art, some show large differences in chemical structure, such as SM-102, MC3, YK-501, YK-506, and HHMA, while some show smaller differences, such as compound 7 and I-1.

Figure 3:
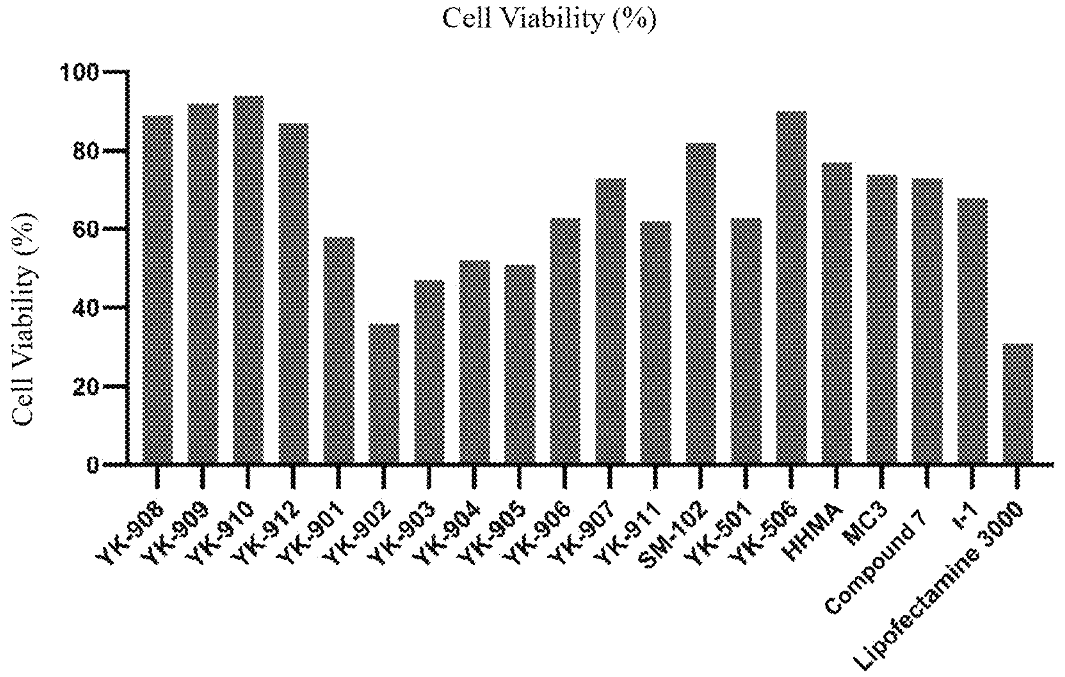
FIG. 3 shows the cell viability after 24 hours of incubation with LNP preparations of Fluc-mRNA prepared with different cationic lipids in the cell culture medium.

The experimental results showed that LNP preparations prepared with YK-909 and YK-910 demonstrated the lowest cytotoxicity, and their cell viability was significantly improved compared with representative cationic lipids in the prior art. For example, the cell viability of YK-910 ("the cell viability of YK-910" refers to the cell viability resulting from LNP preparations prepared with YK-910, and other similar expressions also refer to similar meanings) could be 12% higher than that of SM-102, 31% higher than that of YK-501, 17% higher than that of HHMA, 20% higher than that of MC3, 21% higher than that of compound 7, 26% higher than that of I-1, and 63% higher than that of Lipofectamine 3000 (FIG. 3).

(2) A series of structurally similar compounds where $M_1$ is —C(O)O—, including YK-901, YK-902, YK-903, YK-904, YK-905, YK-911, and YK-912, were compared. The differences between these compounds lie only in minor variations in certain groups.

The experimental results showed that the cytotoxicity of this series of compounds differs greatly. Among them, the cell viability of YK-912 was the highest, which was 29% higher than that of YK-901, 51% higher than that of YK-902, 40% higher than that of YK-903, 35% higher than that of YK-904, 36% higher than that of YK-905, and 25% higher than that of YK-911, indicating that the cell viability was significantly improved.

(3) The structurally similar compounds YK-907 and YK-908, where $M_1$ is an amide bond (—C(O)NH— or —NHC(O)—) were compared. The results showed that the cell viability of YK-908 was significantly improved, which could be 16% higher than that of YK-907.

(4) The structurally similar compounds where $X_1$ is N, including YK-906, YK-909, and YK-910, were compared. The results showed that the cell viability of YK-909 and YK-910 was significantly improved compared with YK-906, being 29% and 31% higher than that of YK-906, respectively.

It can be seen that it is impossible to predict the cytotoxicity of LNP preparations based on the structure of the cationic lipid compounds. Whether they are compounds with huge structural differences or similar structures, the cytotoxicity to transfected cells are very likely to vary greatly.

Example 7: In Vivo Validation of Cationic Lipid (LNP) Delivery Vector Performance This example validates the expression and duration of mRNA delivered by the designed cationic lipid in mice in vivo. The in vivo experiments further demonstrated that the LNP delivery vector of the present disclosure, compared with representative cationic lipids from the prior art, could: (1) efficiently deliver mRNA to the animal and enable efficient and sustained expression; (2) ensure high expression of delivered mRNA in the spleen with lower expression in the liver; (3) ensure high expression of delivered small nucleic acid drugs in the spleen.

1. Expression of Delivered mRNA in Mice In Vivo

LNP preparations containing 10 μg of Fluc-mRNA were injected via the tail vein into female BALB/C mice (4 to 6 weeks old, weighing 17 to 19 g). At specified time points after administration (6 h, 24 h, 48 h, and 7 d), the mice were intraperitoneally injected with fluorescent imaging substrates and allowed to move freely for 5 minutes. The average radiation intensity (corresponding to fluorescence intensity) of proteins expressed by the mRNA delivered by the LNP preparations in the mice in vivo was then detected using the IVIS Spectrum small-animal in vivo imaging system. The in vivo imaging detection results of mice are shown in Table 6.

TABLE 6

| In vivo imaging experimental data of mice | | | | |
|---|---|---|---|---|
| Cationic | Time | | | |
| lipids | 6 h | 24 h | 48 h | 7 d |
| YK-904 | 1116384 | 115355 | 28552 | 3243 |
| YK-908 | 8918424 | 1176543 | 344643 | 64325 |
| YK-909 | 12924543 | 1322432 | 576433 | 87433 |
| YK-910 | 13425454 | 2133322 | 658643 | 85363 |
| YK-912 | 7543664 | 932533 | 354363 | 56756 |
| SM-102 | 2144435 | 314533 | 134554 | 9243 |
| YK-501 | 346241 | 174776 | 55543 | 5634 |
| YK-506 | 1801233 | 257765 | 82221 | 34234 |
| Compound 7 | 1847654 | 185473 | 96543 | 8511 |

Experimental Results Analysis:

(1) mRNA delivered by LNP preparations prepared from YK-908, YK-909, YK-910, and YK-912 showed high and sustained expression in mice in vivo. Compared with representative cationic lipids from the prior art, such as SM-102, YK-501, YK-506, and compound 7, the mRNA expression levels at 6 h, 24 h, 48 h, and 7 d were significantly increased. For example, at 24 h, the expression levels of mRNA delivered by LNP preparations prepared with YK-910 could reach 6.78 times that of SM-102, 12.21 times that of YK-501, 8.28 times that of YK-506, and 11.50 times that of compound 7. At 7 d, the expression levels of mRNA delivered by LNP preparations prepared with YK-910 could reach 9.24 times that of SM-102, 15.15 times that of YK-501, 2.49 times that of YK-506, and 10.03 times that of compound 7.

(2) Compared with compound YK-904, which has a similar structure with slight differences in individual groups, LNP preparations prepared with YK-908, YK-909, YK-910, and YK-912 resulted in significantly improved mRNA expression intensity and duration in mice in vivo. For example, at 6 h, 24 h, 48 h, and 7 d, the expression levels of mRNA delivered by LNP preparations prepared with YK-910 could reach 12.03, 18.49, 23.07, and 26.32 times that of YK-904, respectively.

It can be seen that even small structural differences in cationic lipid compounds can result in large variations in mRNA expression in animals in vivo when formulated as LNP preparations. It is impossible to predict whether an mRNA will exhibit high and sustained expression in animals in vivo based on the chemical structure of the cationic lipids. Identifying cationic lipid compounds that enable extremely high and sustained mRNA expression requires significant inventive labor.

2. Expression of Delivered mRNA in Different Organs of Mice

The liposomes prepared with the cationic lipid compounds of the present disclosure, compared with representative cationic lipids from the prior art, such as SM-102, YK-501, YK-506, and compound 7, resulted in reduced protein expression in the liver or did not remain in the liver to express the target protein. Therefore, compared with the cationic lipids in the prior art, the LNP preparations prepared with the compounds designed in the present disclosure resulted in reduced liver toxicity or were non-toxic.

LNP preparations containing 5 μg of Fluc-mRNA were subcutaneously injected into female BALB/C mice (4 to 6 weeks old, weighing 17 to 19 g). At specified time points after administration (6 h), the mice were intraperitoneally injected with fluorescent imaging substrates and allowed to move freely for 5 minutes. The average radiation intensity (corresponding to fluorescence intensity) of proteins expressed by the mRNA delivered by the LNP preparations in the mice in vivo was then detected using the IVIS Spectrum small-animal in vivo imaging system. After sampling, the mice were killed by cervical dislocation and dissected, and the internal organs: heart, liver, spleen, lung, kidney, and lymph of mice were accurately isolated. The average radiation intensity (corresponding to fluorescence intensity) of proteins expressed by the mRNA delivered by the LNP preparations in various organs of mice was then detected using the IVIS Spectrum small-animal in vivo imaging system. The in vivo imaging detection results of mice are shown in Table 7.

TABLE 7

Organ imaging experimental data of mice 6 hours after Fluc-mRNA administration

| Cationic | Average radiation intensity of mouse organs | | | | | |
|---|---|---|---|---|---|---|
| lipids | Heart | Liver | Spleen | Lung | Kidney | Lymph |
| YK-908 | 0 | 1423 | 168302 | 0 | 0 | 0 |
| YK-909 | 0 | 9131 | 204435 | 0 | 0 | 0 |
| YK-910 | 0 | 11424 | 242444 | 0 | 0 | 0 |
| YK-912 | 0 | 0 | 175366 | 0 | 0 | 0 |
| SM-102 | 0 | 24365 | 25547 | 0 | 0 | 0 |
| YK-501 | 0 | 3334 | 14224 | 0 | 0 | 0 |
| YK-506 | 0 | 18913 | 71213 | 0 | 0 | 0 |

Experimental Results Analysis:

LNP preparations prepared with YK-908, YK-909, YK-910, and YK-912 resulted in significantly increased expression levels of mRNA in the spleen of mice compared with representative cationic lipids in the prior art. For example, the expression levels of YK-908, YK-909, YK-910, and YK-912 ("the expression levels of YK-908" refer to the expression levels of mRNA delivered by LNP preparations prepared with YK-908, and other similar expressions also refer to similar meanings) in the spleen were large, which were 6.59 times, 8.00 times, 9.49 times, and 6.86 times that of SM-102, respectively; 11.83 times, 14.37 times, 17.04 times, and 12.33 times that of YK-501, respectively; and 2.36 times, 2.87 times, 3.40 times, and 2.46 times that of YK-506, respectively.

In the liver, the expression levels of YK-908, YK-909, YK-910, and YK-912 were significantly lower than SM-102. The expression level of SM-102 in the liver was 17.12 times, 2.67 times, and 2.13 times that of YK-908, YK-909, and YK-910, respectively, while YK-912 resulted in no expression in the liver. Therefore, compared with the cationic lipids in the prior art, the LNP preparations prepared from the compounds designed in the present disclosure exhibited reduced liver toxicity or were non-toxic.

Figure 4:
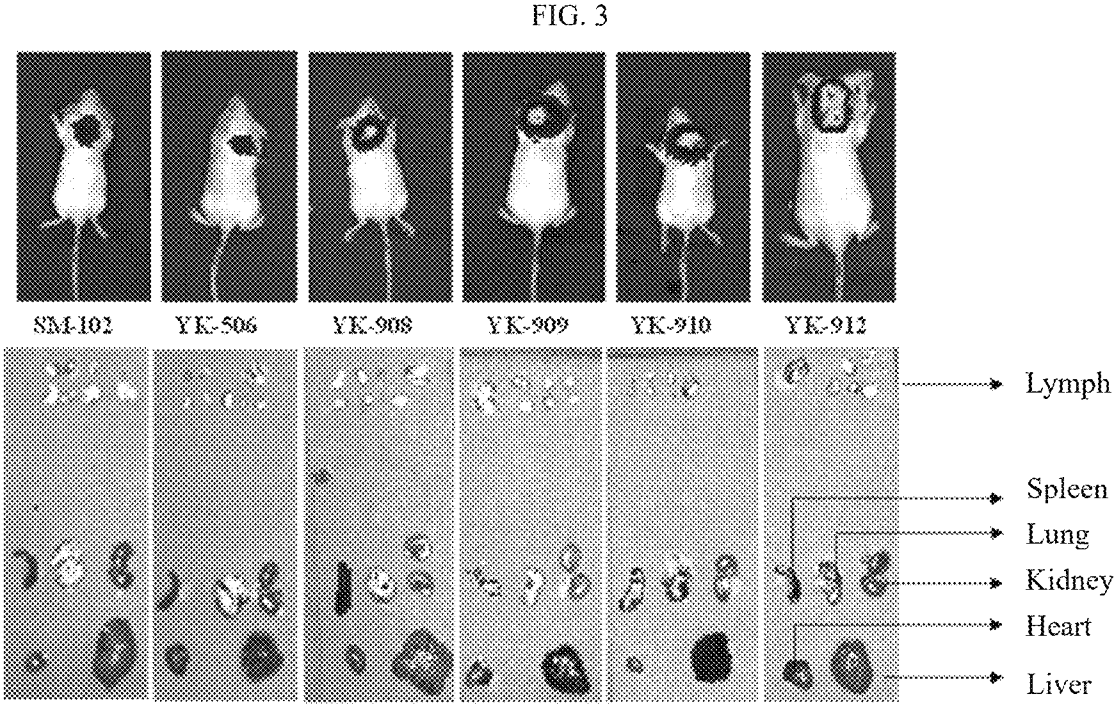
FIG. 4 shows fluorescence images of mouse organs (heart, liver, spleen, lung, kidney, and lymph) for LNP preparations of Fluc-mRNA prepared with SM-102, YK-506, YK-908, YK-909, YK-910, and YK-912.

In addition, LNP preparations containing Fluc-mRNA prepared with all compounds resulted in very different expression levels in various organs of mice. YK-908, YK-909, YK-910, and YK-912 resulted in almost exclusive expression in the spleen, with no expression in other organs such as the heart, lung, and kidney, and little or no expression in the liver. SM-102 resulted in expression in both the liver and spleen, with no expression in the heart, lung, or kidney (FIG. 4).

3. Expression of Delivered Small Nucleic Acid Drugs in Different Organs of Mice

Small nucleic acid drugs delivered by the delivery vectors prepared with the cationic lipids YK-908, YK-909, YK-910, and YK-912 designed in the present disclosure significantly enriched in the spleen of mice, while renal excretion was significantly reduced. Compared with cationic lipids from the prior art, the delivery of Cy5-conjugated small nucleic acid drugs (Cy5 fluorescently labeled Leqvio) resulted in significantly increased fluorescence in the liver and spleen of mice, while fluorescence in the kidney was significantly reduced. The in vivo experiments further confirmed that our LNP delivery vector was also effective in delivering small nucleic acid drugs to animals in vivo, producing efficient and sustained therapeutic effects in the spleen.

LNP preparations containing 5 μg of Cy5 fluorescently labeled Leqvio were injected via the tail vein into female BALB/C mice (4 to 6 weeks old, weighing 17 to 19 g). At a specific time point after administration (4 h), the average radiation intensity (corresponding to fluorescence intensity) resulting from the Cy5 fluorescently labeled Leqvio delivered by the LNP preparations in the mice in vivo was detected using the IVIS Spectrum small-animal in vivo imaging system. After sampling, the mice were killed by cervical dislocation and dissected, and the internal organs: heart, liver, spleen, lung, kidney, and lymph of mice were accurately isolated. The average radiation intensity (corresponding to fluorescence intensity) resulting from Cy5 fluorescently labeled Leqvio delivered by the LNP preparations in various organs of mice was then detected using the IVIS Spectrum small-animal in vivo imaging system. The organ imaging detection results of mice are shown in Table 8.

TABLE 8

Organ imaging experimental data of mice 4 hours after administration of Cy5 fluorescently labeled Leqvio

| Cationic | Average radiation intensity of mouse organs | | | | | |
|---|---|---|---|---|---|---|
| lipids | Heart | Liver | Spleen | Lung | Kidney | Lymph |
| YK-908 | 0 | 14232 | 42432 | 0 | 35322 | 0 |
| YK-909 | 0 | 22334 | 53532 | 0 | 42432 | 0 |
| YK-910 | 0 | 33583 | 63583 | 0 | 53243 | 0 |
| YK-912 | 0 | 54254 | 13443 | 0 | 3433 | 0 |
| SM-102 | 0 | 43324 | 1242 | 0 | 24223 | 0 |
| YK-501 | 0 | 3133 | 5340 | 0 | 12334 | 0 |
| YK-506 | 0 | 8344 | 22321 | 0 | 22743 | 0 |
| Direct administration | 0 | 14434 | 422 | 0 | 37354 | 0 |

Figure 5:
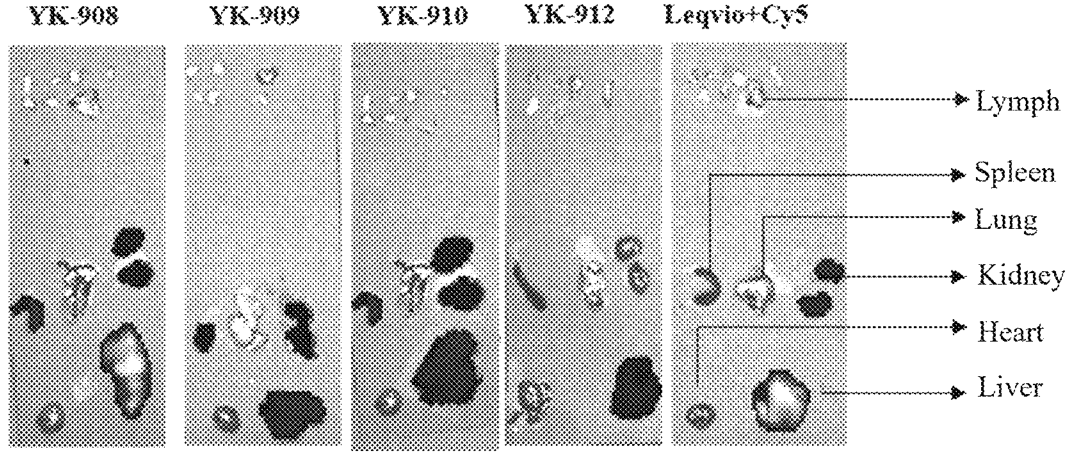
FIG. 5 shows fluorescence images of mouse organs (heart, liver, spleen, lung, kidney, and lymph) for LNP preparations of Cy5 fluorescently labeled Leqvio prepared with YK-908, YK-909, YK-910, and YK-912, as well as direct injection of Cy5 fluorescently labeled Leqvio.

Experimental Results Analysis:

(1) LNP preparations prepared with YK-908, YK-909, YK-910, and YK-912 resulted in significantly increased distribution of small nucleic acid drugs in the spleen of mice compared with representative cationic lipids in the prior art. For example, the fluorescence intensity of YK-908, YK-909, and YK-910 ("the fluorescence intensity of YK-908" refers to the fluorescence intensity resulting from the Cy5 fluorescently labeled Leqvio delivered by the LNP preparations with YK-908, and other similar expressions also refer to similar meanings) in the spleen was 34.16 times, 43.10 times, and 51.19 times that of SM-102, and 7.95 times, 10.02 times, and 11.91 times that of YK-501, respectively (FIG. 5).

Surprisingly, the distribution of small nucleic acid drugs resulting from YK-912 in the kidney was significantly reduced, being only 0.14 times that of SM-102, indicating its potential for long-lasting small nucleic acid drug delivery.

(2) Compared with direct administration, the LNP preparations prepared with YK-908, YK-909, YK-910, and YK-912 resulted in significantly increased distribution of small nucleic acid drugs in the spleen of the mice. The fluorescence intensity in the spleen was 100.55 times, 126.85 times, 150.67 times, and 31.86 times that of direct administration, respectively.

Moreover, the distribution of small nucleic acid drugs resulting from YK-912 in the kidney was significantly reduced compared with direct administration, being only 0.09 times that of direct administration, indicating its potential for long-lasting small nucleic acid drug delivery.

In conclusion, the present disclosure has designed a series of cationic lipid compounds, such as YK-908, YK-909, YK-910, and YK-912, which significantly improve cellular transfection efficiency, reduce cytotoxicity, and enhance the expression levels of mRNA and small nucleic acids in the spleen of mice. Additionally, YK-912 results in significantly reduced renal excretion when delivering small nucleic acid drugs.

1. In the series of designed compounds, including YK-908, YK-909, YK-910, and YK-912, compared with representative cationic lipids from the prior art, some show large structural differences, such as SM-102, MC3, YK-501, YK-506, and HHMA, while some have smaller differences, such as compound 7 and I-1.
2. In this series of designed compounds, the LNP preparations prepared with YK-908, YK-909, YK-910, and YK-912 resulted in significantly improved cellular transfection efficiency, significantly reduced cytotoxicity, and significantly enhanced expression levels of mRNA and small nucleic acids in the spleen of mice compared with representative and structurally similar cationic lipids from the prior art. Additionally, YK-912 resulted in significantly reduced renal excretion when delivering small nucleic acids.

For example, the cellular transfection efficiency of YK-910 could reach 6.04 times that of SM-102, 186.59 times that of YK-501, 13.19 times that of YK-506, 8.53 times that of HHMA, 90.92 times that of MC3, 33.51 times that of compound 7, 42.56 times that of I-1, and 10.24 times that of Lipofectamine 3000. The cell viability of YK-910 could reach 12% higher than that of SM-102, 31% higher than that of YK-501, 17% higher than that of HHMA, 20% higher than that of MC3, 21% higher than compound 7, 26% higher than that of I-1, and 63% higher than that of Lipofectamine 3000. The expression levels of mRNA in animals in vivo 24 hours after administration resulting from YK-910 could reach 6.78 times that of SM-102, 12.21 times that of YK-501, 8.28 times that of YK-506, and 11.50 times that of compound 7. The mRNA expression levels in the spleen resulting from YK-910 could reach 9.49 times that of SM-102, 17.04 times that of YK-501, and 3.40 times that of YK-506. The distribution of small nucleic acids in the spleen resulting from YK-910 could reach 51.19 times that of SM-102, 11.91 times that of YK-501, and 2.85 times that of YK-506. The fluorescence intensity of YK-912 in the spleen and liver was 1.25 times and 10.82 times that of SM-102, respectively, its distribution in the kidney was significantly reduced, being 0.14 times that of SM-102.

3. In the series of compounds designed in the present disclosure with minimal differences in chemical structure, LNP preparations prepared with YK-908, YK-909, YK-910, and YK-912, compared with other compounds, resulted in significantly improved cellular transfection efficiency, significantly reduced cytotoxicity, and significantly increased distribution of small nucleic acids in the spleen of mice than direct administration.

For example, when delivering mRNA, the cellular transfection efficiency of YK-910 could reach 345.06 times that of YK-903 and 313.25 times that of YK-906, while its cytotoxicity could be 58% lower than that of YK-902. When delivering small nucleic acids, the fluorescence intensity of YK-908, YK-909, YK-910, and YK-912 in the spleen was 100.55 times, 126.85 times, 150.67 times, and 31.80 times that of direct administration, respectively. However, the distribution of small nucleic acids resulting from YK-912 in the kidney was 0.09 times that of direct administration.

4. Through unique design and screening, the present disclosure has identified several compounds, such as YK-908, YK-909, YK-910, and YK-912, which, compared with other structurally similar compounds in the prior art, could result in significantly improved cellular transfection efficiency, significantly reduced cytotoxicity, and significantly increased expression levels in the spleen of animals, thereby enhancing delivery efficiency and achieving unexpected technical effects.

The above is a detailed description of the present disclosure, intended to enable those skilled in the art to understand and implement the present disclosure. However, it should not be construed as limiting the scope of the present disclosure. Any equivalent changes or modifications made based on the spirit and essence of the present disclosure should be encompassed within the scope of protection of the present disclosure.

What is claimed is:

1. A compound of formula (I), (I)

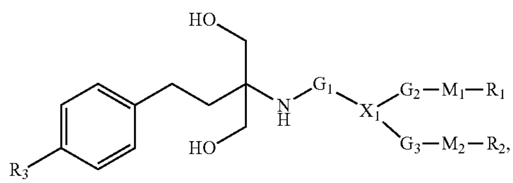

or a pharmaceutically acceptable salt thereof, or a stereoisomer thereof, wherein $G_1$ is $C_{1-4}$ alkylene;

$G_2$ is $C_{1-8}$ alkylene;

$G_3$ is $C_{2-8}$ alkylene;

$R_1$ is $C_{6-25}$ linear alkyl;

$R_2$ is

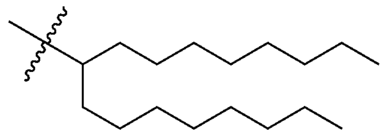

$R_3$ is $C_{1-25}$ linear alkyl, $C_{1-25}$ branched alkyl, or H;

$M_1$ is —C(O)O—, —OC(O)—, —C(O)N(R')—, —N(R')C(O)—, —C(O)—, or —CH(OH)—;

$M_2$ is —C(O)O—, —OC(O)—, —C(O)N(R')—, —N(R')C(O)—, —C(O)—, or —CH(OH)—;

R' is $C_{1-18}$ alkyl or H;

$X_1$ is —CH— or N.

2. The compound, or the pharmaceutically acceptable salt thereof, or the stereoisomer thereof according to claim 1, wherein $G_1$ is unsubstituted $C_1$ alkylene or unsubstituted $C_2$ alkylene;

or, $G_2$ is unsubstituted $C_1$ alkylene, unsubstituted $C_3$ alkylene, or unsubstituted $C_4$ alkylene;

or, $G_3$ is unsubstituted $C_5$ alkylene or unsubstituted $C_6$ alkylene;

or, $R_3$ is $C_8$ linear alkyl;

or, $M_1$ is —C(O)O—, —C(O)NH—, or —NHC(O)—;

or, $M_2$ is —C(O)O—.

3. The compound, or the pharmaceutically acceptable salt thereof, or the stereoisomer thereof according to claim 1, wherein the compound is YK-909

YK-909

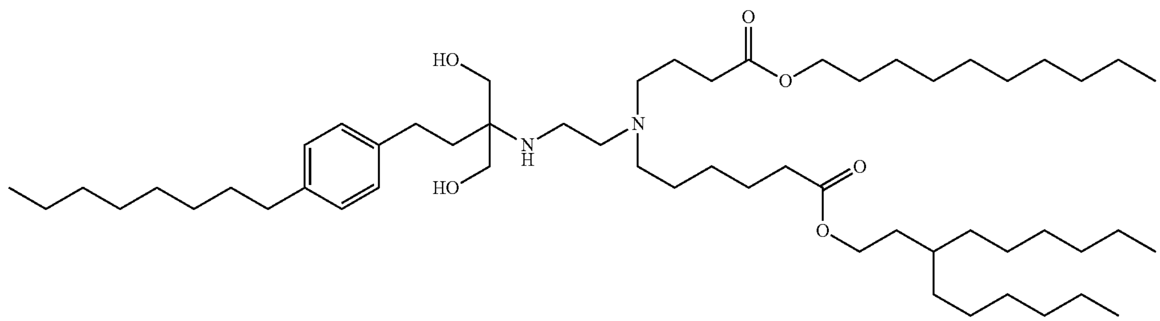

4. The compound, or the pharmaceutically acceptable salt thereof, or the stereoisomer thereof according to claim 1, wherein the compound is

YK-910

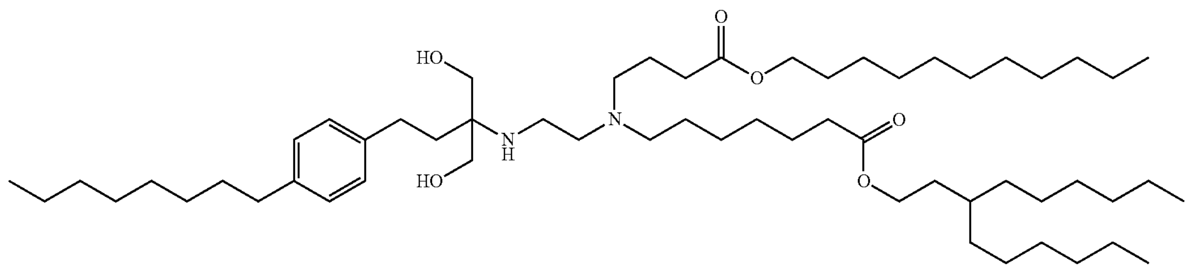

5. A compound, or the pharmaceutically acceptable salt thereof, or the stereoisomer thereof, wherein the compound is

YK-908

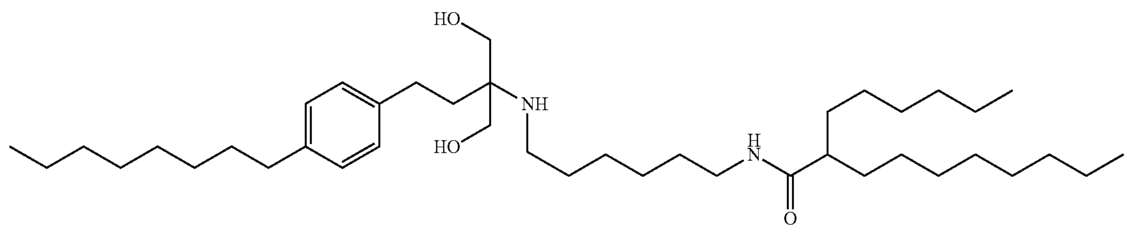

6. A compound, or the pharmaceutically acceptable salt thereof, or the stereoisomer thereof, wherein the compound is

YK-912

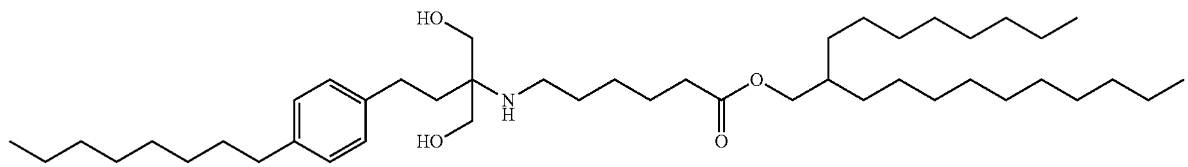

7. A composition comprising a vector, wherein the vector comprises a cationic lipid, and the cationic lipid comprises the compound, or the pharmaceutically acceptable salt thereof, or the stereoisomer thereof according to claim 1.

8. The composition according to claim 7, wherein the vector further comprises one or more of: a neutral lipid, a structural lipid and a polymer-conjugated lipid.

9. The composition according to claim 8, wherein the neutral lipid comprises one or more of phosphatidylcholine, phosphatidylethanolamine, sphingomyelin, ceramide, sterol, and derivatives thereof;

or, the structural lipid is selected from one or more of cholesterol, nonsterol, sitosterol, ergosterol, campesterol, stigmasterol, brassinosterol, tomatidine, ursolic acid, a-tocopherol, and corticosteroid;

or, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol.

10. The composition according to claim 9, wherein the neutral lipid is selected from one or more of 1,2-dilinoleoyl-sn-glycero-3-phosphocholine, 1,2-dimyristoyl-sn-glycero-phosphocholine, 1,2-dioleoyl-sn-glycero-3-phosphocholine, 1,2-dipalmitoyl-sn-glycero-3-phosphocholine, 1,2-distearoyl-sn-glycero-3-phosphocholine, 1,2-diundecanoyl-sn-glycero-phosphocholine, 1-palmitoyl-2-oleoyl-sn-glycero-3-phosphocholine, 1,2-di-O-octadecenyl-sn-glycero-3-phosphocholine, 1-oleoyl-2-cholesterylhemisuccinoyl-sn-glycero-3-phosphocholine, 1-hexadecyl-sn-glycero-3-phosphocholine, 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine, 1,2-diphytanoyl-sn-glycero-3-phosphoethanolamine, 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt, dipalmitoyl phosphatidylglycerol, palmitoyl oleoyl phosphatidylethanolamine, distearoyl-phosphatidyl-ethanolamine, dipalmitoyl phosphatidylethanolamine, dimyristoyl phosphoethanolamine, 1-stearoyl-2-oleoyl-sphingomyelin, stearoylethanolamine, 1-stearoyl-2-oleoyl-phosphatidylcholine, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine, and mixtures thereof;

or, the polymer-conjugated lipid is selected from one or more of distearoyl phosphatidylethanolamine polyethylene glycol 2000, dimyristoylglycero-3-methoxypolyethylene glycol 2000,and methoxypolyethylene glycol ditetradecylacetamide.

11. The composition according to claim 7, wherein the vector comprises a neutral lipid, a structural lipid, and a polymer-conjugated lipid, and the molar ratio of the cationic lipid, the neutral lipid, the structural lipid, and the polymer-conjugated lipid is (25 to 75):(5 to 25):(15 to 65):(0.5 to 10).

12. The composition according to claim 11, wherein the molar ratio of the cationic lipid, the neutral lipid, the structural lipid, and the polymer-conjugated lipid is 45:10:43.5:1.5 or 49:10:39.5:1.5;

or, the composition is a nanoparticle preparation, and the average particle size of the nanoparticle preparation is 10 nm to 300 nm; the polydispersity index of the nanoparticle preparation is ≤50%.

13. The composition according to claim 7, wherein the cationic lipid further comprises one or more other ionizable lipid compounds.

14. The composition according to claim 7, further comprising a therapeutic or prophylactic agent.

15. The composition according to claim 14, wherein the mass ratio of the vector to the therapeutic or prophylactic agent is 15:1;

or, the therapeutic or prophylactic agent comprises one or more of nucleic acid molecules, small molecule compounds, polypeptides, or proteins;

or, the therapeutic or prophylactic agent is a vaccine or compound capable of eliciting an immune response.

16. The composition according to claim 14, wherein the therapeutic or prophylactic agent is ribonucleic acid and/or deoxyribonucleic acid.

17. The composition according to claim 16, wherein the ribonucleic acid is selected from the group consisting of small interfering RNA, asymmetric interfering RNA, microRNA, dicer-substrate RNA, short hairpin RNA, messenger RNA, and mixtures thereof.

18. The composition according to claim 7, wherein the composition further comprises one or more pharmaceutically acceptable excipients or diluents.

* * * * *